US012441761B2

(12) United States Patent
James et al.

(10) Patent No.: US 12,441,761 B2
(45) Date of Patent: Oct. 14, 2025

(54) CONJUGATION REAGENTS AND METHODS USING 1,2-CYCLOHEXANEDIONES

(71) Applicant: Encodia, Inc., San Diego, CA (US)

(72) Inventors: Robert C. James, San Diego, CA (US); Stephen Verespy, III, San Diego, CA (US); Eric Cunyu Zhou, San Diego, CA (US); Eric Okerberg, San Diego, CA (US); Kelsey Rose Schramma, San Diego, CA (US); Fei Huang, San Diego, CA (US)

(73) Assignee: Encodia, Inc., San Diego, CA (US)

( * ) Notice: Subject to any disclaimer, the term of this patent is extended or adjusted under 35 U.S.C. 154(b) by 251 days.

(21) Appl. No.: 18/182,199

(22) Filed: Mar. 10, 2023

(65) Prior Publication Data

US 2023/0295222 A1 Sep. 21, 2023

Related U.S. Application Data

(60) Division of application No. 17/535,516, filed on Nov. 24, 2021, now Pat. No. 11,639,366, which is a (Continued)

(51) Int. Cl.
*C07K 1/13* (2006.01)
*C07C 49/603* (2006.01)
(Continued)

(52) U.S. Cl.
CPC .............. *C07K 1/13* (2013.01); *C07C 49/603* (2013.01); *C07D 235/02* (2013.01); (Continued)

(58) Field of Classification Search
CPC ...... C07K 1/13; C07K 1/1072; C07D 235/02; G01N 33/582; G01N 33/68; G01N 33/532; G01N 33/58
See application file for complete search history.

(56) References Cited

U.S. PATENT DOCUMENTS 6,162,922 A 12/2000 Anderson et al.
6,875,851 B1 4/2005 Travis et al.
(Continued)

FOREIGN PATENT DOCUMENTS

WO WO 2020/223000 11/2020

OTHER PUBLICATIONS

Cotham et al., "Proteomic analysis of arginine adducts on glyoxal-modified ribonuclease," Mol Cell Proteomics (Dec. 2004) 3(12):1145-1153.

(Continued)

*Primary Examiner* — Shafiqul Haq
(74) *Attorney, Agent, or Firm* — DLA PIPER LLP (US); Bu Yin

(57) ABSTRACT

The present invention relates to methods to use cyclohexan-1,2-dione (CHD) groups to attach labels, linkers, and other molecules to a target compound comprising a CHD-reactive group such as a guanidine, amidine, urea, thiourea and the like. Methods of the invention include milder conditions than those previously known for promoting reaction of CHD with CHD-reactive groups, which makes the methods suitable for use with base-sensitive compounds and complex biomolecules. Methods of the invention are especially useful for attaching linking and labeling groups to a peptide that comprises at least one arginine residue, and can also be used to link such peptides to other target molecules such as nucleic acids. The invention also provides CHD-containing conjugation reagents and compositions comprising CHD-containing intermediates, and precursors useful for making CD-containing compounds that can be used in the methods of the invention.

9 Claims, 19 Drawing Sheets

Specification includes a Sequence Listing.

Related U.S. Application Data continuation of application No. PCT/US2021/057144, filed on Oct. 28, 2021.

(60) Provisional application No. 63/108,282, filed on Oct. 30, 2020.

(51) Int. Cl.

| | |
|---|---|
| ***C07D 235/02*** | (2006.01) |
| ***C07K 1/107*** | (2006.01) |
| ***G01N 33/58*** | (2006.01) |
| ***G01N 33/68*** | (2006.01) |

(52) U.S. Cl.

CPC ......... *C07K 1/1072* (2013.01); *G01N 33/582* (2013.01); *G01N 33/68* (2013.01)

(56) References Cited

U.S. PATENT DOCUMENTS

| | | | |
|---|---|---|---|
| 11,639,366 | B2 | 5/2023 | James et al. |
| 2007/0020624 | A1 | 1/2007 | Rubenfield et al. |
| 2009/0264300 | A1 | 10/2009 | Franch et al. |
| 2016/0177404 | A1 | 6/2016 | McKernan |
| 2019/0145982 | A1 | 5/2019 | Chee et al. |
| 2019/0151448 | A1 | 5/2019 | Abel et al. |
| 2020/0348308 | A1 | 11/2020 | Chee et al. |

OTHER PUBLICATIONS

Debets et al., “Bioorthogonal labelling of biomolecules: new functional handles and ligation methods,” Org Biomol Chem (Oct. 14, 2013) 11(38):6439-6455.

Lee et al., “Monochromophoric Design Strategy for Tetrazine-Based Colorful Bioorthogonal Probes with a Single Fluorescent Core Skeleton,” J Am Chem Soc (Jan. 24, 2018) 140(3):974-983.

Patthy et al., “Reversible modification of arginine residues. Application to sequence studies by restriction of tryptic hydrolysis to lysine residues,” J Biol Chem (Jan. 25, 1975) 250(2):557-564.

Ramil et al., “Bioorthogonal chemistry: strategies and recent developments,” Chem Commun (Camb) (Dec. 7, 2013) 49(94):11007-11022.

Wanigasekara et al., “Arginine-Selective Chemical Labeling Approach for Identification and Enrichment of Reactive Arginine Residues in Proteins,” ACS Omega (Oct. 26, 2018) 3(10):14229-14235.

Wanigasekara et al., “Evaluation of chemical labeling methods for identifying functional arginine residues of proteins by mass spectrometry,” Anal Chim Acta (Sep. 7, 2016) 935:197-206.

Wilbur et al., “Streptavidin in antibody pretargeting. 3. Comparison of biotin binding and tissue localization of 1,2-cyclohexanedione and succinic anhydride modified recombinant streptavidin,” Bioconjug Chem (2002) 13(3):611-620.

1. 2. 3.

1. 2. 3.

SYBR Gold
1. HRT(34nt)
2. HRT-PEG4-TCO
3. HRT-PEG4-PEG4-TAMRA
4. HRT-PEG4-TAMRA-CHD TAMRA
5. HRT(34nt)
6. HRT-PEG4-TCO
7. HRT-PEG4-PEG4-TAMRA
8. HRT-PEG4-TAMRA-CHD

CONJUGATION REAGENTS AND METHODS USING 1,2-CYCLOHEXANEDIONES

RELATED APPLICATIONS

The present application is a divisional of U.S. non-provisional patent application Ser. No. 17/535,516, filed Nov. 24, 2021, now allowed, which is a continuation application of International Patent Application Serial No. PCT/US2021/057144, filed on Oct. 28, 2021, entitled "CONJUGATION REAGENTS AND METHODS USING 1,2-CYCLOHEXANEDIONES", which claims priority to U.S. provisional patent application No. 63/108,282, filed on Oct. 30, 2020. The disclosures and contents of the above-referenced applications are incorporated by reference in their entireties for all purposes.

REFERENCE TO AN ELECTRONIC SEQUENCE LISTING

The content of the electronic sequence listing (2002701_SeqList.xml; Size: 26,041 bytes; and Date of Creation: Mar. 8, 2023) is herein incorporated by reference in its entirety.

TECHNICAL FIELD

The field of this invention is compounds and methods using cyclohexanedione (CHD) in combination with other reactive handles to label and/or link biological molecules such as peptides and nucleic acids. Reagents and methods of the invention enable a user to label or link biomolecules and to monitor the rate and/or extent of the labeling and linking reactions in progress using fluorogenic markers.

BACKGROUND

Attaching linking groups, labels, markers, and fluorogenic probes to biological molecules such as peptides and nucleic acids for the purpose of labeling the biological molecules or linking one biomolecule to another are vital to advancing our understanding of complex biological systems. Ideally, such conjugates can be formed selectively and in good yield under conditions where the biological molecules are stable and functional, e.g., in a biological medium. Methods for attaching groups to biological molecules are known, but there remains a need for new methods complementary to existing ones and methods that are more selective and efficient than those known. Linking methods take advantage of various reactive handles that are suitable for use in complex biological systems to connect biomolecules together. These reactive handles must react under mild conditions with high selectivity in order to be useful in complex mixtures, and preferably they should function in substantially aqueous media compatible with normal structure and function of biomolecules.

For example, one reaction used to modify a protein or peptide containing arginine is the reaction between the guanidinyl group of arginine and a 1, 2-cyclohexanedione (CHD). The reaction of arginine with CHD is well known, and provides a relatively homogeneous product under basic conditions. For example, it is reported that CID reacts with arginine relatively rapidly in 0.2 N hydroxide solution, but produces a mixture of products at lower concentration of base (0.05 N). K. Toi, et al., J. Biol. Chem. 1967, 242(5), 1036-43.

Many practical applications require to specifically label polypeptides obtained from protein samples with a nucleic acid tag (MacCulloch T, et al., Emerging applications of peptide-oligonucleotide conjugates: bioactive scaffolds, self-assembling systems, and hybrid nanomaterials. Org Biomol Chem. 2019 Feb. 13; 17(7):1668-1682). It is often required to perform the coupling between polypeptides and nucleic acids under mild conditions to preserve integrity of the polypeptide and the nucleic acid, as well as potential post-translational modifications of the polypeptide, such as phosphorylation. In one application, obtained polypeptide-polynucleotide conjugates can be further used in downstream processes, such as polypeptide sequencing, as described in US 20190145982 A1, US 20200348308 A1, US 20200348307 A1, WO 2020/223000, the contents of which are incorporated herein by reference in their entireties.

While many suitable complementary pairs of reactive handles are known in the literature for modifying, labeling, and linking biomolecules, such as polypeptides and nucleic acids, the present disclosure provides methods of using CHD groups and CHD-reactive groups for these purposes, and thus provides a new and highly versatile bioorthogonal chemistry. The present disclosure further provides reaction conditions that facilitate efficient and irreversible reaction of a CHD group with a CHD-reactive group, where the reaction conditions are much milder than previously reported conditions, and, as a result, are compatible with downstream polypeptide sequencing applications.

Immobilization approaches for polypeptides disclosed herein can be utilized for other potential manipulations with peptides, such as labeling of peptides with a purification handle or a detectable label, modifications of amino acid side chains, peptide sequence manipulation, and so on. Some of the disclosed immobilization approaches allow for traceless, reversible, covalent attachment of peptides obtained from biological samples.

The invention is illustrated by the description, examples and figures below.

BRIEF SUMMARY

Arginine modification by CHD has been known to yield near quantitative and homogeneous imidazolidinone derivatives in the presence 0.2M or greater NaOH (Bynum et al., *The Journal of Biological Chemistry*, (1967) 242(5):1036-1043). However, the strongly alkaline condition necessary for the reaction to go to completion prevents the use of CHD in broader proteomic applications, as it may cause hydrolytic cleavage of peptide bonds, undesired removal of protein posttranslational modifications and other useful chemical modifications of protein side chains, and result in incompatibility of conjugating other base-labile functional molecules and reactive functional groups to the linker, protein and peptide of interest. Kemp, *FEBS LETTERS* (1980) 110(2):308-312; Boger et al., *J. Org. Chem.* 1985, 50(25): 5377-5379. It has also been reported that lowering the pH of reaction condition by simply reducing the NaOH concentration is insufficient to render the reaction useful in complex systems, as it may lead to the formation of heterogeneous products including a reversible adduct, making it difficult to analyze the products and impractical for proteomic applications. Therefore, in order to fully harness the high selectivity, reaction kinetics and product stability of the CHD-arginine reaction for a variety of chemical and biological applications, it is crucial to use milder CHD-arginine conjugation conditions.

The reaction mechanism of arginine guanidinium side chain and 1,2-dicarbonyl derivatives such as CHD have been extensively studied (Cotham et al., *Molecular & Cellular Proteomics* (2004) 3(12):1145-1153; Kentaro et al., *Bulletin of the Chemical Society of Japan* (1969) 42(11): 3314-3317; Patthy et al., *The Journal of Biological Chemistry* (1974) 250(2): 557-564). However, as discussed above, the standard conditions used to promote the CHD-arginine reaction (pH about 13.5 or higher) can be detrimental to some target molecules and to some additional reactive handles that might otherwise be ideal for use in the conjugation reagents and methods of the invention. The invention provides methods to use the reaction of cyclohexan-1,2-dione groups with CHD-reactive groups under conditions sufficiently mild to allow use of this reaction to be used with mixtures of complex biomolecules, which provides a valuable bioorthogonal conjugation method.

For many applications, such as linking two biomolecules together or attaching a label to a biomolecule, the invention provides a conjugation reagent containing a CHI) group and an additional reactive handle that can be used to link a first biomolecule that is connected to the conjugation reagent via the CHD chemistry discussed above, to a second moiety including another complex biomolecule. Suitable reactive handles that are orthogonal to CHD as a primary linking chemistry are ones that can be used in biological media and are sufficiently reactive and selective to avoid reacting with typical biomolecules and biological media components, so they preferentially react with complementary reactive groups not typically present in biological systems. Such reactive groups are readily incorporated into target molecules by methods known in the art. So-called ‘click chemistry’ reactants are commonly used in biological systems, and are orthogonal to CHD linking chemistry and are thus useful as additional reactive handles in the CHD-containing conjugation reagents and methods of the invention. Click chemistry reactive handles include reactants for inverse-electron demand Diels-Alder reactions, such as tetrazines, which react efficiently with a variety of activated alkene and alkyne groups such as cyclopropenes and trans-cyclooctene, and reactants for [3+2]cycloadditions, such as azide which reacts efficiently with an electron rich alkene or alkyne. These can be used in combination with the CHD reactions, as they provide orthogonal reactive handles and are typically compatible with biological systems.

While many suitable complementary pairs of reactive handles are known in the literature for modifying, labeling, and linking biomolecules, the invention provides methods of using CHD groups and CHD-reactive groups for these purposes, and thus provides a new and highly versatile bioorthogonal chemistry. The invention further provides reaction conditions that facilitate efficient and irreversible reaction of a CHD group with a CHD-reactive group, where the reaction conditions are much milder than previously reported conditions, and are as a result compatible with use to modify, label, and/or link complex biomolecules in aqueous media. The invention further provides compounds that comprise a CHD group and are useful in the methods of the invention.

In one aspect or embodiment, the present disclosure provides improved methods to use a CHD group as a reactive handle for attaching a moiety to a target compound that contains a CHD-reactive group such as arginine, urea, thiourea, amidine, and the like. The invention provides a method to attach a conjugation reagent to a target molecule, wherein:

the conjugation reagent comprises a 1,2-cyclohexanedione (CHD) group; and the target molecule comprises a CHD-reactive group;

and the method comprises contacting the conjugation reagent with the target molecule under reaction conditions that cause the CHD-reactive group to react irreversibly with the CHD group to form a modified target molecule having a covalent linkage connecting the conjugation reagent and the target molecule, wherein the reaction conditions comprise an aqueous medium at a pH less than 13.

The method comprises contacting the target compound comprising a CHD-reactive group with a conjugation reagent that comprises a CHD moiety, under reaction conditions that promote an irreversible reaction linking the CHD group to the CID-reactive group. Preferably the conditions are not strongly basic, such as pH below 13, sometimes below 12.5, sometimes below 12. The reaction medium is aqueous, i.e., at least 50% water, and can include one or more organic co-solvents. The methods permit attaching a linker or conjugation reagent that contains a CHD group and additional functional groups (labels, reactive handles, binding groups, and the like) to a target compound under reaction conditions that are mild enough to permit other reactive handles, biomolecules, functional groups, labels, and the like to be present on the conjugation reagent or target compound, or present in the reaction mixture, without being destroyed by the conditions required for irreversible CHD conjugation.

Suitable target compounds include peptides, carbohydrates, nucleic acids, and other biomolecules that comprise at least one CHD-reactive group. The CHD-reactive group can be a natural component of the target molecule, e.g., an arginine residue in a peptide, or it can be introduced by modification of the target molecule. Suitable target compounds comprise at least one CHD-reactive group such as guanidine, urea, amidine, or thiourea, and can optionally contain more than one CHD-reactive group and/or a detectable label and/or one or more additional reactive handles. Suitable conjugation reagents comprise at least one CHD group, and optionally a detectable label or an additional reactive group for attaching the conjugation reagent to other target compounds, detectable labels, and the like via methods complementary to the CHD chemistry.

The reaction conditions for the CHD conjugation methods of the invention comprise an aqueous medium at a pH of 13 or less, preferably 12.5 or lower, more preferably 12 or lower. The aqueous medium typically comprises a buffer, preferably at a concentration of at least 0.1 M, typically at least 0.5M, and preferably 1M or higher, as the higher ionic strength of such aqueous media are believed to accelerate the reaction of a CHD group with a CHD reactive group. The reaction can be conducted at any suitable temperature, but typically it is conducted at a temperature of at least 20° C., in some embodiments at a temperature between 35 and 50° C., in some embodiments at a temperature between about 50 and 60° C., in some embodiments at a temperature between 6° and 80° C., and in some embodiments at a temperature higher than 80° C.

In another aspect or embodiment, the invention provides a conjugation reagent that comprises a CHD group and an additional reactive handle or a detectable label or both, preferably where the additional reactive handle or detectable label is base sensitive and thus not compatible with methods of the prior art for irreversibly reacting a CHD group with a CHD reactive group. In some embodiments, the conjugation reagent comprises at least one linking group connecting the CHD group and additional reactive handle, where the linking group is hydrophilic and thus increases compatibility of the conjugation reagent with the aqueous media used in the methods of the invention.

In another aspect or embodiment, the invention provides methods as described above wherein the conjugation reagent comprises a CHD-reactive group and a detectable label.

In another aspect or embodiment, the invention provides a conjugation reagent suitable for use in the foregoing methods. The conjugation reagent comprises at least one CHD group and a base-sensitive reactive handle. In some embodiments, the reactive handle is a bioorthogonal reactive handle. In some embodiments, the base-sensitive reactive handle comprises an ester, a thioester, a nitrile, an alkylating agent, a tetrazine ring, a phosphate ester, or a phospholipid.

In another aspect or embodiment, the invention provides a multifunctional conjugation reagent that comprises at least one CHD group, and a detectable label, and an additional reactive handle. In some embodiments, the detectable label comprises a fluorogenic moiety.

In another aspect or embodiment, the invention provides cyclohexane-1,2-dione compounds useful in the methods described above as well as intermediates useful for the synthesis of the conjugation reagents described above.

In another aspect or embodiment, the invention provides conjugates that comprise a target compound such as a peptide linked to a conjugation reagent, where the linkage is formed by reaction of a CHD group with a CHD-reactive group. Some embodiments include peptide-nucleic acid conjugates wherein the peptide is linked to the nucleic acid via a conjugation reagent of the invention.

In another aspect or embodiment, the invention provides a linking reagent that comprises a CHD group and at least one reactive handle connected together via a hydrophilic linker.

In another aspect or embodiment, the invention provides a method to attach a modifier to a target molecule, wherein either the modifier or the target molecule comprises a 1,2-cyclohexanedione (CHD) group, and the other of the two (modifier or target molecule) comprises a CHD-reactive group, where the method comprises contacting the modifier with the target molecule under reaction conditions that cause the CHD-reactive group to react irreversibly with the CHD group to form a modified target molecule having a covalent linkage connecting the conjugation reagent and the target molecule, where the reaction conditions comprise using an aqueous medium at a pH less than 13.

These and other aspects and embodiments of the invention are represented and enabled by the detailed description and examples below.

BRIEF DESCRIPTION OF THE DRAWINGS

Non-limiting embodiments of the present invention will be described by way of example with reference to the accompanying figures, which are intended to illustrate some variations of the methods and compositions of the invention. For purposes of illustration, not every component is labeled in every figure, nor is every component of each embodiment of the invention shown where illustration is not necessary to allow those of ordinary skill in the art to understand the invention.

FIG. 4A) and a leucine binding agent (L-binder; FIG. 4B).

DETAILED DESCRIPTION

The following description and examples are intended to illustrate and exemplify certain aspects and embodiments of the invention but are not intended to limit its scope. The scope of the various aspects of the invention is defined by the claims and enumerated embodiments.

Figure 3:
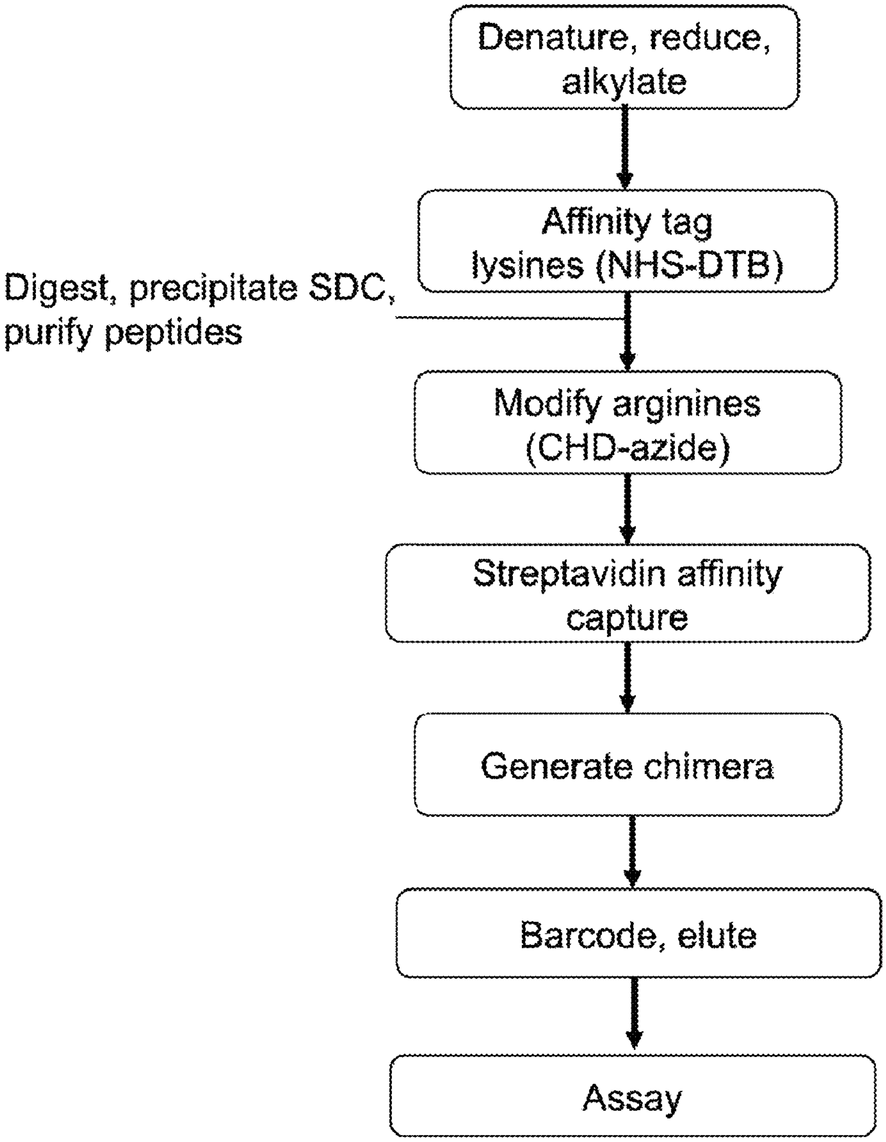
FIG. 3 is a schematic depicting an exemplary sample preparation workflow.

Methods and compositions of the invention can be used for any suitable purpose. They are suitable for use in preparing samples for analysis and for preparing libraries of conjugates, such as methods schematically represented in FIG. 3 and FIG. 7. They can be used in methods such as those disclosed in US20190145982 A1 (for example, the ProteoCode™ assay) for analyzing peptides and tagging peptides with nucleic acids.

General Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, =O, =N—CN, =N—OR$^a$, =NR$^a$, —OR$^a$, —NR$^a_2$, —SR$^a$, —SO$_2$R$^a$, —SO$_2$NR$^a_2$, —NR$^a$SO$_2$R$^a$, —NR$^a$CONR$^a_2$, —NR$^a$COOR$^a$, —NR$^a$COR$^a$, —CN, —COOR$^a$, —CONR$^a_2$, —OOCR$^a$, —COR$^a$, and —NO$_2$, wherein each R$^a$ is independently H, C1-C8 alkyl, C2-C8 heteroalkyl, C3-C8 heterocyclyl, C4-C10 heterocyclylalkyl, C1-C8 acyl, C6-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR$^b$, =NR$^b$, OR$^b$, NR$^6_2$, SR$^b$, SO$_2$R$^b$, SO$_2$NR$^b_2$, NR$^b$SO$_2$R$^b$, NR$^b$CONR$^b$, NR$^b$COOR$^b$, NR$^b$COR$^b$, CN, COOR$^b$, CONR$^b_2$, OOCR$^b$, COR$^b$, and NO$_2$, wherein each R$^b$ is independently H, C1-C8 alkyl, C2-C8 heteroalkyl, C3-C8heterocyclyl, $C_4$-$C_{10}$ heterocyclylalkyl, $C_1$-$C_8$ acyl, $C_2$-$C_8$ heteroacyl, $C_6$-$C_{10}$ aryl or C5-C10 heteroaryl. Alkyl, alkenyl and alkynyl groups can also be substituted by $C_1$-$C_8$ acyl, C2-C8 heteroacyl, $C_6$-$C_{10}$ aryl or $C_5$-$C_{10}$ heteroaryl, each of which can be substituted by the substituents that are appropriate for the particular group. Where a substituent group contains two R$^a$ or R$^b$ groups on the same or adjacent atoms (e.g., —NR$^b_2$, or —NR$^b$—C(O) R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups asset forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —OR, $—NR^a_2$, $—SR^a$, $—SO_2R^a$, $—SO_2NR^a_2$, $—NR^aSO_2R^a$, $—NR^aCONR^a_2$, $—NR^aCOOR^a$, $—NR^aCOR^a$, —CN, $—COOR^a$, $—CONR^a_2$, $—OOCR^a$, $—COR^a$, and $—NO_2$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocyclylalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each $R^a$ is optionally substituted with halo, —O, =N—CN, $=N—OR^b$, $=NR^b$, $OR^b$, $NR^b_2$, $SR^b$, $SO_2R^b$, $SO_2NR^b_2$, $NR^bSO_2R^b$, $NR^bCONR^b_2$, $NR^bCOOR^b$, $NR^bCOR^b$, CN, $COOR^b$, $CONR^b_2$, $OOCR^b$, $COR^b$, and $NO_2$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocyclylalkyl, $C_1$-$C_8$ acyl, $C_2$-$C_8$ heteroacyl, $C_6$-$C_{10}$ aryl or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. Where a substituent group contains two $R^a$ or $R^b$ groups on the same or adjacent atoms (e.g., $—NR^b_2$, or $—NR^b—C(O) R^b$), the two $R^a$ or $R^b$ groups can optionally be taken together with the atoms in the substituent group to which are attached to form a ring having 5-8 ring members, which can be substituted as allowed for the $R^a$ or $R^b$ itself and can contain an additional heteroatom (N, O or S) as a ring member.

As also used herein, the terms "imidazopyridine" or "imidazopyrimidine" or "thiazopyridine" or "thiazopyrimidine" herein refer to any compound in which the two designated heterocyclic rings are fused by any two adjacent atoms on the two heterocyclic rings.

The term "alkoxy" as used herein refers to a hydrocarbon group connected through an oxygen atom, e.g., —O—Hc, wherein the hydrocarbon portion He may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S—Hc, wherein the hydrocarbon portion Hc is as described for alkoxy groups. For example, contemplated alkylthio groups include methylthio, ethylthio, isopropylthio, methoxyethylthio, benzylthio, allylthio, and the like.

The term 'amino' as used herein refers to the group $—NH_2$. The term "alkylamino" refers to amino groups where one or both hydrogen atoms are replaced by a hydrocarbon group He as described above, wherein the amino nitrogen "N" can be substituted by one or two He groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group Hc as described above, wherein the amino nitrogen "N" can be substituted by one or two He groups as set forth for alkoxy groups described above.

The term 'acyl' as used herein refers to a group of the formula —C(=O)-D, where D represents an alkyl, alkenyl, alkynyl, cycloalkyl, aryl, heteroaryl, or heterocycle as described above. Typical examples are groups wherein D is a C1-C10 alkyl, C2-C10 alkenyl or alkynyl, or phenyl, each of which is optionally substituted. In some embodiments, D can be H, Me, Et, isopropyl, propyl, butyl, C1-C4 alkyl substituted with —OH, —OMe, or $NH_2$, phenyl, halophenyl, alkylphenyl, and the like.

The term "aryloxy" as used herein refers to an aryl group connecting to an oxygen atom, wherein the aryl group may be further substituted. For example, suitable aryloxy groups include phenyloxy, etc. Similarly, the term "arylthio" as used herein refers to an aryl group connecting to a sulfur atom, wherein the aryl group may be further substituted. For example, suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O— wherein one or more hydrogen atoms on the alkyl group have been substituted with a halo group and include, by way of examples, groups such as trifluoromethoxy, and the like.

The term "sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein each alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

The term "sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "acylamino" refers to the groups —$NR^{20}$C(O)alkyl, —$NR^{20}$C(O)substituted alkyl, —$NR^{20}$C(O)cycloalkyl, —$NR^{20}$C(O)substituted cycloalkyl, —$NR^{20}$C(O)cycloalkenyl, —$NR^{20}$C(O)substituted cycloalkenyl, —$NR^{20}$C(O)alkenyl, —$NR^{20}$C(O)substituted alkenyl, —$NR^{20}$C(O)alkynyl, —$NR^{20}$C(O)substituted alkynyl, —$NR^{20}$C(O)aryl, —$NR^{20}$C(O)substituted aryl, —$NR^{20}$C(O)heteroaryl, —$NR^{20}$C(O)substituted heteroaryl, —$NR^{20}$C(O)heterocyclic, and —$NR^{20}$C(O)substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "aminocarbonylamino" refers to the group —$NR^{20}C(O)NR^{21}R^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

It should further be recognized that all of the above-defined groups may further be substituted with one or more substituents, which may in turn be substituted with hydroxy, amino, cyano, $C_1$-$C_4$ alkyl, halo, or $C_1$-$C_4$ haloalkyl. For example, a hydrogen atom in an alkyl or aryl can be replaced by an amino, halo or $C_{1-4}$ haloalkyl or alkyl group.

The term "substituted" as used herein refers to a replacement of a hydrogen atom of the unsubstituted group with a functional group, and particularly contemplated functional groups include nucleophilic groups (e.g., —$NH_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —$NH_3^+$), and halogens (e.g., —F, —Cl), NHCOR, $NHCONH_2$, $OCH_2COOH$, $OCH_2CONH_2$, $OCH_2CONHR$, $NHCH_4COOH$, $NHCH_2CONH_2$, $NHSO_2R$, $OCH_2$-heterocycles, $PO_3H$, $SO_3H$, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent “arylalkyloxycarbonyl” refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term “pharmaceutically acceptable salt” means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. “Pharmaceutically acceptable salt” refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term “salt thereof” means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

As used herein, the term ‘bioorthogonal reactive handle’ refers to a reactive moiety that is stable in typical biological media and systems, and reacts specifically with appropriate non-biological reactive groups under mild conditions that do not damage the biological system. Examples of bioorthogonal reactive handles include tetrazines (which can react with strained alkenes and alkynes such as cyclopropenes, trans-cyclooctene, cyclooctyne, and the like); alkyl azides (which take part in ‘click’ reactions with terminal alkynes and alkenes); phosphines and azides (which can take part in Staudinger ligation reactions to form amide bonds). Examples of bioorthogonal reactive handles and strategies for using them are well known in the art. See e.g., C. P. Ramil, et al., *Chem. Commun.* 2013, vol. 49, 11007-11022; M. F. Debets, et al., *Org, Biomol. Chem.* 2013, vol. 11, 6439.

CHDs are not typically considered bioorthogonal reactive handles, because they react specifically with components of biological systems, e.g. the guanidinyl group of arginine residues in peptides and proteins. Instead, they are recognized as effective reactive handles for selectively labeling arginine residues in peptides and proteins. They are useful for attaching probes or other molecules to peptides under mild conditions. M. Wanigasekara, et al., *ACS Omega* 2018, 3, 14, 229-35. They can also be used in combination with bioorthogonal reactive handles to label a peptide and attach another moiety to it. However, as described herein, they have not heretofore been useful in more complex systems because of the reaction conditions needed for the conjugation reaction.

As used herein, the term “inverse diene” refers to an electrone poor diene capable of reacting with an electron-rich multiple bond in an inverse-electron demand Diels-Alder reaction, such as a 1,2,4,5-tetrazine.

As used herein, the term “detectable label” refers to a substance which can indicate the presence of another substance when associated with it. The detectable label can be a substance that is linked to or incorporated into the substance to be detected. In some embodiments, a detectable label is suitable for allowing for detection and also quantification, for example, a detectable label that emitting a detectable and measurable signal. Detectable labels include any labels that can be utilized and are compatible with the provided peptide analysis assay format and include, but not limited to, a bioluminescent label, a biotin/avidin label, a chemiluminescent label, a chromophore, a coenzyme, a dye, an electro-active group, an electrochemiluminescent label, an enzymatic label (e.g. alkaline phosphatase, luciferase or horseradish peroxidase), a fluorescent label, a latex particle, a magnetic particle, a metal, a metal chelate, a phosphorescent dye, a protein label, a radioactive element or moiety, and a stable radical.

Examples of detectable labels especially useful for methods and compositions described herein include, but are not limited to, 1,4,7,10-Tetraazacyclododecane-1,4,7,10-tetrancetic acid (DOTA), desthiobiotin, TAMRA, fluorogenic labels, isobaric mass tags, and 2-formylphenylboronic acid.

The term “CHD” as used herein, refers to a 1,2-cyclohexanedione ring, which can be substituted as described herein. For the methods and compositions of the invention, the CHD is typically attached to or part of a conjugation reagent. A CHD can be attached to a conjugation reagent at any of the available carbon atoms of the cyclohexanedione ring, and can be further substituted as described herein.

The term “CHD-reactive group” as used herein refers to a reactive group that reacts specifically and irreversibly with a 1,2-cyclohexanedione under conditions compatible with the presence of a target compound. Typically, a CHD-reactive group is selective for reaction with a CHD over most other reactive groups. Examples of CHD-reactive groups include guanidines, amidines, ureas and thioureas.

The term ‘conjugation reagent’ or ‘linking group’ as used herein refers to an organic moiety that can be used to, or is used to, connect (link) two moieties. Examples include connecting a target compound to at least one other molecule, such as a reactive handle, functional group, label, binding group, tag, or target compound, A conjugation reagent can be substituted with various groups such as reactive handles and/or detectable labels. For example, a first target compound such as an arginine-containing peptide can be covalently attached to a conjugation reagent via the CHD-reactive group of the conjugation reagent to form a ‘first target-conjugation reagent’ conjugate. With a conjugation reagent that contains an additional reactive handle that remains intact when the conjugation reagent's CHD reacts with a CHD-reactive group to attach the conjugation reagent to the first target compound, the additional reactive handle can be used to connect the ‘first target-conjugation reagent conjugate’ to a second target compound that contains a functional group that can react with the additional reactive handle of the conjugation reagent. For simplicity, the resulting product can be described as a ‘first target-conjugation reagent-second target’ conjugate, even though a CHD group and an additional reactive handle of the original conjugation reagent compound have been modified by the reactions that formed the 'first target-conjugation reagent-second target' conjugate. The person of ordinary skill will understand that the reactive group structures change during the course of reactions that occur as part of the methods described herein, and while a conjugation reagent attached to a target compound has a structure that is necessarily modified during attachment it is still referred to as a conjugation reagent or linking group. Unless otherwise described, a conjugation reagent can comprise one or more groups selected from a nucleotide, a nucleotide analog, an amino acid, a peptide, a polypeptide, aryl ring, heteroaryl ring, heterocyclic ring, carbocyclic ring, one or more polyethylene glycol (PEG) subunits including a PEG chain containing up to 100 or more PEG units. A conjugation reagent may be used to join a binding agent with a coding tag, a recording tag with a macromolecule (e.g., peptide), a macromolecule with a solid support, a recording tag with a solid support, etc. In certain embodiments, a conjugation reagent joins two molecules via enzymatic reaction or chemical reaction (e.g., click chemistry).

Conjugation reagents that comprise a detectable label are sometimes referred to herein as 'probes' or 'fluorogenic probes.'

Conjugation reagents comprise a CHD group and at least one reactive handle, and optionally a detectable label and/or an organic scaffold. The components of the conjugation reagent are connected together as a single molecule. Frequently, the components will be connected by one or more linkers, which serve to provide a desired degree of spacing and relative orientation of the components. Linkers can be alkyl groups or rings or combinations of alkyl groups and rings, including aryl rings, heteroaryl rings, heterocyclic rings, and carbocyclic rings, and are often connected together and to components of the conjugation reagent by stable functional groups like amides, ethers, thioethers, thioamides, sulfones, and the like. Linkers can comprise hydrophilic features such as PEG groups and amides to promote water miscibility Selection and construction of conjugation reagents and use of linkers in them are well within the ordinary level of skill in view of the guidance and examples herein.

The term "modifier" as used herein refers to a chemical moiety that can usefully be chemically attached to a target compound to modify the structure and properties of the target compound; the modifier comprises at least one reactive handle. In particular, the modifier typically comprises either a CHD group or a CHD-reactive group. When the modifier comprises a CHD, it can be used to modify a target compound that comprises at least one CHD-reactive group, using the reaction conditions described herein. When the modifier comprises a CHD-reactive group, it can be used to modify a target compound that comprises a CHD group, using the reaction conditions described herein. Typical modifiers can comprise a detectable label, an additional reactive handle, a chemical group that enhances water solubility, such as a PEG group, a tag to facilitate separation or immobilization of the target molecule (e.g., biotin, avidin, streptavidin, poly-His), or a solid support or surface such as a bead or a slide.

The term 'acylated $NH_2$' as used herein refers to an $NH_2$ group that is attached to a C═X group, where X is O, S or NR, where R is H or $C_{1-4}$ alkyl. Acylated $NH_2$ groups include guanidine, urea, thiourea, and amidine groups.

The term "fluorogenic moiety", as used herein, refers to a moiety that contributes to generation of a fluorescent signal that can be detected. Fluorogenic moieties include fluorescent groups, such as fluorescent dyes disclosed herein, fluorescence quenchers, and combination of these. In some embodiments, a fluorogenic moiety comprises a fluorophore proximal to a moiety that interacts through bonds or through space with the fluorophore, such as a quencher. In these embodiments, the presence of or changes in the fluorophore can be used to monitor the progress of reactions used to modify a target molecule or to link a first target molecule to a second target molecule.

The term 'aqueous medium' as used herein refers to a solvent or solvent mixture that is predominantly water, i.e., at least 50% water by volume. The aqueous medium can include one or more co-solvents, including organic co-solvents such as acetonitrile, DMSO, DMF, DMA, NMP, TMU, cyrene, sulfolane, 2-methyl THF, limonene, 1,3-dimethylpyridone, THF, dioxane, DME, alcohols such as methanol, ethanol, isopropanol, t-butanol, n-butanol, ethylene glycol, propylene glycol, polyethylene glycol, and the like. In some embodiments, the aqueous medium comprises 1-25% organic cosolvent such as those just named, or a mixture of those. In some embodiments, the aqueous medium comprises 1-10% organic cosolvents. In some embodiments, the aqueous medium comprises 10-20% organic cosolvents.

As used herein, the term "reactive handle" refers to a moiety on a first molecule that can be caused to react with a second molecule having a complementary 'reactive handle' to form a covalent bond between the first molecule and the second molecule. Typical reactive handles include functional groups such as carboxylate groups and amines, which can react with each other to form amides; thiols and alkylating reagents that can be reacted to form thioethers, thiols and maleimides that can be reacted to form thiosuccinimides; strained alkenes or alkynes and 1,3-dipoles such as azides that can react via cycloaddition reactions, e.g., copper-free click chemistry; and tetrazines that can react via inverse-electron demand Diels-Alder chemistry with electron rich or strained alkenes and alkynes.

"Bioorthogonal" reactive handles are reactive handles that can be used in biological systems, i.e., in aqueous media, and that are generally not reactive toward common functional groups in the biological system, so they can be used to manipulate biological compounds selectively, without interference from the biomolecule components, Bioorthogonal chemistry is well known in the art: suitable functional groups for bioorthogonal chemistry include ketones, aldehydes, hydrazides, alkoxyamines, azides, terminal alkynes, phosphines, nitrones, nitrile oxides, diazo compounds, tetrazines, tetrazoles, quadrocyclanes, alkenes, iodobenzenes, transcyclooctenes, cyclooctynes, norbomenes, cyclopropenes, vinyls, isonitriles, and cycloaddition reactants. M. F. Debets, et al., *Org. Biomol. Chem.* 2013, vol. 11, 6439. Examples include click chemistry, particularly copper-free click chemistry, which uses cycloaddition reactants like cyclooctyne that react efficiently with alkyl azides; and inverse-electron demand Diels-Alder chemistries such as tetrazines, which react with strained alkenes or alkynes like cyclopropene and trans-cyclooctene as well as strained alkynes like cyclooctynes Useful cyclooctynes include:

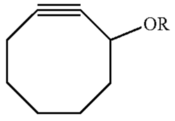
OCT

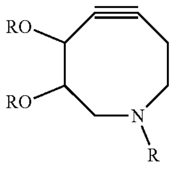
DIMAC

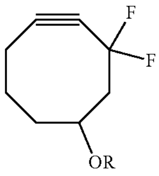
DIBO

-continued

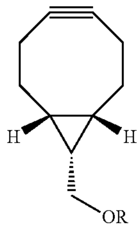

BCN

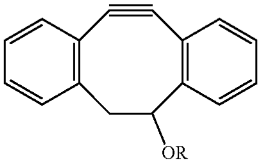

DIBO

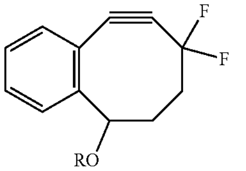

DIFBO

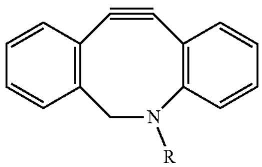

DIBAC

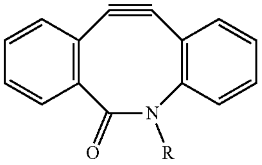

BARAC

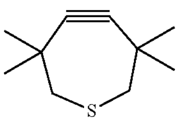

TMTH

'R' in these structures indicates where the cyclooctyne compound can be attached to a target molecule or conjugation reagent, etc. TMTH is actually a 7-membered ring, but the C—S bonds are longer than C—C bonds, so the ring strain is similar to that of a cyclooctyne. C. P. Ramil, et al., *Chem. Commun.* 2013, vol. 49, 11007-11022.

As used herein, the term 'leaving group' refers to a moiety that is readily displaced by reaction with a complementary reactant, which is often a nucleophile. In some examples herein, the leaving group is on an acyl carbon, e.g., R—C(═O)-LG, where LG is a displaceable leaving group; such acyl groups can react with a nucleophile, where the leaving group is replaced by the nucleophile. Examples of leaving groups for such acyl groups include, but are not limited to, halo, CN, azide, acyl groups such as pivaloate, alkoxyacyloxy groups such as isobutoxy-carbonyl-O, imidazole, triazole, anhydride, sulfonyl, hydrazide, sulfonylhydrazide, azobenzotriazole, pentafluorophenol, dinitrophenol, —O-benzotriazole, ethyl cyanohydroxyiminoacetate, activated alkoxy groups such as trifluoroethoxy and trichloroethoxy, and —OC(O)OR where R is a $C_{1-8}$ alkyl.

As used herein, the term "organic scaffold" refers to a stable organic molecular core to which various groups are attached. Organic scaffolds are typically substituted with at least one reactive handle, and often with an additional reactive handle and/or detectable label. An organic scaffold can be constructed of alkyl chains, aromatic rings, heteroaryl rings, heterocyclic rings, carbocyclic rings, ether and polyether chains (like PEG groups), natural and non-natural amino acids, and combinations of these, and are often assembled with amide bonds linking suitable components, for example. While an organic scaffold can be of any suitable size for its purpose, in some embodiments the organic scaffold has a molecular weight less than about 2000, and optionally less than 1500, and preferably less than about 1000.

As used herein, the term "organic linking group" or "organic linker" refers to a stable organic linker for connecting two (or more than two) chemical groups together. If not otherwise specified, the organic linking group contains up to 100 carbon atoms and up to 24 heteroatoms selected from N, O and S, and is optionally substituted with 1-3 groups selected from $C_{1-3}$ alkoxy, oxo, CN, and halo. In some embodiments, the linking group comprises up to 50 carbon atoms and up to 20 heteroatoms. In other embodiments, the organic linking group comprises up to 20 carbon atoms and up to 7 heteroatoms.

As used herein, the term "macromolecule" encompasses large molecules composed of smaller subunits. Examples of macromolecules include, but are not limited to peptides, polypeptides, proteins, nucleic acids, carbohydrates, lipids, macrocycles. A macromolecule also includes a chimeric macromolecule composed of a combination of two or more types of macromolecules, covalently linked together (e.g., a peptide linked to a nucleic acid). A macromolecule may also include a "macromolecule assembly", which is composed of non-covalent complexes of two or more macromolecules. A macromolecule assembly may be composed of the same type of macromolecule (e.g., protein-protein) or of two more different types of macromolecules (e.g., protein-DNA).

As used herein, the term "peptide" is used interchangeably with the term "polypeptide", encompassing peptides, polypeptides and proteins, and refers to a molecule comprising a chain of two or more amino acid residues joined by peptide bonds. In general terms, a peptide having more than 20-30 amino acids is commonly referred to as a polypeptide, and one having more than 50 amino acids is commonly referred to as a protein. The amino acids of the peptide are most typically L-amino acids, but may also be D-amino acids, modified amino acids, amino acid analogs, amino acid mimetics, or any combination thereof. Peptides may be naturally occurring, synthetically produced, or recombinantly expressed. Peptides may also comprise additional groups modifying the amino acid chain, for example, functional groups added via post-translational modification.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or lie), Lysine (K or Lys), Leucine (L or Leu), Methionine (M or Met), Asparagine (N or Asn), Proline (P or Pro), Glutamine (Q or Gin), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, β-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids.

As used herein, the term "solid support", "solid surface", or "substrate" refers to any solid material, including porous and non-porous materials, to which a macromolecule (e.g., peptide) can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, nylon, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, nitrocellulose, glass, gold, quartz, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polyactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, polystyrene bead, a polymer bead, a methylstyrene bead, an agarose bead, an acrylamide bead, a solid core bead, a porous bead, a paramagnetic bead, a glass bead, or a controlled pore bead. A bead may be spherical or an irregularly shaped. A bead's size may range from nanometers, e.g., 100 nm, to millimeters, e.g., 1 mm. In certain embodiments, beads range in size from about 0.2 micron to about 200 microns, or from about 0.5 micron to about 5 micron. n some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 μm in diameter. In certain embodiments, "a bead" solid support may refer to an individual bead or a plurality of beads.

As used herein, the terms "nucleic acid" and "polynucleotide" are used interchangeably and refer to a single- or double-stranded nucleic acid molecule containing deoxyribonucleotides or ribonucleotides that are linked by 3'-5' phosphodiester bonds, as well as to polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding.

As used herein, "nucleic acid sequencing" means the determination of the order of nucleotides in a nucleic acid molecule or a sample of nucleic acid molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid support and a complementary sequence to a nucleic acid molecule, a nucleic acid molecule can be hybridized to the solid support via the primer and then multiple copies can be generated in a discrete area on the solid support by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays, as reviewed by Service (*Science* 311:1544-1546, 2006).

As used herein, "analyzing" the macromolecule means to quantify, characterize, distinguish, or a combination thereof, all or a portion of the components of the macromolecule. For example, analyzing a peptide, polypeptide, or protein includes determining all or a portion of the amino acid sequence (contiguous or non-continuous) of the peptide. Analyzing a macromolecule also includes partial identification of a component of the macromolecule. For example, partial identification of amino acids in the macromolecule protein sequence can identify an amino acid in the protein as belonging to a subset of possible amino acids. Analysis typically begins with analysis of the n NTA A, and then proceeds to the next amino acid of the peptide (i.e., n-1, n-2, n-3, and so forth). This is accomplished by cleavage of the n NTAA, thereby converting the n-1 amino acid of the peptide to an N-terminal amino acid (referred to herein as the "n-1 NTAA"). Analyzing the peptide may also include determining the presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

The terminal amino acid at one end of the peptide chain that has a free amino group is referred to herein as the "N-terminal amino acid" (NTAA). The terminal amino acid at the other end of the chain that has a free carboxyl group is referred to herein as the "C-terminal amino acid" (CTAA). The amino acids making up a peptide may be numbered in order, with the peptide being "nt" amino acids in length. As used herein, NTAA is considered the $n^{th}$ amino acid (also referred to herein as the "n NTAA"). Using this nomenclature, the next amino acid is the n-1 amino acid, then the n-2 amino acid, and so on down the length of the peptide from the N-terminal end to C-terminal end. In certain embodiments, an NTAA, CTAA, or both may be modified or labeled with a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a macromolecule (e.g., protein, polypeptide, peptide), a binding agent, a set of binding agents from a binding cycle, a sample macromolecules, a set of samples, macromolecules within a compartment (e.g., droplet, bead, or separated location), macromolecules within a set of compartments, a fraction of macromolecules, a set of macromolecule fractions, a spatial region or set of spatial regions, a library of macromolecules, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error correcting barcodes. Barcodes can be used to computationally deconvolute the multiplexed sequencing data and identify sequence reads derived from an individual macromolecule, sample, library, etc. A barcode can also be used for deconvolution of a collection of macromolecules that have been distributed into small compartments for enhanced mapping. For example, rather than mapping a peptide back to the proteome, the peptide is mapped back to its originating protein molecule or protein complex.

A "sample barcode", also referred to as "sample tag" identifies from which sample a macromolecule derives.

A "spatial barcode" identifies region of a 2-D or 3-D tissue section from which a macromolecule derives. Spatial barcodes may be used for molecular pathology on tissue sections. A spatial barcode allows for multiplex sequencing of a plurality of samples or libraries from tissue section(s).

As used herein, the term "coding tag" refers to a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, *Nat. Commun* 6:7237; Lutz, 2015, Macromolecules 48:4759-4767; each of which are incorporated by reference in its entirety). A coding tag comprises an encoder sequence, which is optionally flanked by one spacer on one side or flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

As used herein, the term "encoder sequence" or "encoder barcode" refers to a nucleic acid molecule of about 2 bases to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) in length that provides identifying information for its associated binding agent. The encoder sequence may uniquely identify its associated binding agent. In certain embodiments, an encoder sequence provides identifying information for its associated binding agent and for the binding cycle in which the binding agent is used. In other embodiments, an encoder sequence is combined with a separate binding cycle-specific barcode within a coding tag. Alternatively, the encoder sequence may identify its associated binding agent as belonging to a member of a set of two or more different binding agents. In some embodiments, this level of identification is sufficient for the purposes of analysis. For example, in some embodiments involving a binding agent that binds to an amino acid, it may be sufficient to know that a peptide comprises one of two possible amino acids at a particular position, rather than definitively identify the amino acid residue at that position. In another example, a common encoder sequence is used for polyclonal antibodies, which comprises a mixture of antibodies that recognize more than one epitope of a protein target, and have varying specificities. In other embodiments, where an encoder sequence identifies a set of possible binding agents, a sequential decoding approach can be used to produce unique identification of each binding agent. This is accomplished by varying encoder sequences for a given binding agent in repeated cycles of binding (see, Gunderson et al., 2004, Genome Res. 14:870-7). The partially identifying coding tag information from each binding cycle, when combined with coding information from other cycles, produces a unique identifier for the binding agent, e.g., the particular combination of coding tags rather than an individual coding tag (or encoder sequence) provides the uniquely identifying information for the binding agent. Preferably, the encoder sequences within a library of binding agents possess the same or a similar number of bases.

As used herein the term "binding cycle specific tag", "binding cycle specific barcode", or "binding cycle specific sequence" refers to a unique sequence used to identify a library of binding agents used within a particular binding cycle. A binding cycle specific tag may comprise about 2 bases to about 8 bases (e.g., 2, 3, 4, 5, 6, 7, or 8 bases) in length. A binding cycle specific tag may be incorporated within a binding agent's coding tag as part of a spacer sequence, part of an encoder sequence, part of a UMI, or as a separate component within the coding tag.

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a recording tag or coding tag. In certain embodiments, a spacer sequence flanks an encoder sequence of a coding tag on one end or both ends. Following binding of a binding agent to a macromolecule, annealing between complementary spacer sequences on their associated coding tag and recording tag, respectively, allows transfer of binding information through a primer extension reaction or ligation to the recording tag, coding tag, or a di-tag construct. Sp' refers to spacer sequence complementary to Sp. Preferably, spacer sequences within a library of binding agents possess the same number of bases. A common (shared or identical) spacer may be used in a library of binding agents. A spacer sequence may have a "cycle specific" sequence in order to track binding agents used in a particular binding cycle. The spacer sequence (Sp) can be constant across all binding cycles, be specific for a particular class of macromolecules, or be binding cycle number specific. Macromolecule class-specific spacers permit annealing of a cognate binding agent's coding tag information present in an extended recording tag from a completed binding/extension cycle to the coding tag of another binding agent recognizing the same class of macromolecules in a subsequent binding cycle via the class-specific spacers. Only the sequential binding of correct cognate pairs results in interacting spacer elements and effective primer extension. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction. A spacer sequence may comprise a fewer number of bases than the encoder sequence within a coding tag.

As used herein, the term "recording tag" refers to a nucleic acid molecule or sequenceable polymer molecule (see. e.g., Niu et al., 2013, Nat. Chem. 5:282-292; Roy et al., 2015*, Nat. Commun.* 6:7237; Lutz, 2015, Macromolecules 48:4759-4767; each of which are incorporated by reference in its entirety) that comprises identifying information for a macromolecule to which it is associated. In certain embodiments, after a binding agent binds a macromolecule, information from a coding tag linked to a binding agent can be transferred to the recording tag associated with the macromolecule while the binding agent is bound to the macromolecule. In other embodiments, after a binding agent binds a macromolecule, information from a recording tag associated with the macromolecule can be transferred to the coding tag linked to the binding agent while the binding agent is bound to the macromolecule. A recoding tag may be directly linked to a macromolecule, linked to a macromolecule via a multifunctional linker such as the conjugation reagents herein, or associated with a macromolecule by virtue of its proximity (or co-localization) on a solid support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

The term "target compound" or "target molecule" as used herein refers to a compound that is to be used in the methods herein to form a conjugate, and particularly to be covalently attached to a linker or conjugation reagent. Typical target compounds include peptides, nucleic acids, oligosaccharides, lipopolysaccharides, and other macromolecules such as combinations of one or more of these, as well as polymers and small-molecules (up to about MW 1500). A target compound for use in the methods of the invention may comprise at least one CHD-reactive group, to enable attaching a CHD-containing linker or conjugation reagent to the target compound via methods described herein. These target compounds include peptides that contain an arginine or citrulline residue as part of the peptide backbone, as well as peptides, nucleic acids, and oligosaccharides that have been modified to contain one or more CHD-reactive groups, and small molecules that contain or have been adapted to contain at least one CHD-reactive group. Other target compounds may contain one or more reactive handles that can be used to attach the target compound to linkers and other moieties by other types of reactions disclosed herein.

The term "reactive handle" as used herein refers to a reactive functional group that can be used to attach a compound to another compound or group, e.g., to connect a target compound to a conjugation reagent, or to connect a target compound conjugate to another molecule. For example, a conjugation reagent may comprise a reactive handle that can be used to attach the conjugation reagent to a target compound. Reactive handles include functional groups that participate in click chemistry reactions (azides plus strained alkene or alkyne), amide formation reactions (carboxylic acid plus amine), inverse electron demand Diels-Alder reactions (e.g., tetrazines that react with strained alkene or alkynes), 3+2 cycloaddition reactions (e.g., nitrones plus olefins), CHDs that conjugate with arginine, and the like. Examples of reactive handles include terminal alkynes, strained alkynes, strained alkenes, tetrazines, alkyl azide, carboxylates, amines, nitrile oxides, and the like.

For each reactive handle, there is a complementary reactive handle that will react with it to form a covalent linkage. A 'complementary reactive handle' as used herein refers to one of a pair of reactive handles that react with each other. Many examples are known, see e.g., M. F. Debets, et al., *Org Biomol. Chem.* 2013, vol. 11, 6439. For example, an alkyl azide is a complementary reactive handle that can be used with a terminal alkyne: the alkyl azide and terminal alkyne can react to form a triazole ring, and the reaction can be used to connect two compounds together. Tetrazines are well known reactive handles: they can react in 'tetrazine ligation' reactions with a variety of complementary reactive handles, e.g., norbornenes, cyclooctynes, and trans-cyclooctenes:

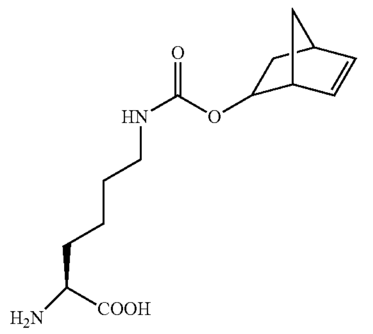

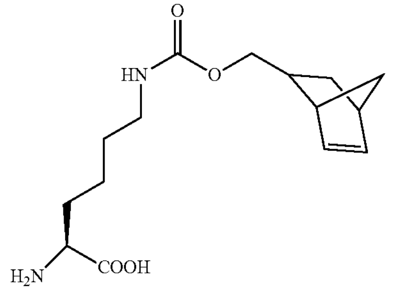

-continued

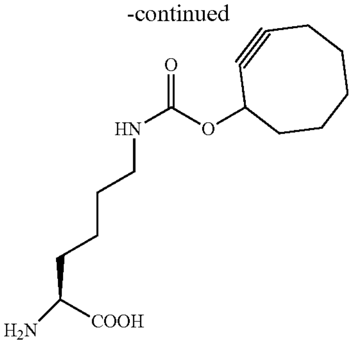

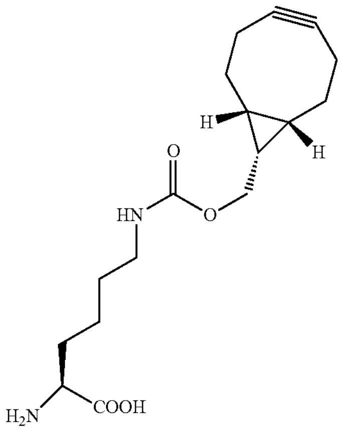

-continued

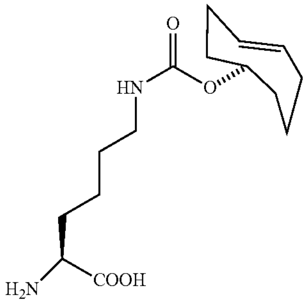

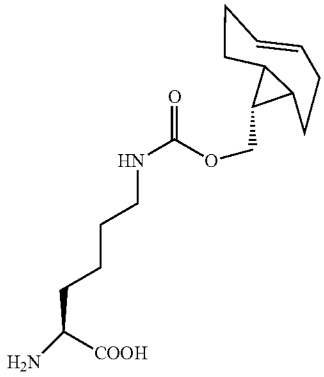

C. P Ramnil, et al., *Chem. Commun.* 2013, vol. 49, 11007-11022.

Another example of complementary reactive handles is a CHD group and a CHD-reactive group, which can react as described herein to form a stable linkage. A conjugation reagent that comprises a first reactive handle can be covalently attached to a target compound that comprises a complementary reactive handle that is complementary to the first reactive handle.

The compounds and substructures described herein include stable tautomers of the depicted structure as well as the structure depicted. As a non-limiting example, substructure (A) attached to a nitrogen atom of the target T can exist in at least the following tautomeric forms:

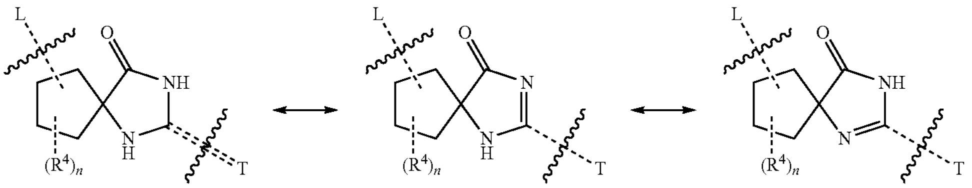

(A) (A′) (A″)

and each of these tautomeric forms (A), (A') and (A") is included with the depiction of substructure (A) alone, unless expressly indicated otherwise.

The following enumerated embodiments are representative of the invention:

1. A method to attach a conjugation reagent to a target molecule, wherein:
   the conjugation reagent comprises a 1,2-cyclohexanedione (CHD) group; and
   the target molecule comprises a CHD-reactive group;
   wherein the method comprises contacting the conjugation reagent with the target molecule under reaction conditions that cause the CHD-reactive group to react irreversibly with the CHD group to form a modified target molecule having a covalent linkage connecting the conjugation reagent and the target molecule,
   wherein the reaction conditions comprise an aqueous medium at a pH less than 13. In a preferred embodiment, the pH is below 10.
2. The method of embodiment 1, wherein the pH of the aqueous medium is below 12 and the medium comprises a buffer, optionally at least 0.1 M buffer concentration, and preferably 0.5 M or higher buffer concentration. For this embodiment, suitable pH can be below 10, or between 6 and 9, and the suitable buffer concentration can be about 1-2 M. Suitable ionic strength of the medium can be from about 0.1 M to about 4 M. and higher.
3. The method of embodiment 1 or 2, wherein the CHD-reactive group comprises an acylated $NH_2$.
4. The method of embodiment 3, wherein the acylated $NH_2$ is part of a guanidine, amidine, thiourea, or urea group.
5. The method of any of embodiments 1-4, wherein the CHD-reactive group is a guanidine.
6. The method of embodiment 5, wherein the CHD-reactive group is a guanidine group of an arginine residue.
7. The method of embodiments 1-6, wherein the conjugation reagent comprises at least one additional reactive handle that is stable under reaction conditions that cause the CHD-reactive group to react irreversibly with the CHD group. Suitable reactive handles for this embodiment include tetrazine, azide, cyclopropene, cyclooctyne, trans-cyclooctene, alkyne, and the like.
8. The method of embodiment 7, wherein the at least one additional reactive handle is selected from a conjugation partner, a click chemistry reactant, a base cleavable linker, a base removable protecting group, and a bioorthogonal reactive handle.
9. The method of embodiment 8, wherein one of the at least one additional reactive handle is a bioorthogonal reactive handle.
10. The method of embodiment 8 or 9, wherein the bioorthogonal reactive handle comprises a group selected from ketones, aldehydes, hydrazides, alkoxyamines, azides, terminal alkynes, phosphines, nitrones, nitrile oxides, diazo compounds, tetrazines, tetrazoles, quadrocyclanes, alkenes, iodobenzenes, transcyclooctenes, cyclooctynes, norbornenes, cyclopropenes, vinyls, isonitriles, and cycloaddition reactants.
11. The method of any one of embodiments 8-10, wherein the conjugation reagent comprises two additional reactive handles.
12. The method of any one of embodiments 3-11, wherein the covalent linkage connecting the conjugation reagent and the target molecule comprises the following substructure (A):

(A)

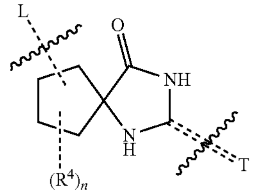

or a tautomer thereof, wherein:
   the dashed bond to L connects the substructure (A) to the conjugation reagent;
   the dashed bond to T connects the substructure (A) to the target molecule;
   $R^4$ is an optional substituent on the cyclopentyl ring, and each $R^4$ is independently selected from $C_{1-2}$ alkyl, $C_{1-2}$ alkoxy, $C_{1-2}$ haloalkyl, —COOR, $SO_3R$, halo, hydroxy, and $CONR_2$;
   each R is independently H or $C_{1-4}$ alkyl optionally substituted with 1-3 groups selected from halo, OH, and $C_{1-2}$ alkoxy; and
   n is 0, 1, 2 or 3.
13. The method of any one of the preceding embodiments, wherein the target molecule comprises two or more CHD-reactive group. In some such embodiments, the target molecule is a polypeptide that has optionally been treated to cap cysteine residues and/or lysine residues.
14. The method of any one of the preceding embodiments, wherein the target molecule comprises a peptide, nucleic acid, oligosaccharide, or small molecule, or a combination of two or more of these.
15. The method of embodiment 14, wherein the target molecule comprises a peptide.
16. The method of embodiment 15, wherein the peptide is treated to cap cysteine residues that may be present before the peptide is contacted with the conjugation reagent.
17. The method of any one of embodiments 14-16, wherein the peptide is treated to reduce any disulfide bonds before the peptide is contacted with the conjugation reagent.
18. The method of any one of embodiments 14-17, wherein the peptide is treated to cap any free thiol groups before the peptide is contacted with the conjugation reagent.
19. The method of embodiment 18, wherein the peptide is treated with TCEP and iodoacetamide to cap any free thiol groups.
20. The method of any one of embodiments 14-19, wherein the peptide is treated to block any lysine residues before it is contacted with the conjugation reagent.
21. The method of embodiment 20, wherein the peptide is treated with NHS-BIB (N-hydroxysuccinimide bromoisobutyrate) or with desthiobiotin-NHS (DTB-NHS) to block any lysine residues before the peptide is contacted with the conjugation reagent, 22. The method of any of embodiments 1-21, wherein the reaction conditions comprise an aqueous medium that includes up to 25% of an organic co-solvent.
23. The method of embodiment 22, wherein the aqueous medium is at a pH between about 6 and 10.
24. The method of embodiment 23, wherein the aqueous medium comprises 1-20% of organic co-solvent, and wherein the organic co-solvent comprises DMSO, dioxane, THF, ethanol, isopropanol, DME, diglyme, DMF, DMA, NMP, acetonitrile, cyrene, 2-methyl-THF, 1,3-dimethylpyridone, limonene, or a mixture of two or more of these,
25. The method of any one of embodiments 1-24, wherein the reaction conditions comprise a temperature between about 20° C. and 120° C. Typically, the reaction temperature is above 50° C., often it is between 5° and 100° C., and in some embodiments the reaction temperature is between 60 and 90° C.
26. The method of any one of embodiments 1-25, wherein the reaction conditions comprise a reaction time between 0.1 and 12 hours.
27. The method of any one of embodiments 1-26, wherein the aqueous medium comprises a buffer. Typically, the buffer concentration is at least 0.5M, and in some embodiments the buffer concentration is about 1-2M. Suitable ionic strength of the medium can be from about 0.1 M to about 4 M, and higher,
28. The method of embodiment 27, wherein the buffer is selected from phosphate buffers, pyrophosphate buffers, carbonate buffers, bicarbonate buffers, borate buffers, acetate buffers, citrate buffers, HEPES, MOPS, TRIS, CAPS, SSC, PIPES, PBS, TAPS, DAP, CBC, imidazole, and mixtures thereof.
29. The method of any one of embodiments 1-28, wherein at least 25% of the target molecules present react to form a modified target molecule.
30. The method of any one of embodiments 1-29, wherein the method converts at least about 40% of the target molecule into a modified target molecule having a covalent linkage connecting the target molecule and the conjugation reagent. Preferably, the method converts at least 60% or at least 75% of the target molecule to a modified target molecule.
31. The method of any one of embodiments 1-30, wherein the conjugation reagent further comprises a detectable label or marker.
32. The method of embodiment 31, wherein the detectable label or marker comprises a fluorogenic moiety.
33. The method of embodiment 31, wherein the detectable label or marker comprises a fluorophore.
34. The method of embodiment 31, wherein the detectable label or marker comprises a fluorescence quencher.
35. The method of any one of embodiments 7-34, wherein the conjugation reagent comprises an additional reactive handle, and the method comprises an additional step of using the additional reactive handle on the conjugation reagent of the modified target molecule having a covalent linkage connecting the target molecule and the conjugation reagent, to form a covalent linkage between the conjugation reagent and a second target molecule having a reactive handle complementary to the additional reactive handle, to form a target molecule—conjugation reagent—second target molecule conjugate.
36. The method of embodiment 35, wherein the second target molecule comprises a nucleic acid. In some of these embodiments, the target molecule is a peptide, and the product of the method comprises a peptide—conjugation reagent—nucleic acid conjugate,
37. The method of any one of embodiments 32-36, wherein the fluorescence of the reaction mixture is modified in a detectable way by the reaction of the conjugation reagent with the target molecule, or by the reaction of the target molecule-conjugation reagent conjugate with a second target molecule.
38. The method of embodiment 32, wherein the fluorogenic moiety is used to monitor the progress of the reaction that connects the target molecule-conjugation reagent conjugate to the second target molecule.
39. A method to attach a conjugation reagent to a target molecule, wherein:

the conjugation reagent comprises a 1,2-cyclohexanedione (CID) group and a detectable label; and the target molecule comprises a CHD-reactive group;

wherein the method comprises contacting the conjugation reagent with the target molecule under reaction conditions that cause the CHD-reactive group to react irreversibly with the CHD group to form a modified target molecule having a covalent linkage connecting the target molecule and the conjugation reagent.

40. The method of embodiment 39, wherein the reaction conditions that cause the CHD-reactive group to react irreversibly with the CHD group comprise a pH less than about 13. Typically, the pH is less than 12, and preferably the pH is between 6 and 10. The reaction conditions may comprise use of an aqueous medium and often a buffer, typically at a concentration of at least 0.5M, such as about 1-2M.
41. The method of embodiment 39 or 40, wherein the detectable label comprises a fluorogenic moiety.
42. The method of any one of embodiments 39-42, wherein the CHD-reactive group comprises an acylated $NH_2$.
43. The method of embodiment 42, wherein the acylated $NH_2$ is part of a guanidine, amidine, thiourea, or urea group.
44, The method of embodiment 39, wherein contacting the conjugation reagent with the target molecule occur in an aqueous medium having a pH below 12, wherein the aqueous medium comprises a buffer having at least 0.1 M ionic strength.
45. The method of embodiment 39, wherein the CHD-reactive group is a guanidine group of an arginine residue.
46. The method of any one of embodiments 39-45, wherein the conjugation reagent comprises an additional reactive handle. Suitable reactive handles for this embodiment include tetrazine, azide, cyclopropene, cyclooctyne, trans-cyclooctene, alkyne, and the like.
47. A conjugation reagent, which comprises a cyclohexan-1,2-dione and a base-sensitive reactive handle.
48. The conjugation reagent of embodiment 47, wherein the reactive handle is a bioorthogonal reactive handle.
49. The conjugation reagent of embodiment 47, wherein the base-sensitive reactive handle comprises an ester, thioester, nitrile, alkylating agent, tetrazine, phosphate ester, or phospholipid.
50. The conjugation reagent of embodiment 47, wherein the conjugation reagent comprises an additional reactive handle. Suitable reactive handles for this embodiment include tetrazine, azide, cyclopropene, cyclooctyne, trans-cyclooctene, alkyne, and the like.
51. The conjugation reagent of any one of embodiments 47-50, which comprises a detectable label.

52. The conjugation reagent of embodiment 51, wherein the detectable label comprises a fluorogenic moiety.
53. A multifunctional conjugation reagent, which comprises a cyclohexan-1,2-dione group (CHD), a detectable label, and an additional reactive handle. Suitable reactive handles for this embodiment include tetrazine, azide, cyclopropene, cyclooctyne, trans-cyclooctene, alkyne, and the like.
54. The multifunctional conjugation reagent of embodiment 53, wherein the additional reactive handle is a bioorthogonal reactive handle,
55. The multifunctional conjugation reagent of embodiment 53 or 54, wherein the detectable label comprises a fluorogenic moiety,
56. The multifunctional conjugation reagent of embodiment 54, wherein the bioorthogonal reactive handle comprises a group selected from ketones, aldehydes, hydrazides, alkoxyamines, azides, terminal alkynes, phosphines, nitrones, nitrile oxides, diazo compounds, tetrazines, tetrazoles, quadrocyclanes, alkenes, iodobenzenes, transcyclooctenes, cyclooctynes, norbornenes, cyclopropenes, vinyls, isonitriles, and cycloaddition reactants.
57. The multifunctional conjugation reagent of embodiment 56, wherein the cycloaddition reactant comprises an alkyl azide, a cyclopropene, a trans-cyclooctene, a strained cyclic alkyne, a terminal alkyne, or a 1,2,4,5-tetrazine.
58. The multifunctional conjugation reagent of embodiment 53, wherein the reagent is of Formula (I):

(I)

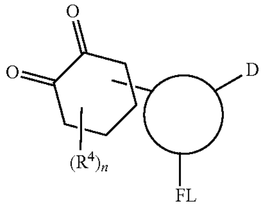

wherein:
the circle represents an organic scaffold;
each $R^4$ is independently $C_{1-2}$ alkyl, $C_{1-2}$ haloalkyl, $C_{1-2}$ alkoxy, COOR, —$SO_3R$, or $C(O)NR_2$;
each R is independently H or $C_{1-2}$ alkyl; and
n is 0, 1, 2 or 3;
D is a bioorthogonal reactive group; and
FL is a detectable label.
59. The multifunctional conjugation reagent of embodiment 53, which is a compound of Formula (IA):

(IA)

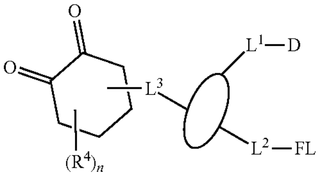

wherein:
$L^1$ is an organic linking group;
$L^2$ is an organic linking group;
$L^3$ is an organic linking group;
the oval represents an organic scaffold;
each $R^4$ is independently $C_{1-2}$ alkyl, $C_{1-2}$haloalkyl, $C_{1-2}$ alkoxy, COOR, —$SO_3R$, or $C(O)NR_2$;
each R is independently H or $C_{1-2}$ alkyl; and
n is 0, 1, 2 or 3;
D represents a bioorthogonal reactive handle; and
FL is a detectable label or fluorogenic moiety
60. The multifunctional conjugation reagent of embodiment 58 or 59, wherein D comprises a tetrazine.
61. The multifunctional conjugation reagent of embodiment 53, wherein the detectable label comprises a fluorophore.
62. The multifunctional conjugation reagent of embodiment 53, wherein the detectable label comprises a fluorescence quencher.
63. The multifunctional conjugation reagent of embodiment 55, which is of the formula (II):

(II)

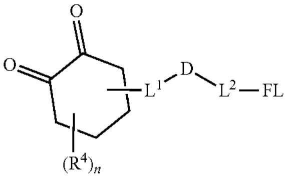

wherein:
$L^1$ is an organic linker;
D is an inverse diene;
$L^2$ is an organic linker;
FL is a fluorogenic moiety;
each $R^4$ is independently $C_{1-2}$ alkyl, $C_{1-2}$ haloalkyl, $C_{1-2}$ alkoxy, COOR, —$SO_3R$, or $C(O)NR_2$;
each R is independently H or $C_{1-2}$ alkyl; and
n is 0, 1, 2 or 3.
64. The multifunctional conjugation reagent of embodiment 63, wherein D comprises a 1,2,4,5-tetrazine ring.
65. The multifunctional conjugation reagent of embodiment 64, wherein the reagent is of the formula:

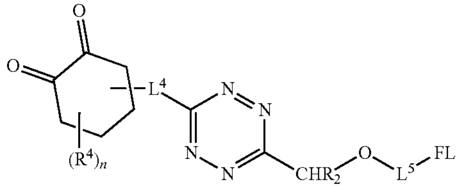

wherein:
$L^4$ is an organic linker;
$L^5$ is an organic linker; and
$R^2$ is H or $C_{1-4}$ alkyl;
each $R^4$ is independently $C_{1-2}$ alkyl, $C_{1-2}$haloalkyl, $C_{1-2}$ alkoxy, COOR, —SOR, or $C(O)NR_2$;
each R is independently H or $C_{1-2}$ alkyl; and
n is 0, 1, 2 or 3.
66. The multifunctional conjugation reagent of embodiment 65, wherein La and $L^3$ are each an organic linking group containing up to 100 carbon atoms and up to 24 heteroatoms selected from N, O and S, and optionally substituted with 1-3 groups selected from $C_{1-3}$ alkoxy, oxo, CN, and halo. In some embodiments, the linking group comprises up to 50 carbon atoms and up to 20 heteroatoms, or up to 20 carbon atoms and up to 7 heteroatoms.

67. The multifunctional conjugation reagent of embodiment 65 or 66, which is of the formula

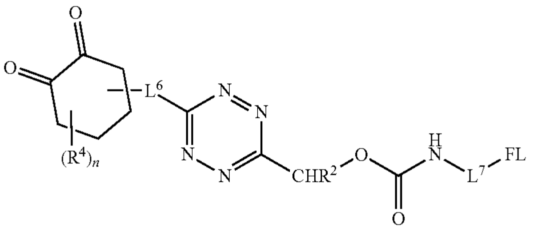

wherein $L^6$ and $L^7$ each represent an organic linking group containing up to 40 carbon atoms and up to 15 heteroatoms selected from N, O and S;

$R^2$ is FH or $C_{1-4}$ alkyl;

each $R^4$ is independently $C_{1-2}$ alkyl, $C_{1-2}$ haloalkyl, $C_{1-2}$ alkoxy, COOR, —SOR, or $C(O)NR_2$;

each R is independently H or Ct-2 alkyl; and n is 0, 1, 2, or 3.

68. A method to conjugate a peptide comprising arginine with a nucleic acid, which comprises contacting the peptide with a multifunctional conjugation reagent of embodiment 53. The method produces a peptide-multifunctional conjugation reagent conjugate, which comprises an additional reactive handle. In some embodiments, the peptide and the multifunctional conjugation reagent are contacted in an aqueous medium, optionally at a pH between 6 and 10, and optionally the medium includes a buffer at a concentration of at least 0.5M. Typically, the aqueous medium for this step is at a temperature between about 60 and 90° C. Optionally, the method comprises an additional step of contacting the peptide—multifunctional conjugation reagent conjugate with a nucleic acid that is linked to a complementary reactive handle capable of reacting with the additional reactive handle of the conjugate, and the method can thereby form a peptide—multifunctional conjugation reagent—nucleic acid conjugate.

69. A compound of the formula:

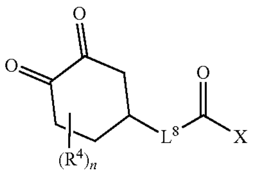

wherein X is OR, OM, a leaving group, or $NR_2$, $L^8$ is an organic linker;

each $R^4$ is independently $C_{1-2}$ alkyl, $C_{1-2}$ haloalkyl, $C_{1-2}$ alkoxy, COOR, —$SO_3R$, or $C(O)NR_2$;

each R is independently H, $(PEG)_m$, or $C_{1-8}$ alkyl optionally substituted with up to three groups selected from halo, $C_{1-2}$ alkyl, $C_{1-2}$ haloalkyl, $C_{1-2}$ alkoxy, hydroxy, amino, COOH, carbonyl (oxo), a detectable label, and a reactive handle;

or two R groups on one N can be taken together to form a 4-8 membered ring optionally containing an additional one or two heteroatoms selected from N, O and S as ring members and optionally substituted with one or two groups selected from halo, $C_{1-2}$ alkyl, $C_{1-2}$ haloalkyl, $C_{1-2}$ alkoxy, hydroxy, carbonyl (oxo), a detectable label, and a reactive handle;

PEG is an ethylene glycol monomer, and m is 1-20;

n is 0, 1, 2, or 3; and

M is a cationic counterion.

Suitable leaving groups for this embodiment include halogen (F, Cl, Br, I), imidazole, pyrazole, benzotriazole, —O-benzotriazole, O-succinimide, triazole, azide, anhydride, —OC(O)—$C_{1-6}$alkyl, —OC(O)O—$C_{1-6}$alkyl, sulfonyl, hydrazide, and sulfonylhydrazide.

Suitable cationic counterions include lithium, sodium, potassium, ammonium, tetra($C_{1-6}$alkyl)ammonium, magnesium, calcium, and the like.

70. The compound of embodiment 69, which is of the formula:

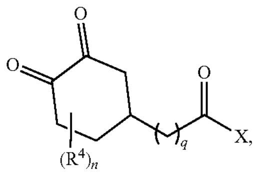

q is an integer from 0 to 10;

or a salt thereof

71. The compound of embodiment 70, which is of the formula:

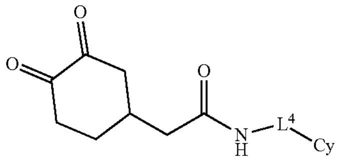

wherein:

$L^4$ is an organic linker, and

Cy is a reactive handle

72. The compound of embodiment 71, wherein the reactive handle is selected from an electron-deficient diene, an activated dienophile, and a 1,3-dipole.

73. The compound of embodiment 71 or 72, wherein the reactive handle is an azide group, a tetrazine ring, a strained alkene, or an alkyne.

74. The compound of any one of embodiments 71-73, which further comprises a detectable label covalently attached to the linker $L^4$.

75. The compound of any one of embodiments 71-74, which further comprises a high affinity non-covalent binding group covalently attached to the linker.

76. The compound of embodiment 75, wherein the high affinity non-covalent binding group is covalently attached to the organic linker through a cleavable linkage.

77. The compound of any one of embodiments 75-76, wherein the high affinity non-covalent binding group is covalently attached to the organic linker through a cleavable linkage that can be cleaved by UV irradiation, by visible light irradiation, or by an enzyme such as a peptidase.

78. A kit comprising a CHD compound according to any one of embodiments 47-77 and at least one nucleic acid conjugate that comprises a bioorthogonal reactive group. In some embodiments, the bioorthogonal reactive group is complementary to the base-sensitive reactive handle in the CHD compound.
79. The kit of embodiment 78, further comprising a buffer.
80. A peptide-nucleic acid conjugate wherein the linkage connecting the peptide with the nucleic acid comprises a group of the substructure (A):

(B)

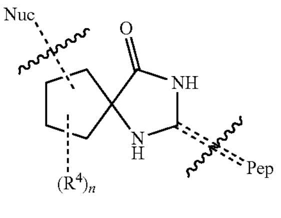

or a tautomer thereof, wherein:

the dashed bond to Nuc represents where substructure (B) is linked to the nucleic acid;

the dashed bond to T represents where substructure (B) is attached to the polypeptide;

each $R^4$ is independently $C_{1-2}$ alkyl, $C_{1-2}$ haloalkyl, $C_{1-2}$ alkoxy, COOR, —$SO_3R$, or $C(O)NR_2$;

each R is independently H or $C_{1-4}$ alkyl optionally substituted with up to three groups selected from halo, $C_{1-2}$ alkyl, $C_{1-2}$ haloalkyl, $C_{1-2}$ alkoxy, hydroxy, and carbonyl (oxo); or two R groups on one N can be taken together to form a 4-8 membered ring optionally containing an additional one or two heteroatoms selected from N, O and S as ring members and optionally substituted with one or two groups selected from halo, $C_{1-2}$alkyl, $C_{1-2}$ haloalkyl, $C_{1-2}$ alkoxy, hydroxy, and carbonyl (oxo); and n is 0, 1, 2, or 3.

81. The peptide-nucleic acid conjugate of embodiment 80, wherein the peptide is attached to a solid support.
82. The peptide-nucleic acid conjugate of embodiment 80 or 81, wherein the linkage comprises substructure (B'):

(B')

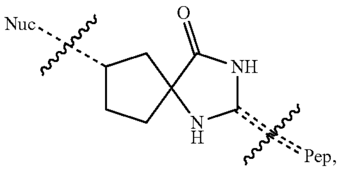

83. A method to attach a CHD moiety to an amine-containing compound of the formula R—NH—R', wherein the method comprises:

coupling the amine of the amine-containing compound with a CH D compound of the formula:

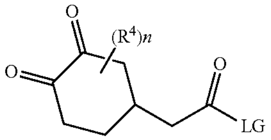

wherein LG is —OH or a leaving group, each $R^4$ is independently $C_{1-2}$ alkyl, $C_{1-2}$ haloalkyl, $C_{1-2}$ alkoxy, COOR, —$SO_3R$, or $C(O)NR_2$;

each R is independently H or $C_{1-2}$ alkyl; and n is 0, 1, 2 or 3;

to form an amide of the formula

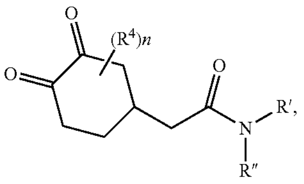

wherein R' is H or optionally substituted $C_1$-$C_6$ alkyl, and R" is H or $C_{1-4}$ alkyl optionally substituted with up to three groups selected from halo, $C_{1-2}$ alkyl, $C_{1-2}$haloalkyl, $C_{1-2}$ alkoxy, hydroxy, carbonyl (oxo), a bioorthogonal reactive handle, and a detectable label;

or R' and R" taken together with the nitrogen they are both connected to can be taken together to form a 4-8 membered ring optionally containing an additional one or two heteroatoms selected from N, O and S as ring members and optionally substituted with one or two groups selected from halo, $C_{1-2}$ alkyl, $C_{1-2}$haloalkyl, $C_{1-2}$ alkoxy, hydroxy, carbonyl (oxo), a bioorthogonal reactive handle, and a detectable label.

Suitable leaving groups for this embodiment include halogen (F, Cl, Br, I), imidazole, pyrazole, benzotriazole, —O-benzotriazole, O-succinimide, triazole, azide, anhydride, —OC(O)—$C_{1-6}$alkyl, —OC(O)O—$C_{1-6}$alkyl, sulfonyl, hydrazide, and sulfonylhydrazide. Suitable cationic counterions include lithium, sodium, potassium, ammonium, tetra($C_{1-6}$alkyl)ammonium, magnesium, calcium, and the like.

84. The method of embodiment 83, wherein R' is H.
85. The method of embodiment 83, wherein LG represents —OH or a leaving group selected from halo, imidazole, triazole, azide, anhydride, sulfonyl, hydrazide, sulfonylhydrazide, azobenzotriazole, pentafluorophenol, dinitrophenol, —O-benzotriazole, ethyl cyanohydroxyiminoacetate, an activated alkoxy, pivaloyl, —OC(O)OR* where R* is a $C_{1-8}$ alkyl optionally substituted with phenyl or up to three groups selected from halo, hydroxy, $C_{1-2}$ alkoxy, and CN.
86. A linking reagent comprising a CHD and a reactive handle comprising a group selected from azide, tetrazine, cyclopropene, trans-cyclooctene, terminal alkyne, and cyclooctyne, wherein the CHD and reactive handle are connected by a hydrophilic linking group comprising a polar group such as polyethylene glycol (PEG) having e.g. 2-20 PEG groups, or a 4-20 atom hydrocarbon chain interrupted by one or more polar linkages such as NR, O, $SO_2$, C(O), and C(O)NR, where each R is independently H or $C_{1-4}$ alkyl.
87. The linking reagent of embodiment 86, which is of the formula:

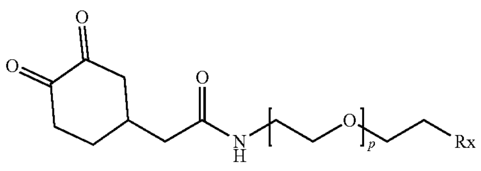

wherein Rx is a reactive handle that comprises a tetrazine or an azide; and p is an integer from 1 to 100.

88. The linking reagent of embodiment 87, wherein p is an integer from 2 to 50.

89. The linking reagent of embodiment 87, wherein Rx is an azide.

90. The linking reagent of embodiment 87, wherein Rx is a substituted tetrazine.

91. A method to attach a cyclohexanedione moiety to a target compound of the formula R'—COOH, R'C(O)-LG, or R'—NCO, comprising:

coupling the target compound with a CHD compound of the formula:

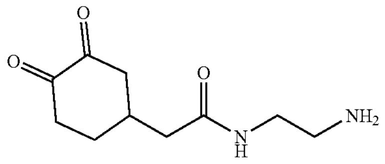 [SMILES: NCCNC(=O)CC1CCC(=O)C(=O)C1]

to form a product of the formula

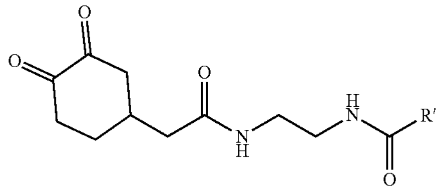

or

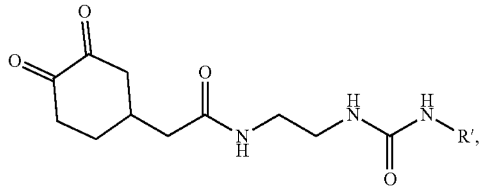

wherein R' comprises an organic scaffold optionally comprising a reactive handle that is stable under the conditions used to couple the target compound with the CHD compound, and LG is a leaving group. Suitable leaving groups for this embodiment include halogen (F, Cl, Br, I), imidazole, pyrazole, benzotriazole, —O-benzotriazole, O-succinimide, triazole, azide, anhydride, —OC(O)—$C_{1-6}$alkyl, —OC(O)O—$C_{1-6}$alkyl, sulfonyl, hydrazide, and sulfonylhydrazide.

92. The method of embodiment 91, wherein R' comprises a detectable label, a reactive handle, or both a detectable label and a reactive handle.

93. A method to attach a modifier to a target molecule, wherein:

the target molecule comprises a 1,2-cyclohexanedione (CHD) group; and the modifier comprises a CHD-reactive group;

wherein the method comprises contacting the modifier with the target molecule under reaction conditions that cause the CHD-reactive group to react irreversibly with the CHD group to form a modified target molecule having a covalent linkage connecting the modifier to the target molecule, wherein the reaction conditions comprise an aqueous medium at a pH less than 13.

94. A method to attach a modifier to a target molecule, wherein:

the modifier comprises a 1,2-cyclohexanedione (CHD) group; and the target molecule comprises a CHD-reactive group;

wherein the method comprises contacting the modifier with the target molecule under reaction conditions that cause the CHD-reactive group to react irreversibly with the CHD group to form a modified target molecule having a covalent linkage connecting the conjugation reagent and the target molecule, wherein the reaction conditions comprise an aqueous medium at a pH less than 13. Suitable modifiers for use in this method include the conjugation reagents of embodiments 47-52 and the multifunctional conjugation reagents of embodiments 53-67.

95. The method of embodiment 93 or 94, wherein the pH of the aqueous medium is below 12 and the medium comprises a buffer, optionally at least 0.1M buffer concentration, and preferably 0.5M concentration or higher. Optionally, the buffer concentration is about 1-2M. In these embodiments, the pH is typically between 6 and 10, and the reaction temperature is typically between about 60° C. and 90° C.

96. The method of embodiment 95, wherein the CHD-reactive group comprises an acylated $NH_2$.

97. The method of embodiment 96, wherein the acylated $NH_2$ is part of a guanidine, amidine, thiourea, or urea group.

98. The method of any of embodiments 93-97, wherein the CHD-reactive group is a guanidine.

99. The method of embodiment 98, wherein the CHD-reactive group is a guanidine group of an arginine residue.

100. The method of any of embodiments 93-99, wherein the reaction conditions comprise an aqueous medium that includes up to 25% of an organic co-solvent.

101. The method of embodiment 100, wherein the aqueous medium is at a pH between about 6 and 10.

102. The method of embodiment 101, wherein the aqueous medium comprises 1-20% of organic co-solvent, and wherein the organic co-solvent comprises DMSO, dioxane, THF, ethanol, isopropanol, DME, diglyme, DMF, DMA, NMP, acetonitrile, cyrene, 2-methyl-THF, 1,3-dimethylpyridone, limonene, or a mixture of two or more of these.

103. The method of any one of embodiments 93-102, wherein the reaction conditions comprise a temperature between about 20° C. and 120° C.

104. The method of any one of embodiments 93-103, wherein the reaction conditions comprise a reaction time between 0.1 and 12 hours.

105. The method of any one of embodiments 93-104, wherein the aqueous medium comprises a buffer.

106. The method of embodiment 105, wherein the buffer is selected from phosphate buffers, pyrophosphate buffers, carbonate buffers, bicarbonate buffers, borate buffers, acetate buffers, citrate buffers, HEPES, MOPS, TRIS, CAPS, SSC, PIPES, PBS, TAPS, DAP, CBC, imidazole, and mixtures thereof, 107. The method of any one of embodiments 93-106, wherein at least 25% of the target molecules present react to form a modified target molecule.

108. The method of any one of embodiments 93-106, wherein the method converts at least about 40% of the target molecule into a modified target molecule having a covalent linkage connecting the target molecule and the modifier. Preferably, the method converts at least 60% or at least 75% of the target molecule to a modified target molecule.

109. The method of any one of embodiments 93-108, wherein the modifier comprises a detectable label or marker.

110. The method of embodiment 109, wherein the detectable label or marker comprises a fluorogenic moiety.

111. A composition comprising a peptide-polynucleotide conjugate, wherein a covalent linkage connecting a peptide and a polynucleotide of the peptide-polynucleotide conjugate comprises the following substructure (D):

(D)

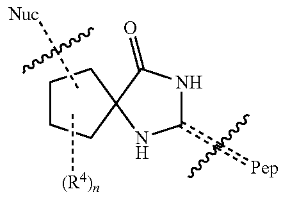

or a tautomer thereof, wherein:

the dashed bond to Nuc represents where substructure (D) is linked to the polynucleotide;

the dashed bond to Pep represents where substructure (D) is linked to the peptide;

$R^4$ is an optional substituent on the cyclopentyl ring, and each $R^4$ is independently selected from the group consisting of C1-2 alkyl, C1-2 alkoxy, C1-2 haloalkyl, —COOR, $SO_3R$, halo, hydroxy, and $C(O)NR_2$;

each R is independently H or $C_{1-4}$ alkyl optionally substituted with up to three groups selected from the group consisting of halo, OH, C1-2 alkyl, C1-2 haloalkyl, C1-2 alkoxy, and carbonyl (oxo), or two R groups on one N are forming a 4-8 membered ring optionally containing an additional one or two heteroatoms selected from N, O and S as ring members and optionally substituted with one or two groups selected from halo, C1-2 alkyl, C1-2 haloalkyl, C1-2 alkoxy, hydroxy, and carbonyl (oxo); and n is 0, 1, 2 or 3.

112. The composition of embodiment 111, further comprising a solid support, wherein the peptide is attached to the solid support via a linker.

113. The composition of any one of embodiments 111-112, wherein an N-terminal amino acid (NTAA) of the peptide forms a covalent bond with the linker.

114. The composition of any one of embodiments 111-113, wherein the covalent linkage is attached to an arginine residue of the peptide.

115. The composition of embodiment 113, wherein the covalent bond between the NTAA and the linker is an amide bond.

116. The composition ofany one of embodiments 112-115, wherein the peptide is covalently attached to the solid support and the linker is a cleavable linker.

117. The composition of any one of embodiments 111-116, wherein the polynucleotide comprises a barcode.

118. The composition of any one of embodiments 111-117, wherein the covalent linkage comprises substructure (D'):

(D')

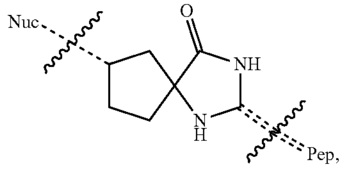

119. A method of attaching a peptide comprising at least one arginine residue to a polynucleotide, the method comprising the steps of.

(a) contacting the peptide with a conjugation reagent comprising a first reactive handle and a 1,2-cyclohexanedione (CHD) group under reaction conditions that allows the least one arginine residue to react irreversibly with the CHD group, wherein the reaction conditions comprise an aqueous medium at a pH of about 13 or less, and the first reactive handle is attached or is configured to be attached to the polynucleotide or to a second reactive handle attached to the polynucleotide;

(b) optionally, attaching the first reactive handle to the polynucleotide or to the second reactive handle attached to the polynucleotide.

120. The method of embodiment 119, further comprising the following steps: (i) before contacting the peptide with the conjugation reagent, contacting the peptide with a site-specific protease that is configured to cleave the peptide at arginine residue(s), thereby producing at least one fragmented peptide having a single arginine residue at its carboxyl terminus; and (ii) immobilizing the at least one fragmented peptide to a solid support via a linker, wherein the at least one fragmented peptide is contacted with the conjugation reagent.

121. The method of embodiment 120, wherein immobilizing the at least one fragmented peptide to the solid support comprises forming a covalent bond between an N-terminal amino acid (NTAA) of the at least one fragmented peptide and the linker.

122. The method of any one of embodiments 119-121, wherein the site-specific protease is trypsin and the lysine residue(s) of the peptide is or are blocked to prevent a trypsin cleavage to occur at the lysine residue(s) of the peptide.

123. The method of any one of embodiments 120-122, wherein the covalent bond between the NTAA and the linker is an amide bond.

124. The method of any one of embodiments 120-123, wherein immobilizing comprises covalently attaching the peptide to the solid support via a cleavable linker.

125. The method of embodiment 124, further comprising releasing the peptide attached to the polynucleotide from the solid support by breaking the covalent bond between the NTAA and the linker.

126. The method of any one of embodiments 120-125, wherein the step (ii) is performed before the step (a).

127. The method of any one of embodiments 120-125, wherein the step (ii) is performed after the step (a).

128. The method of any one of embodiments 120-127, wherein the pH of the aqueous medium in the step (c) is below or equal 12.5.

129. The method of any one of embodiments 120-128, which does not comprise a step of isolating or purifying the peptide.

130. A method of analyzing a peptide analyte comprising at least one arginine residue, the method comprising the steps of:

(a) providing a conjugate of the peptide analyte and a recording tag, the conjugate attached to a solid support, wherein the recording tag comprises a polynucleotide that is conjugated to the peptide analyte according to the following steps:

(i) contacting the peptide analyte with a conjugation reagent comprising a first reactive handle and a 1,2-cyclohexanedione (CHD) group under reaction conditions that allows the least one arginine residue to react irreversibly with the CHD group, wherein the reaction conditions comprise an aqueous medium at a pH of about 13 or less, and the first reactive handle is attached or is configured to be attached to the polynucleotide or to a second reactive handle attached to the polynucleotide; and (ii) optionally, attaching the first reactive handle to the polynucleotide or to the second reactive handle attached to the polynucleotide;

(b) contacting the peptide analyte of the conjugate with a binding agent capable of binding to the peptide analyte, wherein the binding agent comprises a coding tag that comprises identifying information regarding the binding agent;

(c) transferring the identifying information from the coding tag to the recording tag to generate an extended recording tag, and (d) analyzing the extended recording tag, thereby analyzing the peptide analyte.

The conjugate can be attached to the solid support by various means, such as attached via peptide, via recording tag, via a linker, via hybridization of the recording tag with a capture DNA attached to the solid support. Additional details regarding this and other aspects of the method can be found in US 20190143982 A1, US 20200348308 A1 and US 20200348307 A1.

131. The method of embodiment 130, wherein the polynucleotide is conjugated to the peptide analyte according to methods of embodiments 119-129.

132. The method of embodiment 130 or 131, wherein analyzing the extended recording tag comprises sequencing of the extended nucleic acid recording tag to obtain the identifying information regarding the binding agent, and associating the identifying information regarding the binding agent with the peptide analyte, or with a component or a feature of the peptide analyte.

133. The method of embodiment 132, wherein analyzing the peptide comprises identifying at least one component of the peptide.

134. The method of embodiment 132, which analyzing the peptide analyte comprises identifying a sequence of at least a portion of the peptide analyte.

In this embodiment, a set of binding agents is used each binding agent comprising (i) a binding moiety configured to bind specifically to an N-terminal amino acid (NTAA) or a functionalized NTAA of the peptide analyte immobilized on the solid support; and (ii) a nucleic acid coding tag attached to the binding moiety and comprising a barcode sequence that comprises identifying information regarding the binding moiety. Preferably, the set of binding agents contains at least 5 different binding agents that bind specifically to different NTAA or functionalized NTAA of the peptide. Optimally, the set of binding agents contains about 20 different binding agents that bind specifically to different NTAA or functionalized NTAA of the peptide. After binding of one of the binding agents to the peptide analyte and transferring the identifying information of this binding agent from the coding tag to the recording tag, the NTAA or functionalized NTAA of the peptide is cleaved to expose anew NTAA, followed by optional new NTAA functionalization. Then, the described binding cycle is repeated one or more times, generating a nucleic acid encoded library on the recording tag associated with the peptide, where the nucleic acid encoded library is representative of the binding history of the peptide. After completion of the binding cycles, extended recording tags from multiple peptides analyzed in parallel are collected and the identifying information regarding the binding agents that were bound to the peptides is obtained from the extended recording tags using nucleic acid sequencing. Accordingly, amino acid sequence of at least a portion of the peptide can be identified in a highly parallel manner. Additional details can be found in US 20190145982 A1.

135. The method of embodiment 134, which is conducted to achieve peptide sequence coverage of about 90% or more.

136. A conjugation reagent, which comprises a cyclohexan-1,2-dione and a reactive handle, wherein reactive handle is selected from the group consisting of: azide, tetrazine, methyltetrazine, cyclopropene, trans-cyclooctene, substituted trans-cyclooctene (such as aTCO), alkene, terminal alkyne, cyclooctyne tetrazine, ester, thioester, nitrile, alkylating agent, phosphate ester, azidoacetamide, semicarbazide, phospholipid, ketone, aldehyde, hydrazide, alkoxyamine, phosphine, nitrone, nitrile oxide, diazo compound, tetrazole, quadrocyclane, iodobenzene, cyclooctyne, bicyclononyne (BCN), diarykcyclooctyne (DBCO), norbornene, vinyl, isonitrile, and cycloaddition reactant. aTCO is a functionalized axial-5-hydroxy-trans-cyclooctene (described in Fox J M, et al., "General, Divergent Platform for Diastereoselective Synthesis of trans-Cyclooctenes with High Reactivity and Favorable Physiochemical Properties. Angew Chem Int Ed Engl. 2021 Mar. 19").

137. The conjugation reagent of embodiment 136, wherein the CHD and the reactive handle are connected by a hydrophilic linking group comprising a polar group.

138. The conjugation reagent of embodiment 137, wherein the polar group comprises polyethylene glycol (PEG).

139. The conjugation reagent of any one of embodiments 136-138, wherein the conjugation reagent comprises an additional reactive handle.

140. The conjugation reagent of any one of embodiments 136-139, which further comprises a detectable label.

141. The conjugation reagent of any one of embodiments 136-140, having the following formula:

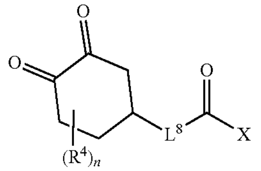

wherein X is OR, OM, a leaving group, or $NR_2$, $L^8$ is an organic linker, each R is independently $C_{1-2}$ alkyl, $C_{1-2}$ haloalkyl, $C_{1-2}$ alkoxy, COOR, —SOR, or $C(O)NR_2$;

each R is independently H, $(PEG)_m$, or $C_{1-8}$ alkyl optionally substituted with up to three groups selected from halo, $C_{1-2}$ alkyl, $C_{1-2}$ haloalkyl, $C_{1-2}$ alkoxy, hydroxy, amino, COOH, carbonyl (oxo), a detectable label, and a reactive handle;

or two R groups on one N can be taken together to form a 4-8 membered ring optionally containing an additional one or two heteroatoms selected from N, O and S as ring members and optionally substituted with one or two groups selected from halo, $C_{1-2}$ alkyl, $C_{1-2}$ haloalkyl, $C_{1-2}$ alkoxy, hydroxy, carbonyl (oxo), a detectable label, and a reactive handle;

PEG is an ethylene glycol monomer, and m is 1-20;

n is 0, 1, 2, or 3; and

M is a cationic counterion.

142. The conjugation reagent of embodiment 141, which is of the formula:

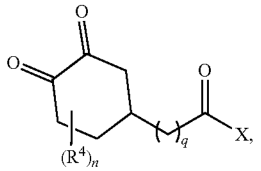

q is an integer from 0 to 10;

or a salt thereof.

143. The conjugation reagent of embodiment 141, which is of the formula.

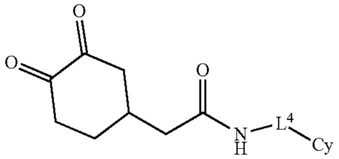

wherein:

$L^4$ is an organic linker, and

Cy is a reactive handle.

144. The conjugation reagent of embodiment 143, wherein the reactive handle is selected from an electron-deficient diene, an activated dienophile, and a 1,3-dipole.

145. The conjugation reagent of embodiment 143, wherein the reactive handle is an azide group, a tetrazine ring, or a strained alkene, or an alkyne.

146. The conjugation reagent of embodiment 143, which further comprises a detectable label covalently attached to the linker $L^4$.

In any of the foregoing embodiments, a CHD is a cyclohexane-1,2-dione. In some embodiments, it is substituted at the 4-position with a group or linker that connects it to the remainder of the conjugation reagent. The CHD can be substituted as described herein, and in some embodiments the CHD ring is not substituted other than where it is attached to the conjugation reagent.

Using the methods disclosed herein, the conjugation reagent can be used to form a conjugate with any suitable target molecule, Typically, the target molecule is a biomolecule such as a peptide, nucleic acid, carbohydrate, lipid, lipopolysaccharide, phospholipid, or combination of these. In certain embodiments, the target molecule is a peptide, which may contain modified amino acids; for example, the target molecule may be tagged, labeled, masked, or protected prior to application of the methods of the invention. Methods known in the art and methods disclosed herein can be used to mask or protect other reactive groups in the peptide.

The peptide may contain one or more post-translational modifications. A post-translational modification (PTM) of a peptide, polypeptide, or protein may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation (e.g., N-linked, O-linked, C-linked, phosphoglycosylation), glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation A post-translational modification includes modifications of the amino terminus and/or the carboxyl terminus of a peptide, polypeptide, or protein. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini of a peptide, polypeptide, or protein. Post-translational modification can regulate a protein's "biology" within a cell, e.g., its activity, structure, stability, or localization. Phosphorylation is the most common post-translational modification and plays an important role in regulation of protein, particularly in cell signaling (Prabakaran et al., 2012, Wiley Interdiscip Rev Syst Biol Med 4: 565-583). The addition of sugars to proteins, such as glycosylation, has been shown to promote protein folding, improve stability, and modify regulatory function. The attachment of lipids to proteins enables targeting to the cell membrane. A post-translational modification can also include peptide, polypeptide, or protein modifications to include one or more detectable labels.

Optionally, the target molecule in the methods herein can be immobilized on a solid support (also referred to as "substrate surface"). The solid support can be any porous or non-porous support surface including, but not limited to, a bead, a microbead, an array, a glass surface, a silicon surface, a plastic surface, a filter, a membrane, nylon, a silicon wafer chip, a flow cell, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere. Materials for a solid support include but are not limited to acryl amide, agarose, cellulose, nitrocellulose, glass, gold, quartz, polystyrene, polyethylene vinyl acetate, polypropylene, polymethacrylate, polyethylene, polyethylene oxide, polysilicates, polycarbonates. Teflon, fluorocarbons, nylon, silicon rubber, polyanhydrides, polyglycolic acid, polyactic acid, polyorthoesters, functionalized silane, polypropylfumerate, collagen, glycosaminoglycans, polyamino acids, or any combination thereof. Solid supports further include thin film, membrane, bottles, dishes, fibers, woven fibers, shaped polymers such as tubes, particles, beads, microparticles, or any combination thereof. For example, when solid surface is a bead, the bead can include, but is not limited to, a polystyrene bead, a polymer bead, an agarose bead, an acrylamide bead, a solid core bead, a porous bead, a paramagnetic bead, glass bead, or a controlled pore bead.

Proteins, polypeptides, or peptides can be immobilized to a surface of a solid support by its C-terminus, N-terminus, or an internal amino acid, for example, via an amine, carboxyl, or sulfydryl group. Standard activated supports used in coupling to amine groups include CNBr-activated, NHS-activated, aldehyde-activated, azlactone-activated, and CDI-activated supports. Standard activated supports used in carboxyl coupling include carbodiimide-activated carboxyl moieties coupling to amine supports. Cysteine coupling can employ maleimide, iodoacetyl, and pyridyl disulfide activated supports. An alternative mode of peptide carboxy terminal immobilization uses anhydrotrypsin, a catalytically inert derivative of trypsin that binds peptides containing lysine or arginine residues at their C-termini without cleaving them.

The methods of the invention provide mild conditions for forming a conjugate linking a conjugation reagent that comprises a CND group to a target molecule that contains at least one CHD-reactive group. The CHD-reactive group can be any moiety that reacts irreversibly with a CHD group under the conditions of the invention, preferably with high selectivity for the CHD group. Typically, the CHD-reactive group comprises an acylated $NH_2$ group, i.e., an $NH_2$ bonded to an $sp^2$ carbon that is in turn double bonded to a heteroatom (N, O or S), which reacts with the 1,2-dicarbonyl of the CHD group. Suitable CHD-reactive acylated $NH_2$ groups include guanidine, amidine, urea, or thiourea groups that contain an $NH_2$. Where the target molecule comprises a peptide, the CHD-reactive group can be the guanidine group of an arginine residue in the peptide.

Conditions of the reaction of the target molecule with the conjugation reagent typically comprise contacting the target molecule with the conjugation reagent in an aqueous medium at a pH of 13 or below, preferably 12.5 or below, or below 12. In some embodiments, the pH is between 7 and 10.

The reaction medium typically comprises a buffer such as those disclosed herein, including MOPS (3-(N-morpholino) propanesulfonic acid), HEPES, potassium phosphate, sodium phosphate, potassium biphosphate, sodium biphosphate, SSC (saline sodium citrate), CBC (sodium carbonate/ bicarbonate), sodium carbonate, potassium carbonate, PIPES (piperazine-N,N'-bis(2-ethanesulfonic acid), PBS (phosphate-buffered saline), sodium pyrophosphate, TAPS ([tris(hydroxymethyl)methylamino]propanesulfonic acid), DAP (diammonium phosphate), CAPS (N-cyclohexyl-3-aminopropanesulfonic acid), sodium bicarbonate, potassium bicarbonate, sodium borate, sodium borate decahydrate, imidazole, and combinations of these that provide the desired pH. In some embodiments, the buffer is selected from potassium phosphate, CBC, CAPS, and sodium pyrophosphate.

The buffer is typically used at a concentration of 0.1M or higher, often at a buffer concentration of 0.5M or higher, and optionally at a buffer concentration of 1M to 2M, or higher than 2M. Higher ionic strength in the reaction medium is believed to promote the irreversible reaction of a CHD group with a CHD-reactive group; in some embodiments of the invention, a buffer concentration of 1-2M is used, the corresponding solutions have ionic strength from 0.2 M to 4 M. In some embodiments of the invention, the reaction medium has ionic strength from 0.5 M to 1 M, or from 1 M to 2 M, or from 2 M to 4 M.

Reaction temperature can be about ambient temperature, i.e., 20° C. or 25° C., or it can be elevated to 30-100° C. to promote the irreversible reaction of the CHD group with the CHD-reactive group. Commonly, the reaction temperature can be about 50° C. or 60° C. or higher, and in some embodiments the reaction temperature can be up to about 70° C., 80° C., or 90° C. In many embodiments, a temperature between about 60° C. and 90° C. is suitable.

Conjugation reagents for use in the methods of the invention comprise an organic scaffold and a CHD group and preferably also contains an additional reactive handle and/or a detectable label. The nature and composition of the organic scaffold are very flexible, provided the organic scaffold is compatible with the reaction medium and stable under the reaction conditions. Typically, the organic scaffold comprises a combination of alkyl groups, heteroatoms (N, O and S), polyether groups such as polyethylene glycols, and stable linkages such as amides, ureas, carbamates, ethers, thioethers, and the like, and optionally rings such as phenyl, heteroaryl (pyridinyl, thienyl, thiazolyl, imidazolyl, triazolyl, oxazolyl, isoxazolyl, and the like), and 3-8 membered cycloalkyl and heterocyclic rings (e.g., THF, pyrrolidine, pyran, dioxane, and the like).

Figure 5A:
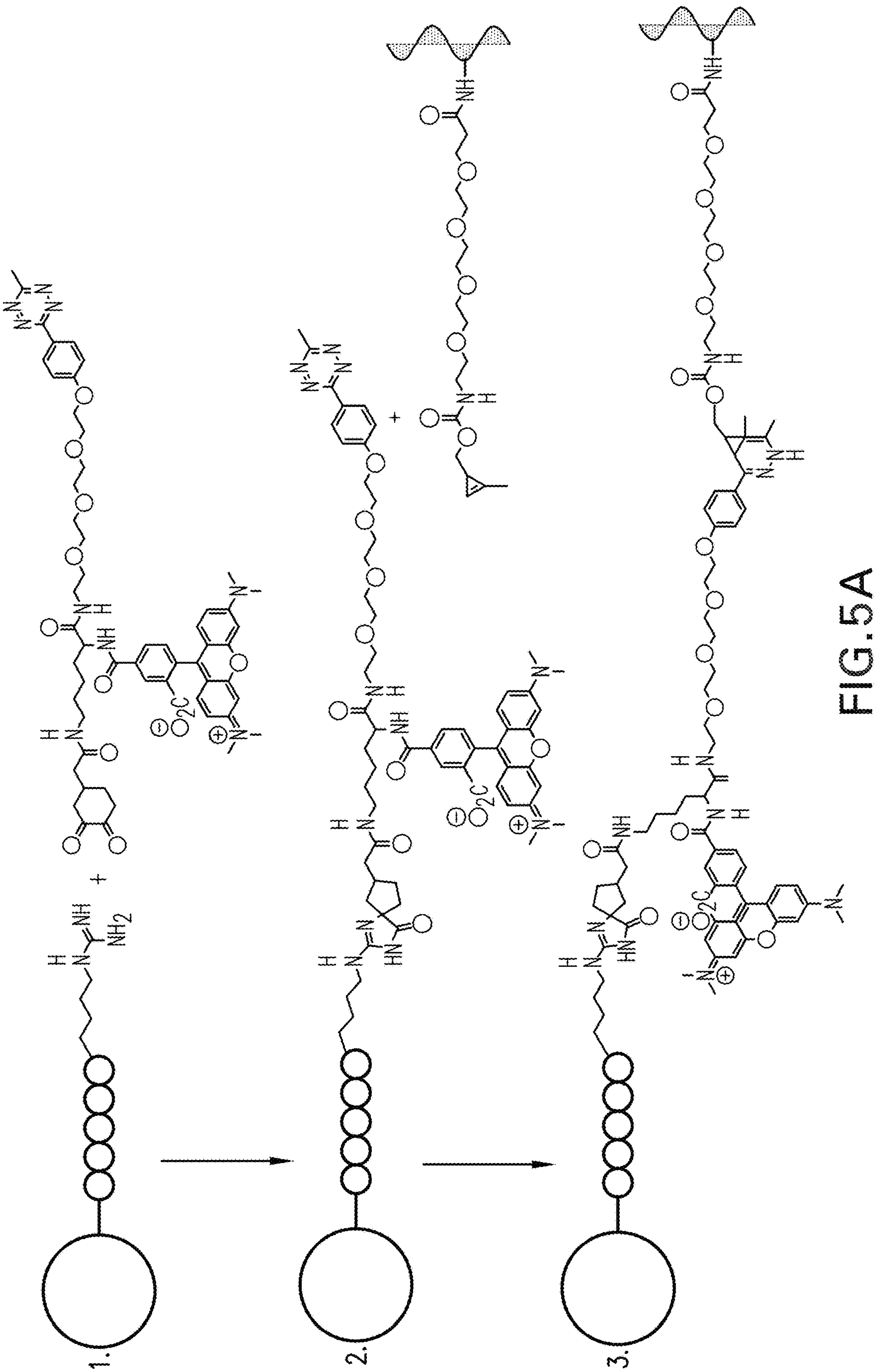
FIG. 5A depicts fluorescence turn-on upon conjugate formation on bead surfaces using iEDDA chemistry. Step 1. Conjugation of methyltetrazine-CHD-fluorophore to peptides on the beads. Step 2. Conjugation of dienophile modified nucleic acids to fluorescence-quenched peptides anchored to the bead surface. Step 3. Enhanced fluorescent signals can be detected upon conjugate formation.
Figure 5B:
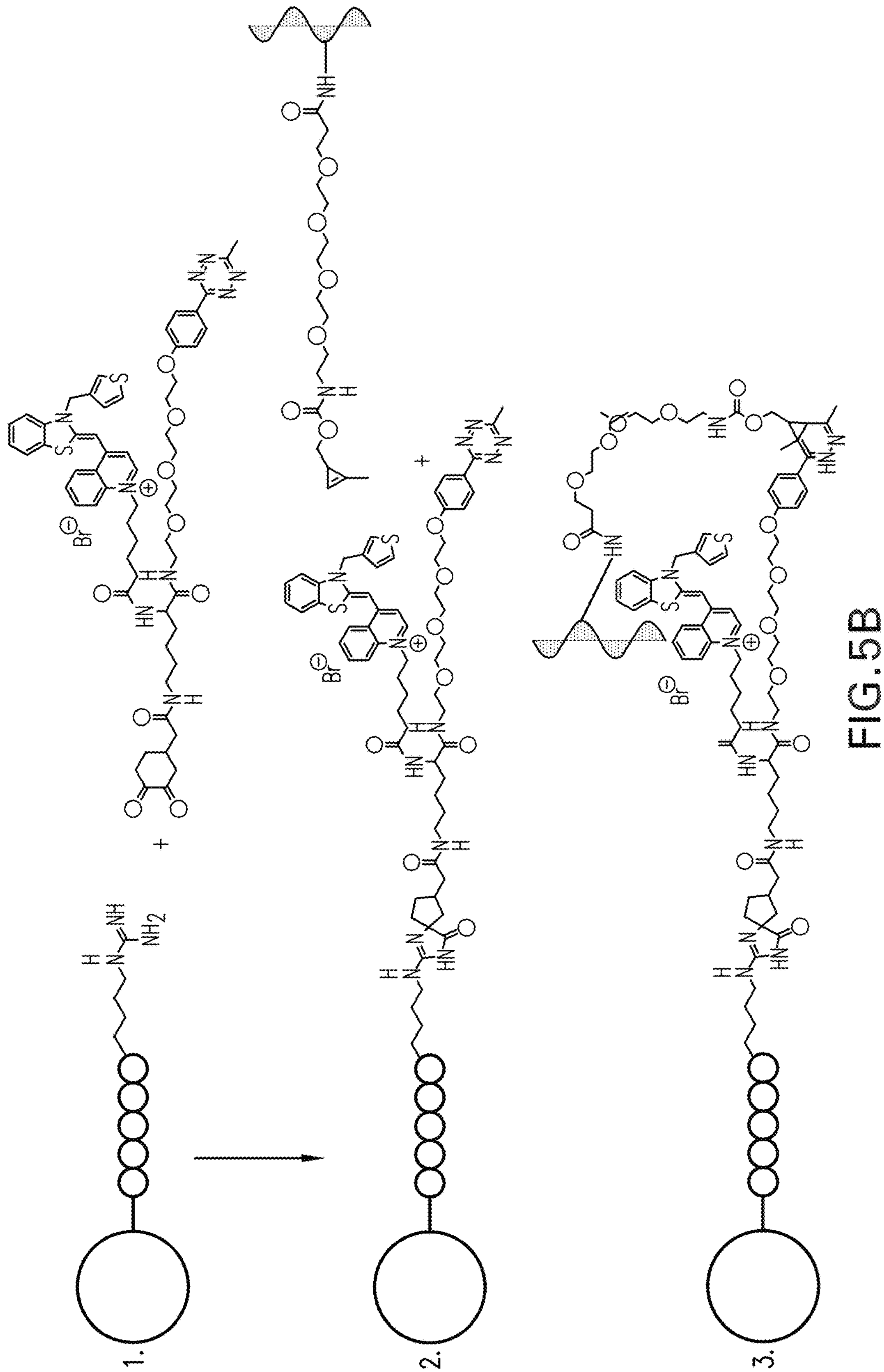
FIG. 5B depicts fluorescence turn-on upon conjugate formation on the bead surface using a dual quenched nucleic acid binding probe. Step 1. Conjugation of methyltetrazine-CHD-TO to peptides on the beads. Step 2. Conjugation of dienophile modified nucleic acids to fluorescence-quenched peptides anchored to the bead surface. Step 3. Enhanced fluorescence upon the elimination of tetrazine and nucleic acid-TO binding for highly specific conjugate formation detection.

An organic scaffold for a conjugation reagent can comprise a core structure with multiple functional groups that can be used to attach the core structure to a reactive handle, CHD, label, or other feature. Lysine is an example of a suitable core structure, having a carboxylate group, a secondary amine, and a primary amine, and thus capable of being linked to three features. Thus a lysine core can be decorated with a CHD group, another reactive handle, and a detectable label. Each of these features can be attached directly to the functional groups of the lysine, or any or all of them can be attached to the lysine core through a linking group such as an alkyl chain, a PEG chain (e.g., comprising 2, 3, 4, 5, or more polyethylene glycol monomer units. Examples of conjugation reagents based on a lysine core are shown in FIGS. 5A and 5B. Other amino acids, both natural and unnatural, can be used as a core structure in place of lysine; examples include glutamine, glutamic acid, aspartic acid, cysteine, GABA, PABA, beta-alanine, and ornithine.

Methods of the invention can convert a target compound into a modified target compound that is covalently attached to a conjugation reagent, typically via reaction between the CHD-reactive group of the target compound with the CHD of a conjugation reagent to form a covalent, irreversible connection. A target compound having more than one CHD-reactive group can be connected in this way to more than one conjugation reagent.

In some embodiments, the conjugation reagent of the invention comprises an additional reactive handle along with a CHD. In some embodiments, the conjugation reagent comprises two or more than two additional reactive handles. Reactive handles are functional groups that can be used to attach the conjugation reagent to another molecular entity, such as a second target molecule. In order to react with a reactive handle, the second target molecule needs to have a complementary reactive handle that specifically reacts with the first reactive handle. Pairs of complementary reactive handles are well known in the field and include click-chemistry reactants, cycloaddition reactants, and the like. In some embodiments, preferred reactive handles are bioorthogonal reactive handles.

Bioorthogonal reactive handles are ones that do not react with natural components of a typical biochemical system, so they can be used in such systems without interference from the natural components. They are commonly used to specifically label a target molecule in a biological system. Two or more bioorthogonal reactive handles can also be included in one conjugation reagent or one system without cross-reacting, so the user can selectively use one reactive handle to make one connection or attachment, without disturbing a bioorthogonal reactive handle in the same conjugation reagent. Thus, in a compound that comprises a 1,2-cyclohexanedione moiety (CUD) as one reactive handle, a second bioorthogonal reactive handle such as a tetrazine or other inverse-electron demand Diels-Alder reactant (cyclopropene, strained cyclic alkyne, trans-cyclooctene), or a [3+2] cycloaddition reactant such as an alkyl azide, terminal alkyne) can also be present. In these compounds and systems, the 1,2-cyclohexanedione can be used to conjugate the reagent with an arginine-containing peptide, either before or after the bioorthogonal reactive handle (e.g., click chemistry) is used to connect the reagent with another biomolecule, bead, or surface.

In some embodiments, tetrazines are reactive handles suitable for the disclosed methods. Tetrazines are well known reactive handles for attaching fluorogenic probes to biomolecules such as peptides to enable visualization of target biomolecules in cells. Y. Lee, et al., *J. Am. Chem. Sc.* 2018, 140, 974-983. Tetrazine rings are stable in biological media, and react with specific reaction partners under mild conditions, so they are very useful for attaching a probe to a target with good selectivity. The tetrazine ring not only provides a reactive handle for connecting the probe to a target, it also can, if suitably positioned, quench fluorescence of a fluorogenic marker in the probe. In that case, when the tetrazine ring participates in a linking reaction, it loses its fluorescence quenching effect, which can be very useful for monitoring progress of the reaction attaching the probe to a target biomolecule.

In some embodiments, the invention provides a conjugation reagent that comprises a CHD group and a base-sensitive reactive handle. The base-sensitive reactive handle is one that is not sufficiently stable in strong base to be useful under such conditions, e.g. at pH above 13. Base-sensitive reactive handles include, for example, tetrazines, esters, thioesters, nitriles, alkylating agents, phosphate esters and phospholipids. As with other conjugation reagents, these can optionally comprise an additional reactive handle, in addition to the CHD group and the base-sensitive reactive handle. These conjugation reagents can also optionally comprise a detectable label Detectable Labels In some embodiments, the methods and compositions of the invention comprise a detectable label. The detectable label can be any suitable atom, molecule, or particle or a combination of two of these that is readily detectable and does not interfere with the reaction between a CHD group and a CHD-reactive group. Suitable examples of detectable labels include Nile Red, fluorescein, rhodamine, derivatized rhodamine dyes, such as 5-carboxytetramethylrhodamine, phosphor, polymethine dye, fluorescent phosphoramidite, sulforhodamine 101 acid chloride, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. In some embodiments, the detectable label is a fluorophore or a fluorogenic moiety, and may comprise a fluorophore and a quencher that reduces or modifies the fluorescent property of the fluorophore.

Fluorophores and Fluorogenic Moieties

Non-protein organic fluorophores of interest for the methods and compositions belong to following major chemical families, which are known in the art:

- Xanthene derivatives: fluorescein, rhodamine, Oregon green, eosin, and Texas red;
- Cyanine derivatives: cyanine, indocarbocyanine, oxacarbocyanine, thiacarbocyanine, and merocyanine;
- Squaraine derivatives and ring-substituted squaraines, including Seta and Square dyes;
- Squaraine Rotaxane derivatives: SeTau dyes;
- Naphthalene derivatives (dansyl and prodan derivatives);
- Coumarin derivatives;
- oxadiazole derivatives: pyridyloxazole, nitrobenzoxadiazole and benzoxadiazole;
- Anthracene derivatives: anthraquinones, including DRAQ5, DRAQ7 and CyTRAK Orange;
- Pyrene derivatives: cascade blue, etc.
- Oxazine derivatives: Nile red, Nile blue, cresyl violet, oxazine 170, etc.
- Acridine derivatives: proflavin, acridine orange, acridine yellow, etc.
- Arylmethine derivatives: auramine, crystal violet, malachite green;
- Tetrapyrrole derivatives: porphin, phthalocyanine, bilirubin; and
- Dipyrromethene or boron-dipyrromethene derivatives: BODIPY, aza-BODIPY.

Figure 5C:
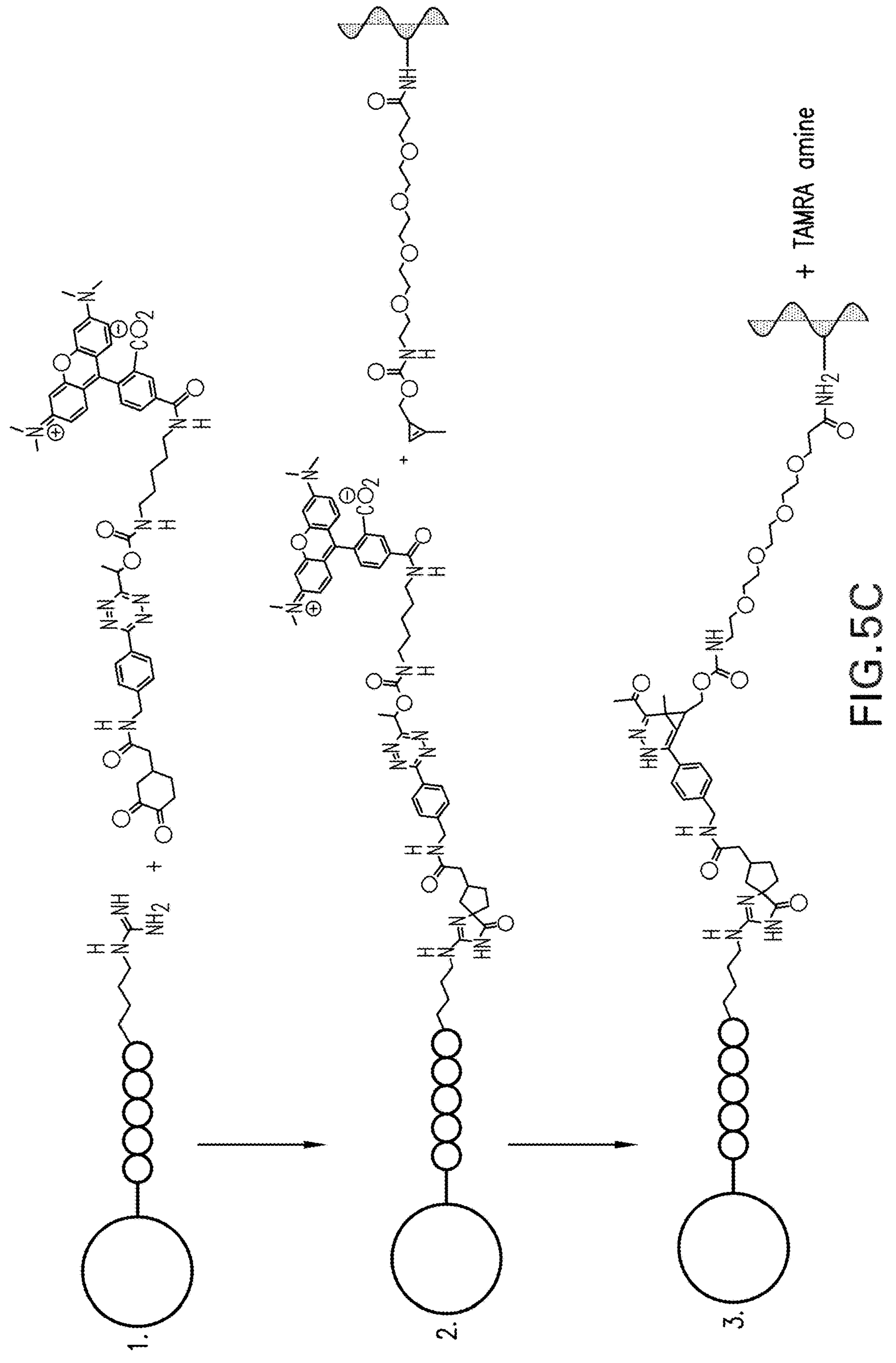
FIG. 5C depicts fluorescence turn-on upon conjugate formation on the bead surface using click-to-release fluorogenic tetrazine probe. Step 1. Conjugation of mTet-CHD-fluorophore (TAMRA is shown as an example) to peptides on the beads. Step 2. Conjugation of dienophile modified nucleic acids to fluorescence-quenched peptides anchored to the bead surface. Step 3. Fluorophore released from the conjugate and the bead surface upon the formation of conjugate and an enhanced fluorescent signal is generated.

In some embodiments, methods and compositions of the invention use a fluorophore in combination with a quenching agent such as a tetrazine ring that can be incorporated into a conjugation reagent of the invention. When proximal to a suitable fluorophore, the tetrazine ring quenches fluorescence. Reactions such as those described and exemplified herein can modify the conjugation reagent structure by either reacting with the tetrazine to disrupt its quenching effect, which allows the progress of the reaction to be monitored by the increase of fluorescence. This can occur, for example, when the tetrazine reacts with a reactive handle comprising a strained alkene or alkyne, as illustrated in FIG. 5A. In other examples, a conjugation reagent comprising a DNA-quenchable fluorophore can be used to link a peptide and a nucleic acid. A reactive handle or CHD on the conjugation reagent is used to link the conjugation reagent to a nucleic acid, and quenching of the DNA-quenchable fluorophore can be used to monitor the nucleic acid conjugation reaction, as illustrated in FIG. 5B. In other examples, the tetrazine can be positioned between the CHD moiety and a detectable label in a way that reaction of the tetrazine can cause cleavage of the detectable label, as illustrated in FIG. 5C.

High pH conditions typically employed previously for cyclohexanedione (CHD) modification of arginine side chains have several liabilities for polypeptide analysis applications, such as polypeptide sequencing. In particular, cysteine side chains are known to form dehydroalanine under basic conditions, even when alkylated by iodoacetamide or other commonly employed cysteine modification reagents. Dehydroalanine is an unstable and reactive product that can subsequently alkylate other amino acids to generate cyclized products unsuitable for sequencing. Other reaction products are possible and further complicate downstream analyses. Serine, threonine, phosphoserine, and phosphothreonine residues can be similarly modified under basic conditions to yield dehydroalanine. As such, these residues become confiscated during polypeptide sequencing applications. Basic pH conditions also facilitate peptide bond hydrolysis to generate unanticipated, shorter peptides that complicate sequence mapping (Oliyai C, Borchardt R T. Chemical pathways of peptide degradation. V I. Effect of the primary sequence on the pathways of degradation of aspartyl residues in model hexapeptides. Pharm Res. 1994 May; 11(5): 751-8). Deamidation of asparagine is also well documented under basic conditions (Tyler-Cross R, Schirch V. Effects of amino acid sequence, buffers, and ionic strength on the rate and mechanism of deamidation of asparagine residues in small peptides. J Biol Chem. 1991 Nov. 25; 266(33):22549-56) and further complicates sequence identification.

Arginine modification under mild reaction conditions would facilitate peptide analysis by eliminating undesired side chain elimination and peptide cleavage. While reversible, covalent products are formed between vicinal diones (diketones) and guanidine side chains at neutral pH, a dehydration/cyclization reaction is required for irreversible modification. The rate for dehydration is significantly increased at basic pH conditions, necessitating high pH (pH>13) for efficient reaction. Surprisingly, we have identified a more neutral pH reaction conditions (pH=7-9) disclosed herein that also facilitate the cyclization/dehydration reaction. These neutral pH reaction conditions significantly improve the utility for CHD as a tool for polypeptide analysis and related technologies. A reaction of 1, 2-Cyclohexanedione (CHD) with arginine residues of polypeptides at pH=8-9 in borate buffer was previously reported (Patthy L, Smith E L The Journal of Biological Chemistry, 31 Dec. 1974, 250(2):557-564); however, the previously reported reaction conditions resulted in an unstable linkage that can undergo reversible reaction (also known as hydrated product, DHCH-arginine) in a non-borate buffer and non-acidic conditions, which largely restricted use of this reaction in most conjugation applications. In contrast, under conditions reported here, an irreversible covalent linkage (also referred as dehydration product) is formed between the CHD and arginine at a pH lower than 13, making this reaction particularly suitable for conjugation of polypeptides with polynucleotides, as well as for other applications where pH>13 can compromise reaction components. Moreover, the CHD-based conjugation described herein offers improved specificity for attachment of molecules, including polynucleotides, to polypeptides, in comparison with other known methods, such as amine-specific or carboxyl-specific reagents, which can target multiple amino acid residues. Instead, CHD-based conjugation is strictly arginine-specific.

For many applications, such as linking two biomolecules together or attaching a label to a biomolecule, the following disclosure provides a conjugation reagent containing a CHD group. So-called 'click chemistry' reactants are commonly used in biological systems, and are orthogonal to CHD linking chemistry and are thus useful as additional reactive handles in the CHD-containing conjugation reagents and methods of the invention. Click chemistry reactive handles include reactants for the following reactions: the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2]cycloaddition, alkene and tetrazine inverse electron demand Diels-Alder (IEDDA) reaction (e.g., methyltetrazine (mTet) or phenyl tetrazine (pTet) and trans-cyclooctene (TCO)); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothiocyanate, an aldehyde, an epoxide, or the like. In some embodiments, iEDDA click chemistry is used for immobilizing polypeptides to a support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction. In one case, a polypeptide is labeled with a bifunctional click chemistry reagent, such as alkyne-NHS ester (acetylene-PEG-NHS ester) reagent or alkyne-benzophenone to generate an alkyne-labeled polypeptide. In some embodiments, an alkyne can also be a strained alkyne, such as cyclooctynes including Dibenzocyclooctyl (DBCO) and others.

These reactants can be used in combination with the CHD reactions, as they provide orthogonal reactive handles and are typically compatible with biological systems. Bioorthogonal reactive handles are ones that do not react with natural components of a typical biochemical system, so they can be used in such systems without interference from the natural components. They are commonly used to specifically label a target molecule in a biological system. Two or more bioorthogonal reactive handles can also be included in one conjugation reagent or one system without cross-reacting, so the user can selectively use one reactive handle to make one connection or attachment, without disturbing a bioorthogonal reactive handle in the same conjugation reagent. Thus, in a compound that comprises a 1,2-cyclohexanedione moiety (CHD) as one reactive handle, a second bioorthogonal reactive handle such as a tetrazine or other inverse-electron demand Diels-Alder reactant (cyclopropene, strained cyclic alkyne, trans-cyclooctene), or a [3+2] cycloaddition reactant such as an alkyl azide, terminal alkyne) can also be present. In these compounds and systems, the 1,2-cyclohexanedione can be used to conjugate the reagent with an arginine-containing peptide, either before or after the bioorthogonal reactive handle (e.g., click chemistry) is used to connect the reagent with another biomolecule, bead, or surface.

In some embodiments, a cleavable moiety can be additionally included in the CHD linker disclosed herein during formation of polypeptide-polynucleotide conjugates according to the methods disclosed herein. This cleavable moiety can be used to evaluate efficiency of the polypeptide-polynucleotide conjugate formation or efficiency of conjugate processing during downstream assays (such as ProteoCode assay) by releasing the polypeptide from the conjugates and identifying the released polypeptide by mass spectrometry.

A key step in the Proteocode™ sequencing assay is to prepare polynucleotide-tagged polypeptides (sequencing substrate) immobilized on a solid support, such as beads, from complex biological samples containing polypeptides. Multiple strategies can be employed for preparing polynucleotide (DNA)-tagged polypeptides immobilized on solid support from complex biological samples, such as cell lysates. A standard procedure usually employs a site-specific protease, such as trypsin that specifically cleaves after lysine and arginine residues, for digestion of native polypeptides prior to chemical activation and DNA tagging; however, polypeptides after digestion have dual N-terminal alpha-amine and Lysine epsilon-amine groups, so the following selective activation of one amine over the other is problematic.

To enable ProteoCode™ sequencing, a DNA-tag must be attached directly or via a linker to the desired polypeptide molecules, preferably at the C-terminal amino acid. For example, cyclohexanedione (CHD) derivatives enable covalent modification of the C-terminal arginine resulting from tryptic digestion. Such a CHD reagent will contain either a DNA tag or reactive moiety to be subsequently modified with a correspondingly reactive DNA sequence (e.g., through click chemistry). Preferably, peptides are immobilized through the N-terminus or amino acid side chain (e.g., lysine), such that excess DNA reagents are removed efficiently. The traceless, cleavable amine modification reagents described herein afford efficient mechanism for polypeptide immobilization in a ProteoCode compatible format.

Numerous sample processing steps are required to convert an input protein sample into a format suitable for ProteoCode sequencing and to allow efficient conjugation of DNA-based recording tags to arginine residues of polypeptides. Initially, proteins are extracted into a suitable buffer and denatured to solubilize and unfold tertiary structure. Removal of insoluble biological matter, lipids, etc. may or may not be required. Cysteines are reduced and alkylated to prevent inadvertent disulfide linkages throughout processing steps. Lysine side-chains are modified with an amine reactive reagent (ARR1) to "block" these amine side-chains during subsequent sample processing steps. Typically, NHS-esters are employed for this step because they are readily inactivated through hydrolysis. Alternatively, amine reactive agents such as o-phthalaldehyde (OPA) may be employed, and unreacted reagent can be removed using an amine-terminated solid support or similar method. Importantly, ARR1 may or may not contain an enrichment tag, fluorescent tag, reactive tag, or binder compatible tag to facilitate alternate workflows, solubility, purification, analysis, encoding, etc. After these protein extraction and modification steps, the protein sample is digested with a suitable protease, or mixture of proteases, to yield polypeptide fragments.

A tryptic digest with "blocked" lysine sidechains will yield polypeptide fragments that are predominantly terminated with arginine (exclusive to the protein C-terminus). Importantly, some peptides will not contain internal lysine amino acids. If one were to enrich peptides based on an enrichment tag (or similar) presented by ARR1, peptides without an internal lysine will be effectively removed from subsequent analyses. Alternatively, a larger fraction of peptides are accessible through modification of the newly formed N-termini (resulting from proteolysis) with an appropriate enrichment tag. This second amine reactive reagent (ARR2) will preferably afford a traceless and cleavable enrichment tag (cleavable linker), such that, upon removal, the original unmodified N-terminus is regenerated. The described approach of capturing and releasing N-termini of processed polypeptides is called herein an N-terminal workflow. Traceless, cleavable linkers are preferable for ARR2 mediated N-terminal amine modification to enable subsequent ProteoCode™ analyses, which require an unmodified N-terminus. Such reagents will contain an amine reactive group (i.e. activated ester or isothiocyanate), a cleavable moiety (photocleavable nitrophenyl ester), and an enrichment tag (biotin or click-chemistry compatible tag) for surface immobilization. Potential amine reactive groups include succinimidyl esters, pentafluorophenyl esters, para-sulfo tetrafluorophenyl esters, para-nitrocarbonates, chloroformates, sulfonyl chlorides, and isothiocyanates. Other examples are shown below. Examples of cleavable moieties are nitrophenyl esters, acylhydrazones, alloc, and amino acid-based moieties. Other examples are shown below. Enrichment tags can be derived from biotin, desthiobiotin, click chemistry reagents, halotag compatible reagents, native chemical ligation, antibody epitope tags, and so on.

In some embodiments, the examples of amine-reactive groups include:

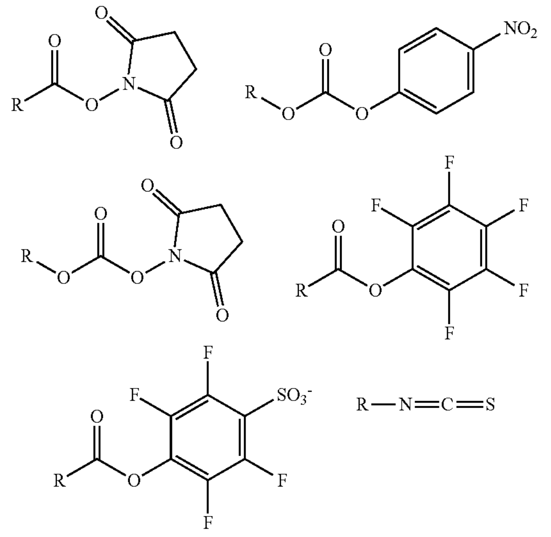

In some embodiments, the examples of cleavable linkers include:

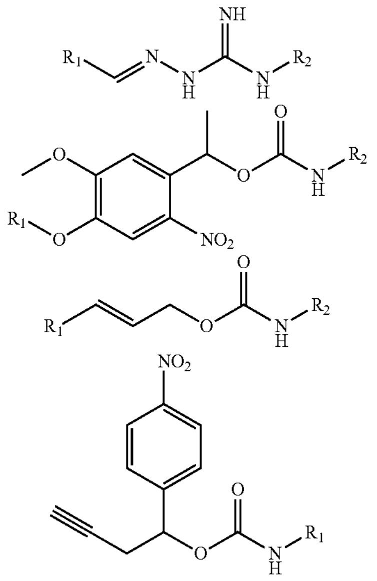

Figure 7:
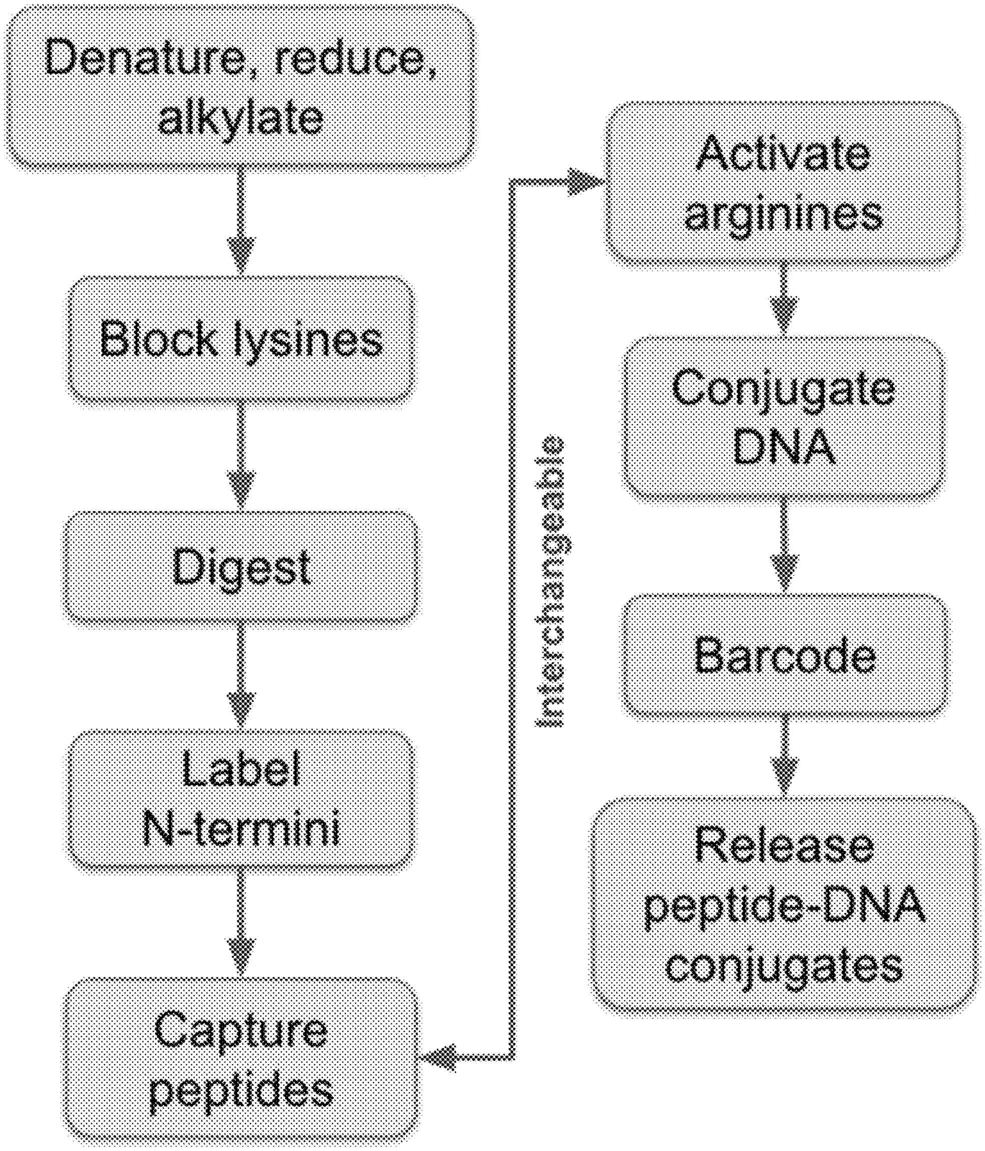
FIG. 7. Exemplary N-terminal workflow for processing of polypeptides from biological samples. After reduction and alkylation of cysteine residues, lysine residues are blocked with a first amine reactive reagent (ARR1) followed by tryptic digestion of polypeptides. Then, polypeptide N-termini are labeled with a second amine reactive reagent (ARR2) and captured to a solid support through ARR2 enrichment tag. C-terminal arginine residues are "activated" (modified) by an appropriate CHD reagent, followed by formation of polypeptide-DNA conjugate.

FIG. 7 shows an exemplary N-terminal workflow for processing of polypeptides from biological samples that allows for subsequent ProteoCode assay. In this workflow, proteins are solubilized and denatured, cysteines are reduced and alkylated, and lysines are modified to "block" them during subsequent reactions. Protein solubilizing and denaturing conditions may include chaotropes (e.g., urea or guanidinium chloride), non-ionic surfactants (triton, NP-40, etc.) ionic surfactant (sodium dodecyl sulfate, deoxycholate), organic additives (acetonitrile, formamide, etc.). Elevated temperature may also aid protein denaturation. Upon denaturation, cysteines are reduced and alkylated to prevent inadvertent cysteine cross-linking between proteins/peptides. Reducing agents are typically employed at concentrations of 10-50 mM and may include dithiothreitol (DTT), tris(2-carboxyethyl)phosphine (TCEP), amongst others. Alkylating reagents (typically 10-100 mM) may include iodoacetamide (IAA), N-ethylmaleimide (NEM), 4-vinylpyridine, acrylamide, or other cysteine reactive reagents.

In some embodiments, a lysine reactive reagent (ARR1) is implemented to "block" lysine side chains prior to proteolytic digestion such that most peptides have a carboxy-terminal arginine. The extreme carboxy-terminus will have the naturally produced amino acid and chemical modifications are likely only nearly complete leading some fraction of lysines at the carboxy-terminus (when using a trypsin-like protease). ARR1 reagents may be implemented prior to reduction/alkylation, but these steps are generally employed first to ensure chemical access to all lysines, including those buried within the protein structure. ARR1 reagents are typically employed at 0.1-50 mM to ensure nearly complete lysine modification. ARR1 reagents may include activated esters (succinimidyl esters, pentafluorophenyl esters, nitrophenyl esters, etc.), isothiocyanates, isocyanates, acyl azides, sulfonyl chlorides, aldehydes, dialdehydes (e.g., ortho-phthalaldehyde), glyoxals, epoxides, oxiranes, carbonates, aryl halides, imidoesters, carbodiimides, and anhydrides. The lysine reactive reagent (ARR1) may be quenched, scavenged, inactivated or otherwise removed before proteolytic digestion. Porcine trypsin is commonly employed for proteolysis but other proteases may be implemented. Tryptic digestion of ARR1 modified proteins results in peptides predominantly terminated with arginine at the carboxy-terminus; CHD-based arginine-specific chemistry therefore provides a convenient mechanism for chemical modification restricted to the carboxy-terminus of polypeptides. Other site-specific proteases, both natural and engineered, configured to cleave polypeptides predominantly at arginine residues can be used in the claimed methods instead of trypsin. One example is ArgC (Clostripain), which cleaves at the C-terminus of arginine residues, including sites next to proline; it also cleaves at lysine residues. Other examples include an engineered trypsin or ArgC protease that is evolved to cleave polypeptides predominantly at arginine residues. In some embodiments, cleavage predominantly at arginine residues refers to a preferential cleavage of a peptide bond adjacent to an arginine residue compared to any other residue (such as 10000, 1000, 100, or 10 times more likely to cleave a peptide bond adjacent to arginine residue compared to any other residue of a polypeptide). Known methods of protein engineering can be applied to select trypsin or ArgC protease variants that cleave polypeptides predominantly at arginine residues. Generally, such methods include random mutagenesis of residues in a substrate-binding pocket of the protease followed by functional selection screen of desirable protease variants by a phage display, such as functional selection of trypsin variants expressed in *E. coli* on the surface of M13 phage. Several successful examples of proteases with a modified specificity are known (Tran D T, et al., Evolution of a mass spectrometry-grade protease with PTM-directed specificity. Proc Natl Acad Sci USA. 2016 Dec. 20; 113(51):14686-14691; Varadarajan et. al. (2005) Engineering of protease variants exhibiting high catalytic activity and exquisite substrate selectivity. Proc. Natl. Acad. Sci. USA. 102:6855-6860; Varadarajan et. al, (2008) Highly active and selective endopeptidases with programmed substrate specificities. Nat. Chem. Biol. 4:290-294; Varadarajan et. al. (2009) An Engineered Protease that Cleaves Specifically after Sulfated Tyrosine. Angew. Chem. Int. Ed. Engl. 47:7861-7863; Olsen et. al. (2000) Function-based isolation of novel enzymes from a large library. Nat. Biotechnol. 18:1071-4).

After proteolysis, new amino termini become available for modification with a second amine reactive reagent (ARR2) that contains a cleavable linker and an enrichment tag. Enrichment tags enable immobilization of modified peptides onto a solid support through non-covalent interactions (such as streptavidin/biotin) and/or covalent interactions (click chemistry, photoreactive groups, etc.). Peptide immobilization enables removal of peptide modification reagents in subsequent steps, and affords the use of high concentration reactants to ensure sufficient reaction efficiency. Covalent capture of peptides makes it possible to perform multiple steps of peptide derivatization for downstream proteomic analysis.

In one particular embodiment, peptides are chemically modified ("activated") with an arginine reactive reagent containing a click chemistry compatible tag, either before or after peptide immobilization. Arginine reactive reagents may include derivatives of glyoxal, cyclohexanedione (CHD), and other guanine reactive reagents and are typically employed at 1-50 mM to ensure reaction completion. Importantly, cyclohexanedione derivatives afford nearly complete chemical reaction and limited side-product formation under high pH conditions and are a preferred reagent as a result. Moreover, the methods disclosed herein provide conditions for modification of arginine with CHD derivatives at neutral pH, thereby reducing the negative impacts of basic reaction conditions (inadvertent peptide cleavage, loss of post-translational modifications, and so on).

After immobilization and arginine modification, peptides are conjugated to a DNA recording tag, using, for example, the click-chemistry reactive handle, resulting in a polypeptide-DNA conjugate. Excess, unreacted DNA is removed by washing and an additional DNA sequence may be appended to barcode a given sample. Resulting polypeptide-DNA conjugates can be released from the solid support by, for example, cleavage of the cleavable linker to regenerate the original peptide N-terminus. The polypeptide-DNA conjugates may be analyzed by any number of techniques, including the ProteoCode™ assay.

Advantages of the described N-terminal workflow include >90% polypeptide sequence coverage and the absence of polypeptide purification columns, which significantly reduces cost and user hands-on time.

In different embodiments of the invention, different types of linkers can be utilized to immobilize polypeptides to a solid support during the N-terminal workflow. In preferred embodiments, polypeptides are covalently attached to the solid support via a cleavable linker. Cleavable linkers allow for efficient release of immobilized polypeptide-DNA conjugates with unmodified polypeptide N-termini ready for subsequent N-terminal polypeptide analysis, such as identification of the N-terminal amino acid (NTAA) of the polypeptide with the ProteoCode™ assay. In particular embodiments, the covalent bond between the NTAA and a cleavable linker is an amide bond, which allows for efficient release of polypeptide-DNA conjugates with unmodified polypeptide N-termini.

Examples of cleavable linkers suitable to generate immobilized polypeptide-DNA conjugates during the N-terminal workflow are shown below.

Photocleavable linkers with activated esters. Amine reactive reagents bearing an enrichment tag and a photocleavable linker are well established for immobilization and photocleavage of target molecules. Nitroaryl, arylcarbonylmethyl, coumarin-4-ylmethyl, and arylmethyl groups and others are established photocleavable groups (Klán P, et al., Photoremovable protecting groups in chemistry and biology: reaction mechanisms and efficacy. Chem Rev. 2013 Jan. 9, 113(1):119-91). Amine modification rates using standard activated esters are quite high, and photocleavage efficiency is near quantitative when using an appropriate light source. Appropriately designed linkers improve water solubility, stability, and enrichment tag access. Moreover, photocleavable reagents bearing various enrichment tags are commercially available, making implementation reasonably direct. Photocleavable linkers may be labile to extremes in pH and effective use of these reagents may necessitate relatively mild pH conditions during subsequent processing steps (e.g. CHD modification of arginine).

Amino acid-based linkers. Amino acids provide a unique molecular scaffold to derive "trifunctional" linkers through separate modification of the N-terminus, C-terminus, and sidechain (natural or unnatural). For example, amino acid side chains, may be functionalized with various enrichment tags using standard amine modification chemistry or produced with a pre-installed enrichment tag (e.g., biotin, desthiobiotin, mTET, photoreactive tags (diazirine, benzophenone, etc.)). C-terminal carboxylates can be converted into reactive esters through standard chemistries (CDI, EDC, etc.), provided the N-terminus is protected to prevent polymerization of the reagent. Installation of the N-terminal protected amino acid appends the enrichment tag-functionalized amino acid to primary amine substrates (e.g., peptides) through the reactive ester. Deprotection of the trifunctional linker generates a new N-terminus that can be subjected to N-terminal elimination processes such as Edman degradation or PMI-mediated N-terminal cleavage. This N-terminal elimination chemistry releases the target molecule with the original, unmodified amine while the linker remains attached to the solid support. This approach exploits well established chemistries for C-terminal activation, amine protection/deprotection, and installation of enrichment tags. Moreover, the amide bond generated after initial modification is chemically stable to extremes in pH, oxidation/reduction, etc. and thereby affords a variety of peptide modification chemistries on the immobilized peptide.

Peptoid-based linkers. Peptoids are a class of peptidomimetics where the side chains are appended to the peptide backbone nitrogen rather than an α-carbon. N-terminal elimination is also possible with peptoids, similar to Edman degradation with amino acids, although under different conditions (Proulx C, et al., On-resin N-terminal peptoid degradation: Toward mild sequencing conditions. Biopolymers. 2016 September; 106(5):726-36). To enable N-terminal elimination, peptoid N-termini react with bromoacetic acid in the presence of N,N'-diisopropylcarbodiimide (DIC) to yield a functionalized peptoid. Silver salts (e.g., $AgClO4$) mediate intramolecular N-terminal cyclization and subsequent N-terminal elimination (yielding an N-substituted morpholine-2,5-dione byproduct). Peptoid reagents with a pre-installed acetylbromide may enable direct modification of primary amines to yield the desired reagent more directly.

Palladium cleavable Alloc linker with an activated ester. Alloc linkers are standard reagents employed as amine protecting groups during solid-phase peptide synthesis. Such linkers are cleaved by a variety of palladium catalysts to yield the unprotected primary amine. Reactive esters have been demonstrated to enable amine modification with Alloc linkers, and this is a standard practice in solid-phase peptide synthesis. Moreover, enrichment tags have been appended to the distal region of the linker to enable selective enrichment of modified targets (Friedman Ohana R, et al., Improved Deconvolution of Protein Targets for Bioactive Compounds Using a Palladium Cleavable Chloroalkane Capture Tag. ACS Chem Biol. 2016 Sep. 16; 11(9):2608-17), Palladium cleavable linkers are advantageous due to inherent chemical stability (acid/base, oxidation/reduction), ease of installation, and efficient cleavage.

Self-immolative linkers through nitro-reduction Para-nitrobenzyl carbamates are one class of self-immolative linker that, upon reduction of the nitro group, eliminate the carbamate to yield the free amine (from the carbamate) along with $CO2$ and a 4-aminobenzaldehyde. This process is exothermic due to release of $CO2$ and therefore quite efficient. Importantly, such reagents are readily converted into reactive esters that react with primary amine to yield to the desired PNB-carbamate.

EXAMPLES

The following examples are offered to illustrate but not to limit the methods, compositions, and uses provided herein. Certain aspects of the present invention, including, but not limited to, embodiments for ProteoCode™ (polypeptide sequencing) assay, information transfer between coding tags and recording tags, methods for attachment of nucleotide-polypeptide conjugate to a support, methods of making nucleotide-polypeptide conjugate, methods of generating barcodes, methods of generating specific binders recognizing an N-terminal amino acid of a polypeptide, reagents and methods for modifying and/or removing an N-terminal amino acid from a polypeptide, methods of analyzing extended recording tags to analyze a component of a polypeptide analyte were disclosed in earlier published application US 20190145982 A1, US 20200348308 A1, US 20200348307 A1, WO 2020/223000, the contents of which are incorporated herein by reference in their entireties.

Example 1. Synthesis of CHD-PEG$_3$-Azide Conjugation Reagent

[1]

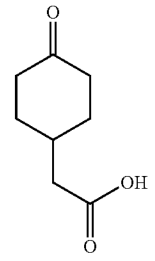

2-(4-oxocyclohexyl)acetic acid [1]

To a stirred solution of ethyl 4-oxocyclohexaneacetate (2 g, 10.855 mmol) in 25 mL of THF in a 100 mL round bottom flask equipped with a magnetic stir bar, 3 equiv. of lithium hydroxide monohydrate (1.368 g, 32.566 mmol) dissolved in IS mL of deionized water was added. The solution was allowed stir vigorously for 5 h at 25° C., where it was then quenched by the addition of 40 mL of 1M HCl (aq.) The solution was added to a separatory funnel and washed with ethyl acetate (EtOAc, 3×40 mL). The organic layers were pooled and washed with sat. NaCl (aq.) and dried over $Na_2SO_4$. The solution was filtered and condensed in vacuo to obtain a clear oil. The oil was taken up in a minimal volume of dichloromethane (DCM) and dry-loaded onto silica and purified by ISCO CombiFlash® (0-100% EtOAc in n-heptane). The fractions containing the desired product were pooled and condensed to afford a clear, colorless oil that resulted in an amorphous white solid after high vacuum overnight (>99% purity, 80% yield). The reaction was monitored by LCMS, the anticipated m/z was 156.08 and the observed m/z was 156.2.

[2]

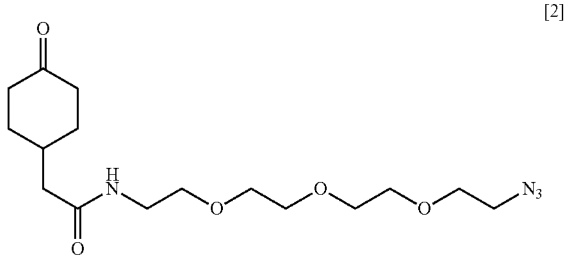 [SMILES: [N-]=[N+]=NCCOCCOCCOCCNC(=O)CC1CCC(=O)CC1]

N-[2-[2-[2-(2-azidoethoxy)ethoxy]ethoxy]ethyl]-4-oxocyclohexaneacetamide (CHO-$PEG_3$-azide) [2]

To a 100 mL round bottom flask equipped with a stir bar, 800 mg of [1] (5.128 mmol) was added and dissolved in 30 mL of dry DMF. To this, 1.02 equiv. of COMU ((1-Cyano-2-ethoxy-2-oxoethylidenaminooxy)dimethylamino-morpholino-carbenium hexafluorophosphate; 2.240 g, 5.231 mmol) and 1.02 equiv of N-diisopropylethylamine (DIPEA, 911 μL; 5.231 mmol) was added and allowed to stir for 30 minutes at 25° C. Then in a separate vial, 1.02 equiv. of 2-(2-(2-(2-azidoethoxy)ethoxy)ethoxy)ethylamine (1.142 g; 5.231 mmol) and 1.02 equiv. of DIPEA (911 μL; 5.231 mmol) were dissolved in 10 mL of dry DMF and the solution was slowly added to the stirred solution of [1]. The reaction was allowed to proceed at 25° C. for 18 h and was diluted with 40 mL of DCM, poured into a separatory funnel where an additional 100 mL was added. The organic layer was washed with 1M HCl (2×50 mL), sat. $NaHCO_3$ (2×50 mL) and sat. NaCl 1×50 mL). The organic layer was dried over $MgSO_4$, filtered, and condensed in vacuo. The resulting residue was taken up in a minimal amount of DCM and dry-loaded onto silica and purified using ISCO CombiFlash® (0-20% methanol in DCM). The resulting separation produced several fractions that were pooled and condensed to afford a yellow-orange oil (>95% purity; 73% yield.) The reaction was monitored by LCMS, the anticipated m/z was 356.21 and the observed m/z was 356.4.

[3]

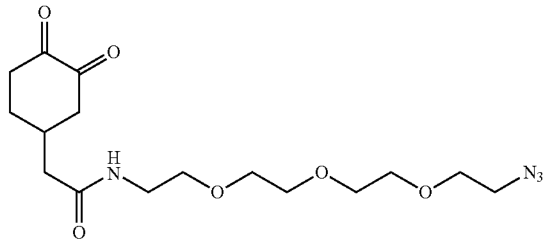

N-[2-[2-[2-(2-azidoethoxy)ethoxy]ethoxy]ethyl]-3,4-dioxocyclohexaneacetamide (CHD-$PEG_3$-azide) [3]: The resulting oil [2] (3.743 mmol) was added to a 100 mL round bottom flask equipped with a stir bar, and dissolved in 50 mL of anhydrous 1,4-dioxane. To this, 1.2 equiv. of selenium dioxide ($SeO_2$; 498 mg, 4.492 mmol) was added. The round bottom was equipped with a Findenser™ and allowed to reflux for 24 h. Upon cooling, the resulting black solution was filtered through celite and the insoluble material washed with methanol. The solution was condensed in vacuo, dissolved in a minimal amount of 10:1 DCM:methanol, and dry-loaded onto silica. The reaction mixture was purified by ISCO CombiFlash® (0-20% methanol in DCM). The resulting fractions containing the product were pooled and condensed affording an orange-brown oil (~85% purity, 70% yield). The product was stored at −20° C. for further use. The reaction was monitored by LCMS, the anticipated m/z was 370.19 and the observed m/z was 370.4.

Example 2. Synthesis of 3,4-Dioxocyclohexaneacetic Acid Conjugation Reagent and DNA-Peptide Conjugate Generation

[1]

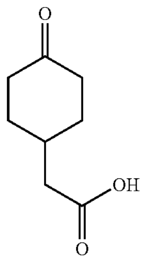

2-(4-oxocyclohexyl)acetic acid [1]: To a stirred solution of ethyl 4-oxocyclohexaneacetate (2 g, 10.855 mmol) in 25 mL of THF in a 100 mL round bottom flask equipped with a magnetic stir bar, 3 equiv. of lithium hydroxide monohydrate (1.368 g, 32.566 mmol) dissolved in 15 mL of deionized water was added. The solution was allowed to stir vigorously for 5 h at 25° C. where it was then quenched by the addition of 40 mL of 1M HCl (aq.) The solution was added to a separatory funnel and washed with ethyl acetate (EtOAc, 3×40 mL). The organic layers were pooled and washed with sat. NaCl (aq.) and dried over $Na_2SO_4$. The solution was filtered and condensed in vacuo to obtain a clear oil. The oil was taken up in a minimal volume of dichloromethane (DCM) and dry-loaded onto silica and purified by ISCO CombiFlash® (0-100% EtOAc in n-heptane). The fractions containing the desired product were pooled and condensed to afford a clear, colorless oil that resulted in an amorphous white solid after high vacuum overnight (>99% purity, 87% yield).

[4]

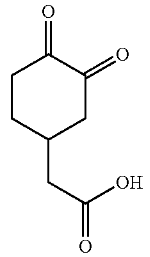

2-(3,4-dioxododecyl)acetic acid [4]: To a 100 mL round bottom flask equipped with a magnetic stir bar, 800 mg of [1] (5.128 mmol) was added and dissolved in 30 mL of glacial acetic acid. To this, 1.15 equiv. of $SeO_2$ (selenium dioxide; 654 mg, 5.897 mmol) was added and a reflux condenser was equipped to the system. The reaction was refluxed while stirring vigorously for 24 hours at 120° C. The reaction was monitored by LCMS, the anticipated m/z was 170.66 and the observed m/z was 170.2. Upon completion, the solution was cooled to room temperature, filtered through celite, and the celite was washed with DCM followed by n-heptane into a 250 mL round bottom flask. The solution was condensed in vacuo using n-heptane as an azeotrope. The resulting residue was then taken up in DCM and a small volume of methanol. The solution was dry loaded onto silica gel and purified using an ICSO CombiFlash® (0-20% methanol in DCM+1% acetic acid). The resulting separation produced several fractions that were pooled and condensed to afford a yellow-orange oil as the title compound (>95% purity; 37% yield).

[3]

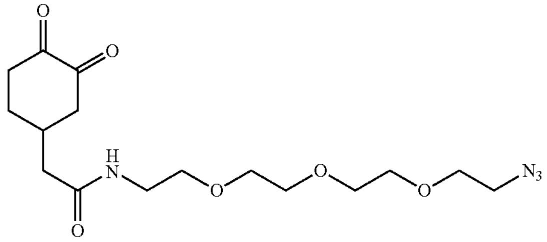

Amide coupling of CHD-acid [3]: To a stirred solution of 104 mg of CID-acid [4] in DCM within a 100 mL round bottom flask containing a football-shaped stir bar, 1.1 equiv. of DIPEA (117 μL; 0.672 mmol) was added. After stirring for 15 minutes, 1.05 equiv. of COMU ((1-Cyano-2-ethoxy-2-oxoethylidenaminooxy)dimethylamino-morpholino-carbenium hexafluorophosphate, 275 mg; 0.642 mmol) was added and allowed to stir for 30 minutes. In a separate vial, amine (2-(2-(2-(2-azidoethoxy)ethoxy)ethoxy)ethylamine, 1.05 equiv.; 117 μL; 0.642 mmol) dissolved in 2 mL of DCM was mixed with 1.1 equiv. of DIPEA (117 μL; 0.672 mmol). The amine solution was then added dropwise to the stirred CHD-acid solution and the mixture was allowed to continue stirring for 18 hours. Upon completion, the reaction was diluted with 50 mL of DCM and washed with 1.0 M HCl (aq.), then sat. $NaHCO_3$ (aq.), and lastly with sat. NaCl (aq.) The organic layer was separated and dried over $MgSO_4$, filtered, and condensed in vacuo. The residue was taken up in DCM and dry-loaded onto silica gel, applied to ISCO CombiFlash® (0-20% methanol in DCM), and the fractions containing the desired product were pooled, condensed, and analyzed by LC-MS; the anticipated m/z was 370.19 and the observed m/z was 370.4. The product is a linker or conjugation reagent comprising a CHD group and an orthogonal handle.

Peptide Treatment with CHD-Orthogonal Handle Conjugation Reagent and Subsequent DNA-Peptide Conjugate Generation:

Once the CHD-orthogonal handle conjugation reagent was synthesized, a peptide or pool of peptides (wherein cysteines are reduced and capped using TCEP and iodoacetamide; and lysines are prefunctionalized using desthiobiotin-NHS (DTB-NHS)) from a trypsin/Arg-C digestion bearing a C-terminal arginine was reacted using one of two methods:

Method A: Peptides were transferred to a low-bind 1.5 mL microcentrifuge tube and taken up in 80 μL of 0.2 M NaOH (pH 13.7). Added to this was 10 μL of a 100 mM stock solution of CHD-orthogonal handle conjugation reagent in DMSO (effective concentration 10 mM.) The tube was placed in a Thermomixer set to 37° C. for 0.5 h. Upon completion, the solution was neutralized with 1M Tris (pH 7.4).

Method B: Peptides were transferred to a low-bind 1.5 mL microcentrifuge tube and taken up in 80 μL of 1 M or 2 M potassium phosphate buffer (KPhos; pH 8.3). Added to this was 10 μL of a 100 mM stock solution of CHD-orthogonal handle conjugation reagent in DMSO (effective concentration 10 mM.) The tube was placed in a Thermomixer set to 80° C. for 1.0 h (for 2.0 M KPhos) or 1.5 h (for 1.0 M KPhos). Upon completion, the solution was neutralized with 1M Tris (pH 7.4).

Figure 1:
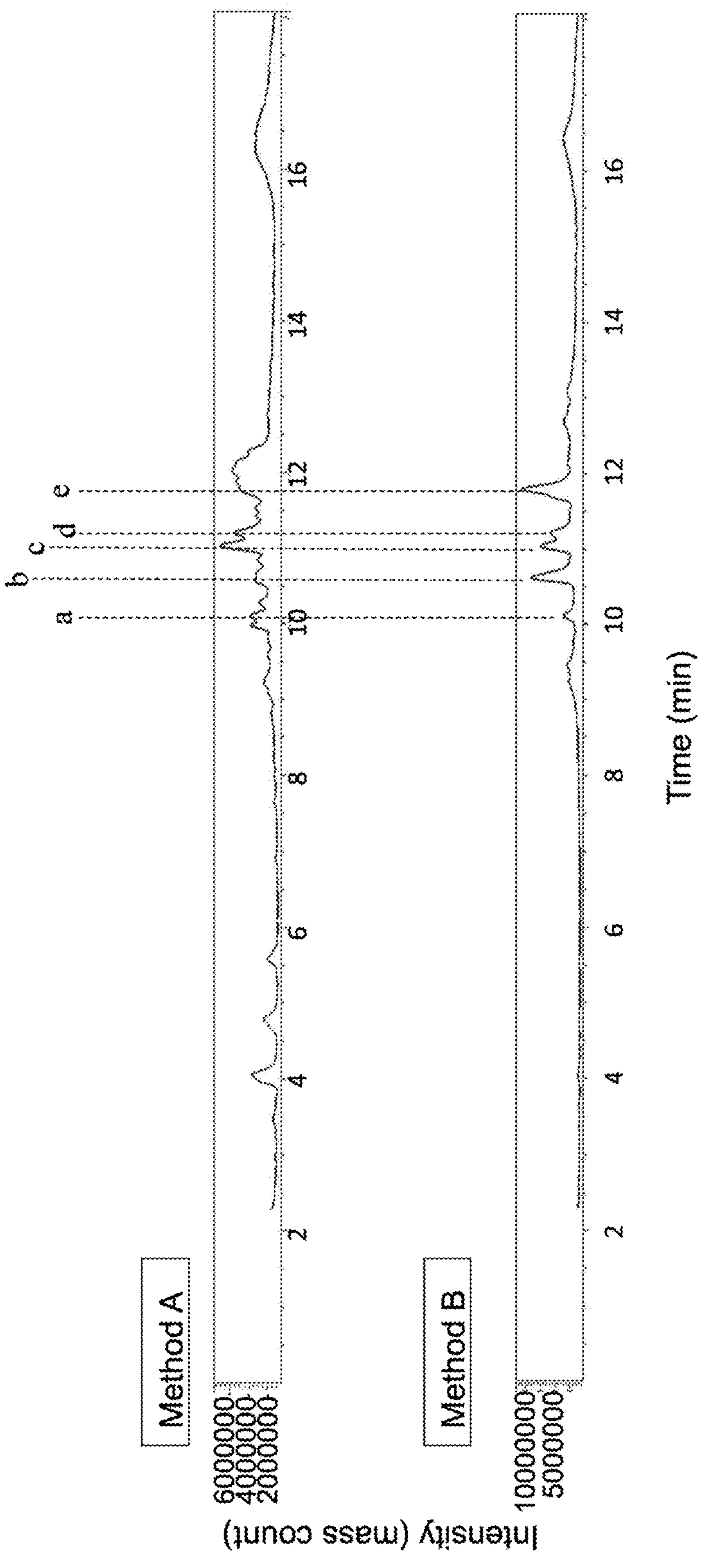
FIG. 1 shows a total ion chromatograph of LC-MS of Method A and Method B for functionalizing C-terminal arginine peptides with CHD-$PEG_3$-azide: a.) tetramethylguanidine-$PEG_3$-azide, side-product from synthesis; b.) internal control peptide lacking C-terminal arginine (Ac-AFAVA); c.) Remaining reagent (CHD-$PEG_3$-azide; [3]); d.) unoxidized reagent (CHO-$PEG_3$-azide; [2]); e.) Desired functionalized product (Ac-AFAVR-CHD-$PEG_3$-azide). Methods A and Bare described in the Examples below.

Reactions were prepared using two peptides—1 mM Ac-AFAVR (SEQ ID NO:1) reactive peptide and 1 mM Ac-AFAVA (SEQ ID NO:2) as an internal control peptide. CHD-$PEG_3$-azide was used at 10 mM effective concentration using either 0.2 M NaOH (aq.) or 2 M KPhos (aq.) for 1 hour. FIG. 1 is a total ion chromatograph of LC-MS of Method A and Method B for functionalizing C-terminal arginine peptides with CHD-$PEG_3$-azide. As shown in the LC-MS traces, Method B which utilizes milder conditions, resulted in generation of products with fewer observed side products as compared to Method A. In some cases, other CHD-orthogonal handle conjugation reagent conjugates can be made using the procedure described in Method B, such as with orthogonal handles containing mTet-PEGn-amine, methylcyclopropene-PEGn-amine, etc. (wherein it is an integer). The mild reaction conditions for causing the CHD to react with an arginine residue provided herein can be highly advantageous and are especially useful for less stable and/or base labile molecules, such as when using a conjugation reagent that contains an additional reactive handle that is not stable under the stronger base conditions, i.e. pH above 13.5.

Peptides that were successfully functionalized with DTB (desthiobiotin) and subsequently CHD-orthogonal handle conjugation reagents were then affinity enriched using streptavidin-bearing beads. The peptides were incubated with the bead and washed to remove excess/unreacted CHD-PEG-azide and impurities. On-bead DNA-peptide conjugate (peptide—conjugation reagent—nucleic acid conjugate) formation was carried out using a solution of DBCO-DNA (Dibenzocyclooctyne-coupled DNA; DNA=5'-/5Phos/CAA GTT CTC AGT AAT GCG TAG/DBCOdT/CC GCG ACA CTA G-3; SEQ ID NO: 3) and incubating for 16 hours. The beads containing the conjugated product were washed to remove excess DBCO-DNA. The beads were then washed with 4 mM biotin, 20 mM Tris-HCl, and 50 mM NaCl to elute the conjugates off of the streptavidin beads. The solution containing the desired conjugates was barcoded with 1× Quick Ligase reaction buffer, and 1× Quick ligase enzyme. WO2017/192633. Using this procedure, barcoded DNA-peptide conjugates were prepared for use in a protein analysis assay (e.g., using DNA encoding).

Example 3. Assessment of Conditions for CID Arginine Modification

This example describes the assessment of various conditions including buffers, pH, and temperature for CHD modification of peptides with at least one arg residue.

Methods for linking a CH-D-containing conjugation reagent to an arginine residue in a peptide are known, but require conditions that are relatively harsh. Milder conditions are needed to make this reaction useful in the context of complex molecules and biochemical mixtures. In the CHD-arginine reaction, it is reasonable to hypothesize that the formation of the dihydro adduct is the fast step, while the dehydration step followed by the 1,2-alkyl shift is likely to be the rate limiting step. To facilitate the reaction at a lower pH, a combination of a high ionic strength buffer and a moderately high heat was used to drive the dehydration step. After selecting a candidate buffer system, the reaction conditions were further optimized to identity improved conditions.

An array of high ionic strength buffers (0.1-4M) with a pH ranging from neutral to strongly basic (pH 7-13) were tested. Two levels of reaction temperature (37° C. and 70° C.) were initially tested. In order to quantitatively determine the reaction yield, an arginine-free peptide was introduced to the CHD/arginine peptide mixture as an internal control for LCMS analysis. The reaction under standard NaOH condition was used as the 100% reference for data analysis.

Alkaline Buffer Screening

In a 96-well PCR plate, a 20 μL reaction containing the peptide mixture (Ac-AFAVR(SEQ ID NO:1) and Ac-AFAVA (SEQ ID NO:2), 1 mM each), 10 mM CHD, and various reaction buffers were incubated in a Thermocycler at 37° C. for 1 h. A duplicate plate was incubated at 70° C. for 1 h. After reaction, the samples were diluted and analyzed by LCMS. Molecular mass peaks correspond to Ac-AFAVR, Ac-AFAVA, and dehydrated imidazolidinone products were integrated and analyzed to calculate the reaction yield, with the product yield at standard condition of 0.2M NaOH at 37° C. for 1 h as 100%.

TABLE 1

Screening of CHD-arginine reaction conditions

| Condition | Buffer | Concentration (M) | pH | Temperature (C.) | Yield (%) |
|---|---|---|---|---|---|
| 1 | MOPS | 0.8 | 7 | 70 | 16.1% |
| 2 | MOPS | 0.8 | 7 | 37 | 0.0% |
| 3 | HEPES | 1 | 7 | 70 | 41.6% |
| 4 | HEPES | 1 | 7 | 37 | 3.8% |
| 5 | KPhos | 1 | 7 | 70 | 52.0% |
| 6 | KPhos | 1 | 7 | 37 | 4.0% |
| 7 | SSC | 20× | 7 | 70 | 16.5% |
| 8 | SSC | 20× | 7 | 37 | 2.9% |
| 9 | PIPES | 0.5 | 7.2 | 70 | 40.9% |

TABLE 1-continued

Screening of CHD-arginine reaction conditions

| Condition | Buffer | Concentration (M) | pH | Temperature (C.) | Yield (%) |
|---|---|---|---|---|---|
| 10 | PIPES | 0.5 | 7.2 | 37 | 1.5% |
| 11 | PBS | 1× | 7.4 | 70 | 3.3% |
| 12 | PBS | 1× | 7.4 | 37 | 12.9% |
| 13 | PBS | 10× | 7.4 | 70 | 32.4% |
| 14 | PBS | 10× | 7.4 | 37 | 1.1% |
| 15 | KPhos | 2 | 7.45 | 70 | 79.3% |
| 16 | KPhos | 2 | 7.45 | 37 | 7.8% |
| 17 | TAPS | 0.5 | 7.9 | 70 | 6.9% |
| 18 | TAPS | 0.5 | 7.9 | 37 | 0.0% |
| 19 | HEPES | 0.5 | 8 | 70 | 52.5% |
| 20 | HEPES | 0.5 | 8 | 37 | 3.5% |
| 21 | DAP | 1 | 8 | 70 | 37.1% |
| 22 | DAP | 1 | 8 | 37 | 6.7% |
| 23 | $NaHCO_3$ | 1 | 8 | 70 | 81.9% |
| 24 | $NaHCO_3$ | 1 | 8 | 37 | 77.1% |
| 25 | Borate | 0.5 | 8.6 | 70 | 8.8% |
| 26 | Borate | 0.5 | 8.6 | 37 | 0.9% |
| 27 | Borate | 2 | 8.6 | 70 | 3.6% |
| 28 | Borate | 2 | 8.6 | 37 | 0.7% |
| 29 | NaOAc | 1 | 8.8 | 70 | 31.0% |
| 30 | NaOAc | 1 | 8.8 | 37 | 2.4% |
| 31 | Borate | 0.5 | 9 | 70 | 5.2% |
| 32 | Borate | 0.5 | 9 | 37 | 1.1% |
| 33 | $Na_2B_4O_7$ | 0.1 | 9.4 | 70 | 13.9% |
| 34 | $Na_2B_4O_7$ | 0.1 | 9.4 | 37 | 1.2% |
| 35 | $K_2HPO_4$ | 1 | 9.3 | 70 | 94.7% |
| 36 | $K_2HPO_4$ | 1 | 9.3 | 37 | 24.6% |
| 37 | $Na_2HPO_4$ | 1 | 9 | 70 | 0.0% |
| 38 | $Na_2HPO_4$ | 1 | 9 | 37 | 0.0% |
| 39 | Borate | 0.5 | 9.5 | 70 | 11.6% |
| 40 | Borate | 0.5 | 9.5 | 37 | 0.7% |
| 41 | Imidazole | 1 | 9.5 | 70 | 55.4% |
| 42 | Imidazole | 1 | 9.5 | 37 | 10.8% |
| 43 | $LiClO_4$ | 2 | 9.9 | 70 | 5.5% |
| 44 | $LiClO_4$ | 2 | 9.9 | 37 | 0.0% |
| 45 | CAPS | 0.5 | 10 | 70 | 87.0% |
| 46 | CAPS | 0.5 | 10 | 37 | 44.3% |
| 47 | $Na_4P_2O_2$ | 0.2 | 10.5 | 70 | 90.4% |
| 48 | $Na_4P_2O_2$ | 0.2 | 10.5 | 37 | 35.7% |
| 49 | CBC | 0.4 | 10.5 | 70 | 96.4% |
| 50 | CBC | 0.4 | 10.5 | 37 | 85.5% |
| 51 | $Na_2CO_3$ | 1 | 11.2 | 70 | 90.3% |
| 52 | $Na_2CO_3$ | 1 | 11.2 | 37 | 85.5% |
| 53 | $Na_2CO_3$ | 0.5 | 11.2 | 70 | 88.7% |
| 54 | $Na_2CO_3$ | 0.5 | 11.2 | 37 | 83.1% |
| 55 | $K_2CO_3$ | 0.5 | 12 | 70 | 89.3% |
| 56 | $K_2CO_3$ | 0.5 | 12 | 37 | 82.8% |
| 57 | $K_2CO_3$ | 1 | 12 | 70 | 89.1% |
| 58 | $K_2CO_3$ | 1 | 12 | 37 | 84.1% |
| 59 | $K_3PO_4$ | 0.5 | 12.5 | 70 | 89.3% |
| 60 | $K_3PO_4$ | 0.5 | 12.5 | 37 | 87.4% |
| 61 | LiOH | 1 | 12.7 | 70 | 98.6% |
| 62 | LiOH | 1 | 12.7 | 37 | 95.0% |
| 63 | $K_3PO_4$ | 1 | 13 | 70 | 91.6% |
| 64 | $K_3PO_4$ | 1 | 13 | 37 | 90.0% |

While the reaction generally proceeds to a better yield in higher pH buffers at low temperature (37° C.), several mildly to moderately basic buffer systems including sodium carbonate/bicarbonate (CBC) buffer, potassium phosphate (KPhos) buffer, CAPS, and sodium pyrophosphate were shown to generate high reaction yield at 70° C. (Table 1). In particular, reaction in potassium phosphate buffer pH 7.45 was observed to produce a 79% yield, but gives a near quantitative conversion at pH 9.3.

Potassium Phosphate Buffer Optimization

The reaction conditions using the potassium phosphate buffer system were further optimized. In PCR tubes, 20 μL reactions containing the peptide mixture (1 mM each), CHD (10 mM), and potassium phosphate buffer pH 8.3 (1 M or 2M) were incubated at various temperatures (40, 60 and 80°

C.) for various lengths of time (30, 60 and 90 min). After the reaction completion, the reactions were quenched with 10 μL 10% TFA and analyzed by LCMS. As shown in Table 2, two CHD-arginine reaction conditions (Condition 5 and 11) that are capable of yielding near quantitative conversion of the stable dehydrated imidazolidinone product were identified. Thus, favored embodiments of reaction conditions for the method of the invention comprise a reaction temperature of 70-90° C., preferably about 80° C.; a phosphate buffer, preferably potassium phosphate at a concentration of about 1-2 M; and a reaction time of 30-90 minutes, commonly about 60 to 90 minutes.

TABLE 2

Optimization of CHD-arginine reaction conditions in KPhos buffers, pH 8.3

| Condition | Temperature (C.) | KPhos Concentration (M) | Time (min) | Yield |
|---|---|---|---|---|
| 1 | 40 | 1 | 30 | 1.07% |
| 2 | 40 | 1 | 90 | 4.44% |
| 3 | 60 | 1 | 60 | 29.59% |
| 4 | 80 | 1 | 30 | 70.06% |
| 5 | 80 | 1 | 90 | 100.83% |
| 6 | 40 | 2 | 60 | 8.01% |
| 7 | 60 | 2 | 30 | 40.29% |
| 8 | 60 | 2 | 60 | 62.37% |
| 9 | 60 | 2 | 60 | 55.16% |
| 10 | 60 | 2 | 90 | 65.41% |
| 11 | 80 | 2 | 60 | 98.46% |

The significant reduction of the CHD-arginine reaction buffer pH provides the benefit of preserving critical base sensitive functional groups. It has been understood that reactive bioorthogonal handles such as tetrazines and protein post-translational modifications (PTM) such as serine/threonine phosphorylation cannot survive the highly basic NaOH solutions previously used for the CHD-arginine reaction. Kemp, *FEBS LETTERS* (1980) 110(2):308-312; Boger et al., *J. Org. Chem.* (1985) 50(25): 5377-5379. Using the improved CHD reaction conditions of the invention, tetrazine and other base sensitive reactive handles can be present in a conjugation reagent that uses the CHD-arginine connection, and protein phosphorylation and other post-translational modifications (PTM) can be maintained in the target peptide(s). In some cases, the preservation of these critical functional groups allows further chemical modifications of the peptides of interest, and allows these biologically important PTMs to be analyzed in the downstream proteomic studies and applications.

Functional Molecule Stability Test

Figure 2A:
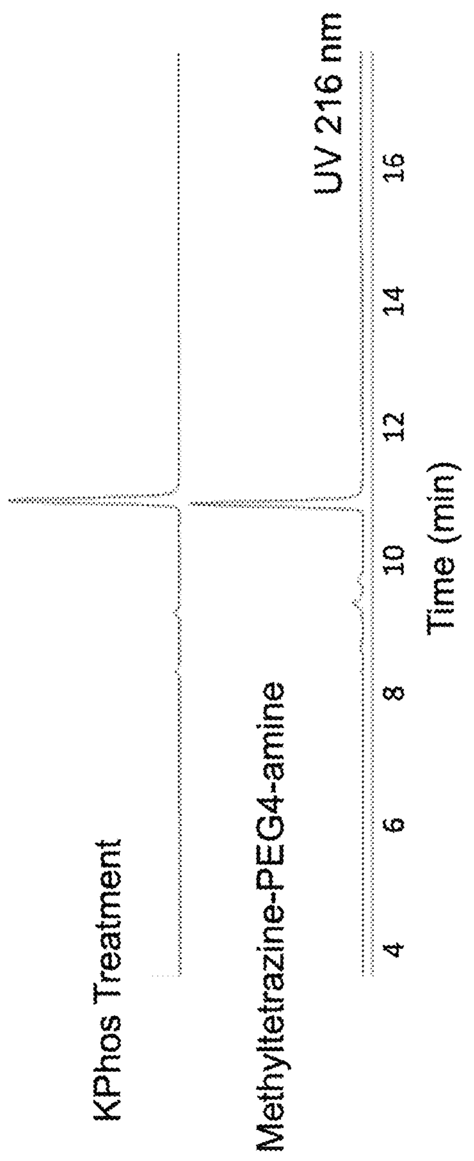
FIG. 2A shows LCMS traces from a methyltetrazine stability test in 1M KPhos pH 8.3, 80° C., 1.5 h.
Figure 2B:
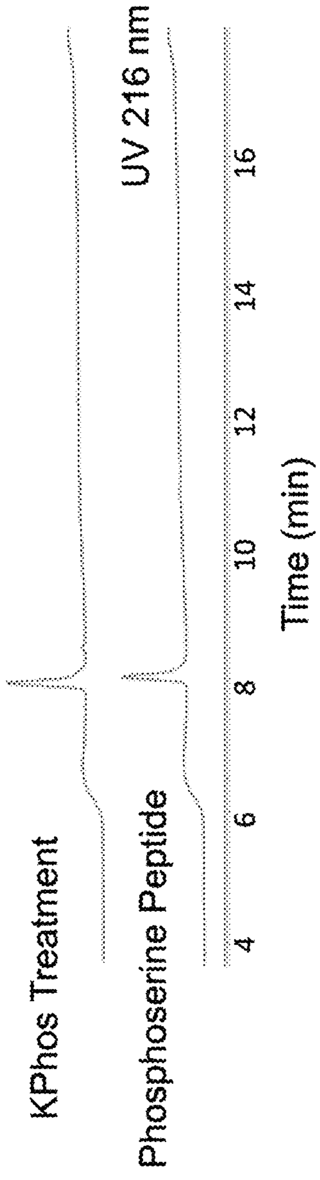
FIG. 2B shows LCMS traces from a phosphoserine stability test in 1M KPhos pH 8.3, 80° C., 1.5 h.
Figure 2C:
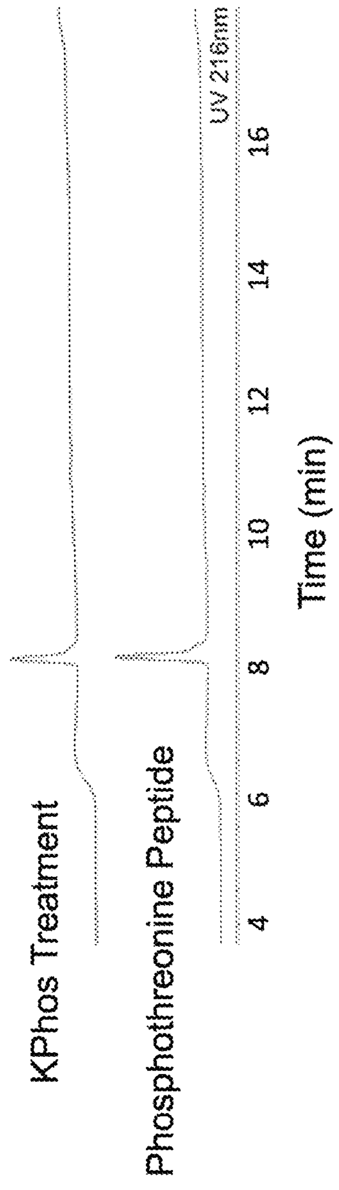
FIG. 2C shows LCMS traces from a phosphothreonine stability test in 1M KPhos pH 8.3, 80° C., 1.5 h.

The stability of various molecules of interest such as methyltetrazine and peptides with serine/threonine phosphorylation were tested in select conditions identified above utilizing potassium phosphate buffer. In 200 μL 1M KPhos buffer (pH 8.3), 1 mM molecule of interest (methyltetrazine-$PEG_4$-amine, Ac-ADWApSGQ (SEQ ID NO:4), Ac-ADWApTGQ (SEQ ID NO:5)) was added and the mixture was heated to 80'C for 1.5 h. After the reaction, the mixture was analyzed by LCMS and compared to the starting material. As shown in FIG. 2A-2C which shows non-treated starting material in the bottom, the molecules treated with the tested conditions (top) were observed to be stable.

Example 4. Peptide Sample Preparation Workflow for ProteoCode™ Assay and Assessment of DNA Encoding This example demonstrates an exemplary sample preparation workflow used for preparing peptides using the CHD-orthogonal handles described above. The exemplary workflow depicted in FIG. 3 outlines preparation of CHD-labeled and DNA-coupled peptides starting from an unpurified proteomic sample. This example also describes assessing and using the prepared peptides in a ProteoCode™ assay which utilizes DNA encoding.

Protein Denaturation and Digestion:

For a 10 μg protein sample, the sample was diluted to the desired protein input concentration in NHS-DTB (N-hydroxysuccinimide-desthiobiotin) buffer (10 ug/45 μL; 100 mM Carbonate/Bicarbonate buffer pH 9, 2% sodium deoxycholate (SDC)), 0.5 M TCEP (stock solution) was added for a final concentration of 5 mM TCEP. Samples were incubated for 15 min at 37° C. After cooling, sufficient 0.5 M iodoacetamide (IAA) stock was added for a final concentration of 20 mM, Samples were incubated at 37° C. for 15 min to allow the alkylation to proceed, then 100 mM NHS-DTB stock was added to each sample for a final concentration of 10 mM NHS-desthiobiotin, and incubated for 1 hour at 60° C. One volume of 1 M Tris, pH 7.4 was added to quench excess, unreacted NHS. Trypsin was added at a 1:25 ratio, by mass, for each sample and incubated for 2 hrs. at 37° C. to digest the sample. Acidification Solution (50%/o acetonitrile, 2% formic acid in high purity water) was added and the samples were centrifuged to pellet insoluble material (precipitated SDC) and the supernatant was kept.

Purification of Peptides:

200 μL digested protein sample was purified away from salts and excess reagents using: PreOmics® PHOENIX™ columns, SCX (strong cation exchange) columns, SEC (size-exclusion chromatography), SPE (solid-phase extraction) columns, centrifugal filters, desalting columns, reverse phase LC, physisorption methodologies, and other suitable scavenger beads/resins can also be used.

CHD Functionalization of C-Terminal Arginines

Each sample was resuspended after concentration in vacuo in 20 μL 0.2 M NaOH (pH 13.7), 1 M KPhos (pH 8.3), or 2 M KPhos (pH 8.3). CHD [3] Stock (CHD-$PEG_3$-azide in DMSO) was added for a final concentration of 10 mM and incubated at 37° C. for 1 hr, 80° C. for 1.5 hours, or 80° C. for 1 hour. The reaction was neutralized by adding equal volume 1 M Tris, pH 7.4. Diluted samples to 10 μg/1000 μL PBS-T (PBS (phosphate-buffered saline) plus 0.1% TWEEN® 20).

Streptavidin Bead Capture, and Conjugate Formation

Streptavidin beads were prepared (washed 3× with PBS-T) and added to the sample with rotation to allow for streptavidin bead binding. After the incubation period, samples were washed twice with 200 μL PBS-T and resuspended in 10 μL of 125 uM DBCO-DNA in 100 mM HEPES pH 7.4, 0.1% TWEEN® 20, 2M NaCl. The samples were incubated with rotation at 37° C. overnight (16-18 hours).

Sample Barcoding

[1] Upon completion of incubation, beads were centrifuged and washed to remove any excess DBCO-DNA, Sample barcodes were added and beads were washed twice with 200 μL PBS-T. The peptide-DNA conjugates were eluted with 10 μL 4 mM biotin, 20 mM Tris-HCl, and 50 mM NaCl, Conjugate formation and barcoding were confirmed by loading 0.5 μL of sample (5 pmol) on TBU gel electrophoresis. (15% TBU gel, 200V, 50 min). Various peptides (e.g. protein based, some rationally designed for assay) were treated using this exemplary workflow, including peptides shown in Table 3. The peptides were then immobilized on a solid support (beads; NHS-Activated Sepharose High Performance, Cytiva, USA). The DNA of the peptide-DNA conjugates was hybridized and ligated to capture DNAs containing a complementary sequence attached to beads at appropriate spacing and density (see e.g., US20200348308 A1). Briefly, the capture DNAs were conjugated to the beads using trans-cyclooctene (TCO) and methyltetrazine (mTet)-based click chemistry. TCO-modified short hairpin capture DNAs (16 base-pair stem, 4 base loop, 17 base 5' overhang) were reacted with mTet-coated beads. Phosphorylated nucleic acid-polypeptide conjugates (20 nM) were annealed to the hairpin DNAs attached to beads in 0.5 M NaCl, 50 mM sodium citrate, 0.02% SDS, pH 7.0, and incubated for 30 minutes at 37° C. The beads were washed once with PBST (1× phosphate buffer, 0.1% Tween 20) and resuspended in 1× Quick ligation solution (New England Biolabs, USA) with T4 DNA ligase. After a 30 min incubation at 25° C., the beads with immobilized peptide-DNA conjugates were washed once with PBST, three times with 0.1 M NaOH, 0.10% Tween 20, three times with 1× phosphate buffer, 0.1% Tween 20, and resuspended in 50 μL of PBST.

TABLE 3

Peptides Sequences

| SEQ ID NO: | Peptide Sequence |
|---|---|
| 6 | FSGVARGDVRGGK(azide)-$NH_2$ |
| 7 | AFSGVARGDVRGGK(azide)-$NH_2$ |
| 8 | SAFSGVARGDVRGGK(azide)-$NH_2$ |
| 9 | LAESAFSGVARGDVRGGK(azide)-$NH_2$ |
| 10 | ALAESAFSGVARGDVRGGK(azide)-$NH_2$ |
| 11 | EALAESAFSGVARGDVRGGK(azide)-$NH_2$ |

ProteoCode™ Assay

After the peptide-DNA conjugates prepared using the exemplary workflow described above were immobilized on a solid support, ProteoCode™ peptide analysis assay was performed. In the assay, peptides with associated DNA recording tags were contacted with binding agents each conjugated with a nucleic acid coding tag containing identifying information regarding the associated binding agent. Binding agents configured to recognize chemically modified phenylalanine (F) and leucine (L) as the N-terminal amino acid (NTAA) were used. If binding agent binds its cognate NTAA residue of the peptide, and affinity of the binding agent to the immobilized peptide is strong enough (typically, Kd should be less than 500 nM, and preferably, less than 200 nM), the coding tag associated with the binding agent and the recording tag associated with the peptide form hybridization complex via hybridization of the corresponding spacer regions to allow transfer of identifying information from the coding tag to the recording tag via a primer extension reaction (encoding reaction), generating extended recording tag. The ProteoCode™ assay also includes modification (e.g., functionalization) and elimination of the NTAA of peptides using a chemical reagent diheterocyclic methanimine in each cycle. Three cycles of encoding (information transfer from coding tags to recording tags) with two elimination cycles in between were performed. Elimination of the NTAA exposed a new NTAA available for recognition by a binding agent provided in the next cycle. Sequencing of extended recording tags after one or more encoding cycles is used to identify binding agent(s) that was (were) bound to the immobilized peptide. At the same time, estimating fractions of the recording tags being extended (encoded) during primer extension reaction (designated as Fraction of RT reads encoded, see FIG. 4A and FIG. 4B) provides estimate of efficiency of the encoding reaction, which directly correlates with binding affinity of the binder to the peptide.

Figure 4A:
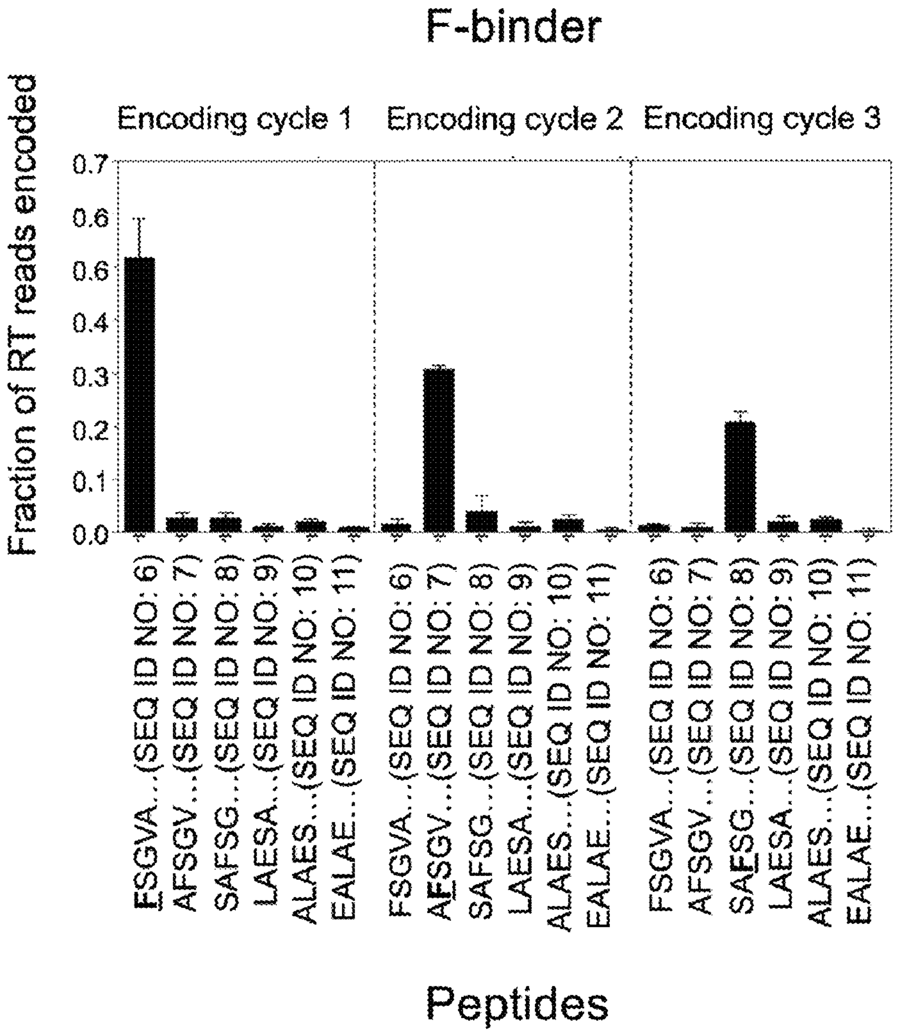
FIG. 4A-4B depicts results from a polypeptide analysis assay (ProteoCode™ assay) performed on CHD-treated peptides. The assay was performed using a phenylalanine binding agent (F-binder.
Figure 4B:
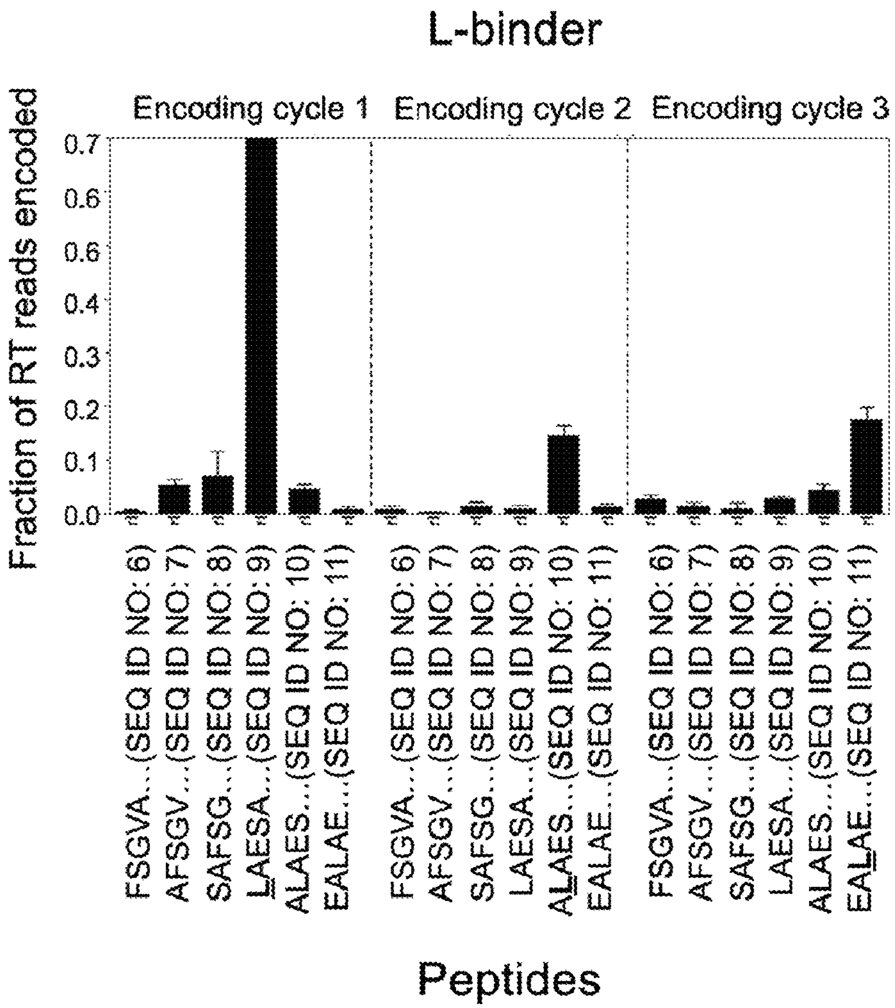

After completion of the binding, encoding, functionalization and elimination cycle(s), the extended recording tags were capped with an adapter sequence, subjected to PCR amplification, and analyzed by next-generation sequencing (NGS). FIG. 4A-4B shows chemistry cycle-dependent encoding efficiency with the mod-F-binder (FIG. 4A) and mod-L binder (FIG. 4B). Data on six F and L containing peptides are shown, in which either the F or L residue is stepped through the first 3 positions of the peptide. As shown in the data, as each successive residue was eliminated, an N-terminal modified F or L residue was exposed on one of the peptides and detected by the corresponding mod-F or mod-L binder with concomitant DNA encoding. In summary, peptides modified using the CHD reagents described and prepared with the exemplary workflow resulted in observed multicycle encoding using binding agents recognizing various NTAA as elimination of such NTAAs occurred.

Example 5. Exemplary CHD Fluorogenic Probes and Uses

This example describes the generation and use of three exemplary CHD fluorogenic probes in a protein sample preparation workflow for forming DNA-peptide conjugates.

CHD fluorogenic probes represent a class of functional CHD derivatives that are capable of generating an enhanced fluorescent signal upon the removal of a fluorescence quencher.

1,2,4,5-tetrazines have a broad UV absorption spectrum centered at around 530 nm, and are therefore capable of quenching a variety of fluorescent probes through Förster resonance energy transfer (FRET) or through-bond energy transfer (TBET), making tetrazines an attractive quenching functional group (e.g., Wieczorek et al., Chen Sci. (2017) 8(2): 1506-1510; Devaraj et al., *Angew. Chem. In. Ed.*, (2010) 49(16), 2869-2872; Lee et al., *J. Am. Chem. Soc.* (2018) 140, 3, 974-983). Furthermore, tetrazines can undergo rapid bioorthogonal reactions with its dienophile partners via an inverse electron demand Diels-Alder (iEDDA) mechanism. This generates an enhanced fluorescence upon the elimination of the quenching effect of the tetrazine (e.g., Blackman et al., *J. Am. Chem. Soc.* (2008) 130, 41, 13518-13519; Kang et al., *Proteome Sci.*, (2016) 15, 15; Devaraj et al., *Acc. Chem. Res.*, (2011) 44(9)-816-827). The increased fluorescent signal can be detected to approximate the reaction kinetics of conjugate formation, allowing for quantitative assessment of conjugate formation reaction as the reaction progresses.

During a ProteoCode™ sample preparation workflow, proteins are chemically treated and digested with trypsin. The resulting peptides are anchored to a solid surface via appropriate chemical linkers. Their exposed C-terminal arginines are free to react with CHD fluorogenic probes using the improved CHD conditions herein. After the removal of excess CHD reagents, appropriate dienophile-substituted oligo DNAs are used to react with CHD fluorogenic probe-modified peptides to result in a fluorescence enhancement. Several exemplary CHD fluorogenic probes and their uses are described below (A-C). During the dienophile-substituted oligo DNA and peptide conjugation step, fluorescence with appropriate excitation/emission wavelengths is monitored, and a plateaued fluorescence signal indicates the completion of the conjugation reaction. The resulting oligo-peptide conjugates can be further eluted for the downstream applications.

A. Trifunctional Fluorogenic Tetrazine CHD Probes (Conjugation Reagents)

Scheme 1 depicts construction of a fluorogenic tetrazine-CHD probe using a trifunctional linker core such as protected lysine 1. Fluorophores such as NBD NHS ester 2 are attached to yield fluorescent lysine 3. Amino tetrazine 4 and CHD carboxylic acid 7 are step-wise conjugated to the trifunctional conjugation reagent through conventional amide coupling reactions. Fluorogenic tetrazine-CHD probe 8 tags the arginine peptides on bead surfaces for further conjugate formation and the resulting fluorescence enhancement is quantitatively detected using a fluorometer in real time (FIG. 5A).

Scheme 1. Synthesis of Fluorogenic mTet-CHD-NBD Probe

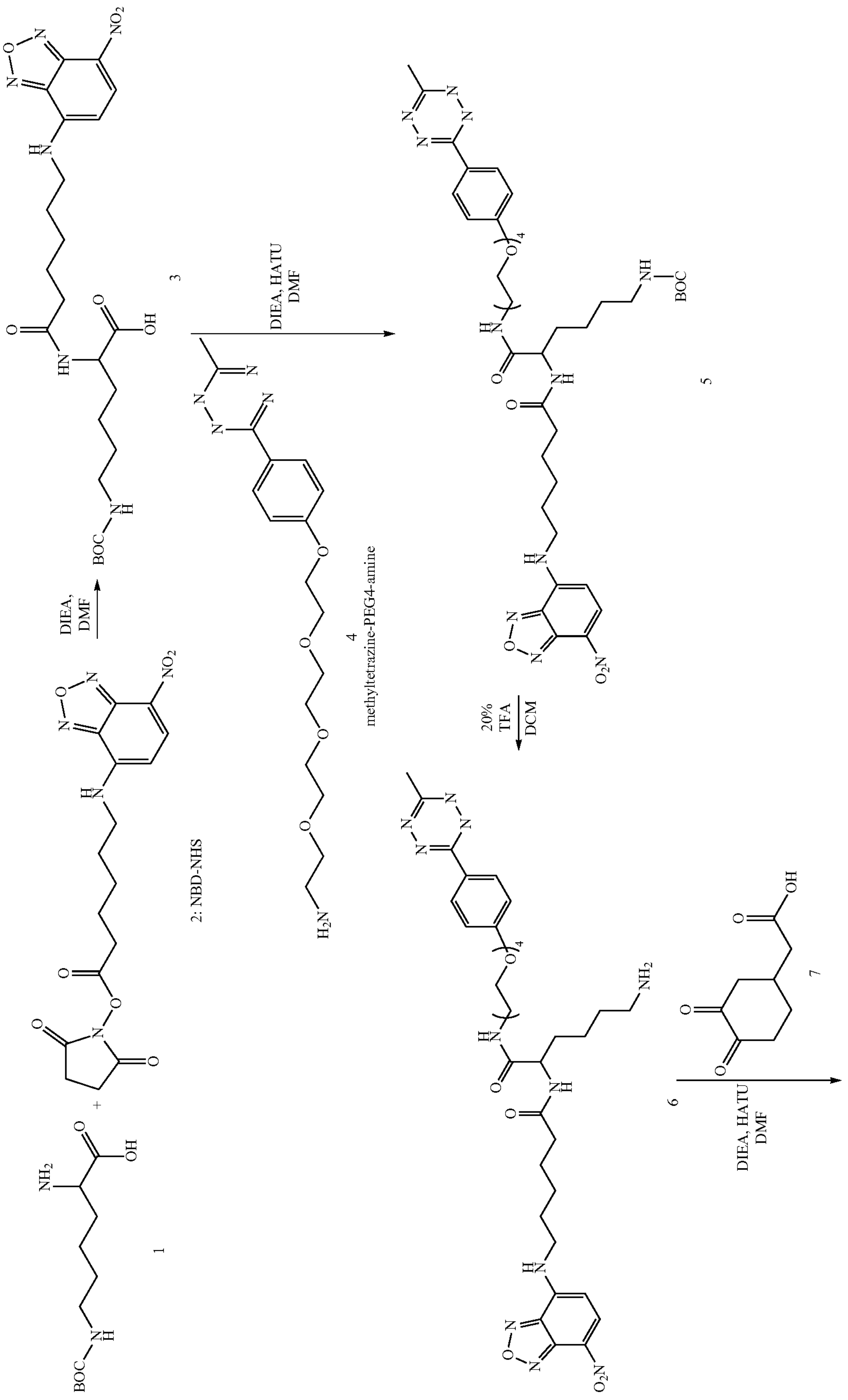
1
DIEA, DMF
2: NBD-NHS
3
DIEA, HATU DMF
4
methyltetrazine-PEG4-amine
5
20% TFA DCM
6
DIEA, HATU DMF
7

-continued
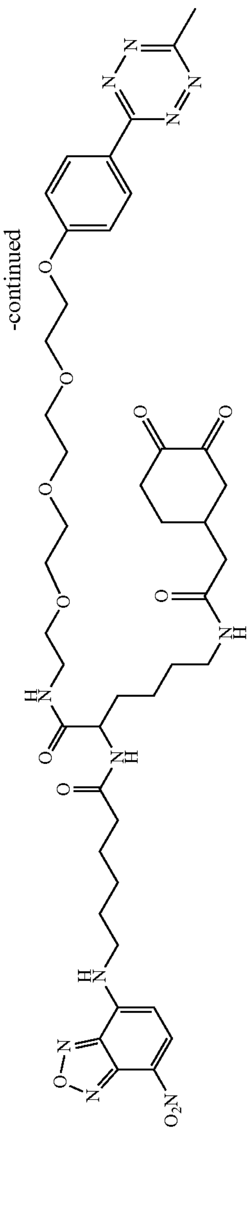
8
methyltetrazine-CHD-NBD

Fluorescence turn-on upon conjugate formation on bead surfaces using iEDDA chemistry includes the following as depicted in FIG. 5A: Step 1. Conjugation of metheptazine-CHD-fluorophore to peptides on the beads. Step 2. Conjugation of dienophile modified nucleic acids to fluorescence-quenched peptides anchored to the bead surface. Step 3. Enhanced fluorescent signals can be detected upon conjugate formation.

B. Dual-Quenched Fluorogenic Nucleic Acid Binding Probe for Highly Specific Conjugate Formation Detection Asymmetric cyanine dyes such as thiazole orange (TO) emit a strong fluorescence upon binding nucleic acids. When TO is conjugated to a tetrazine molecule, the fluorescence will only be turned on when the TO moiety binds the nucleic acids and the tetrazine moiety is removed. The dual-quenched probe is capable of completely "turning off" any fluorescent signal when nucleic acids and peptides are not conjugated, allowing for highly specific detection of the conjugate formation. Recent studies showed that by further chemically modifying the TO moiety, improved fluorescent turn-on can be achieved by significantly reducing the non-specific TO-nucleic acid interaction (Zhou et al., Chem. Sci., (2017) 8:7169-7173). One example of dual quenched fluorogenic probes is shown in Scheme 2 and FIG. 5B.

Scheme 2. Synthesis of Dual-Quenched Fluorogenic Nucleic Acid Binding Probe.

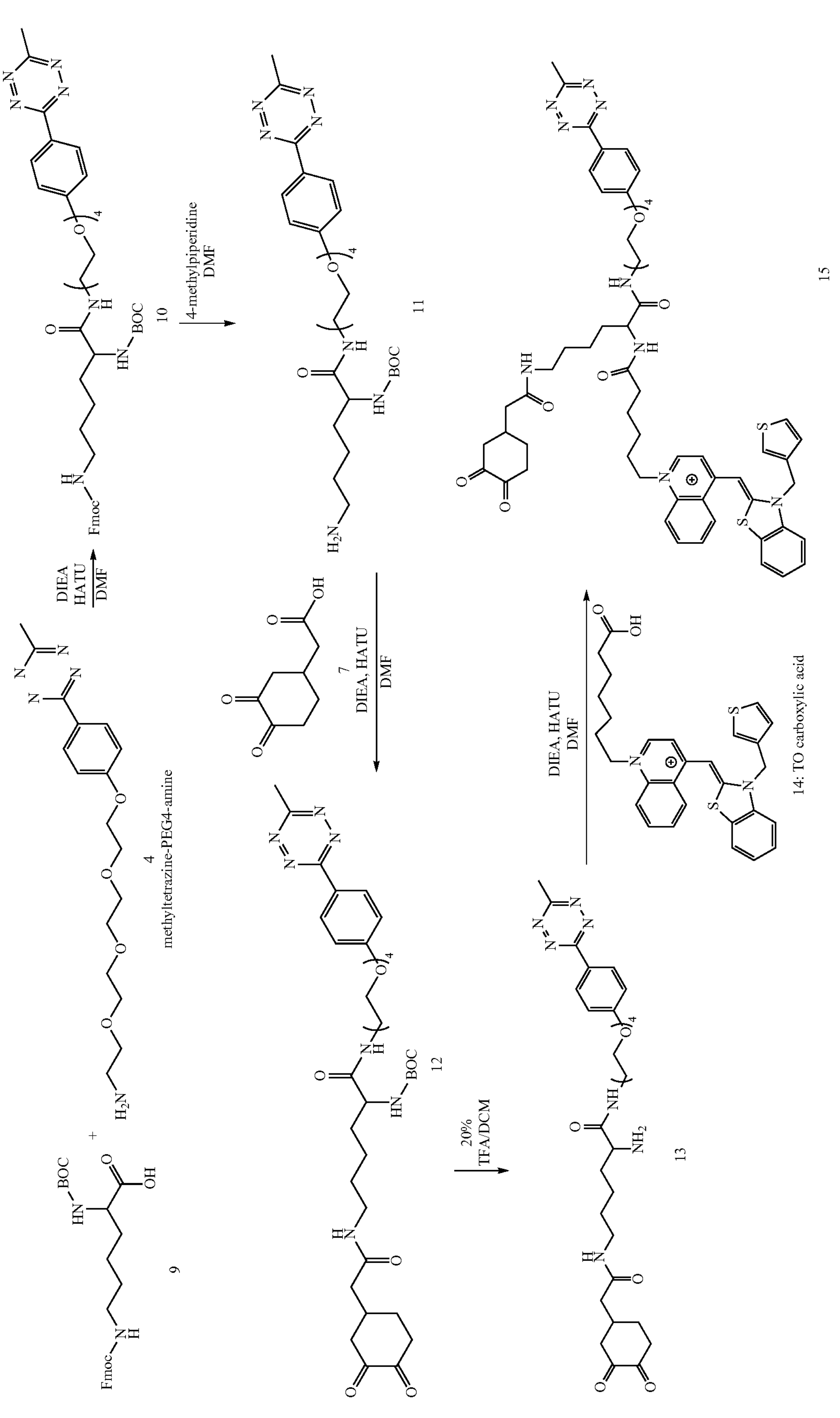
9
4
methyltetrazine-PEG4-amine
DIEA
HATU
DMF
10
4-methylpiperidine
DMF
11
7
DIEA, HATU
DMF
12
20%
TFA/DCM
13
14: TO carboxylic acid
DIEA, HATU
DMF
15

Fluorescence turn-on upon conjugate formation on the bead surface using a dual quenched nucleic acid binding probe includes the following as depicted in FIG. 5B: Step 1. Conjugation of methyltetrazine-CHD-TO to peptides on the beads. Step 2. Conjugation of dienophile modified nucleic acids to fluorescence-quenched peptides anchored to the bead surface. Step 3 Enhanced fluorescence upon the elimination of tetrazine and nucleic acid-TO binding for highly specific conjugate formation detection.

C. Click-to-Release Fluorogenic Tetrazine CHD Conjugation Reagent

Fluorescent probes are typically larger hydrophobic molecules with permanent charges, therefore, it may not be desirable to retain the fluorophore on the conjugate for extended periods of time as it may unnecessarily complicate the downstream assay. While different cleavable linker strategies exist to release the fluorescent reporter from the conjugate in a post-conjugation manner, a single-step, simultaneous release of the fluorescent probe upon the conjugation in a "click-to-release" fashion is preferred (van Onzen et al., J. Am. Chem. Soc. (2020) 142(25):10955-10963). One example of click-to-release fluorogenic tetrazine-CHD probes is shown in Scheme 3 and its schematic representation of fluorescent enhancement upon conjugation is provided in FIG. 5C.

Scheme 3. Synthesis of Click-to-Release Fluorogenic Tetrazine-CHD Probe.

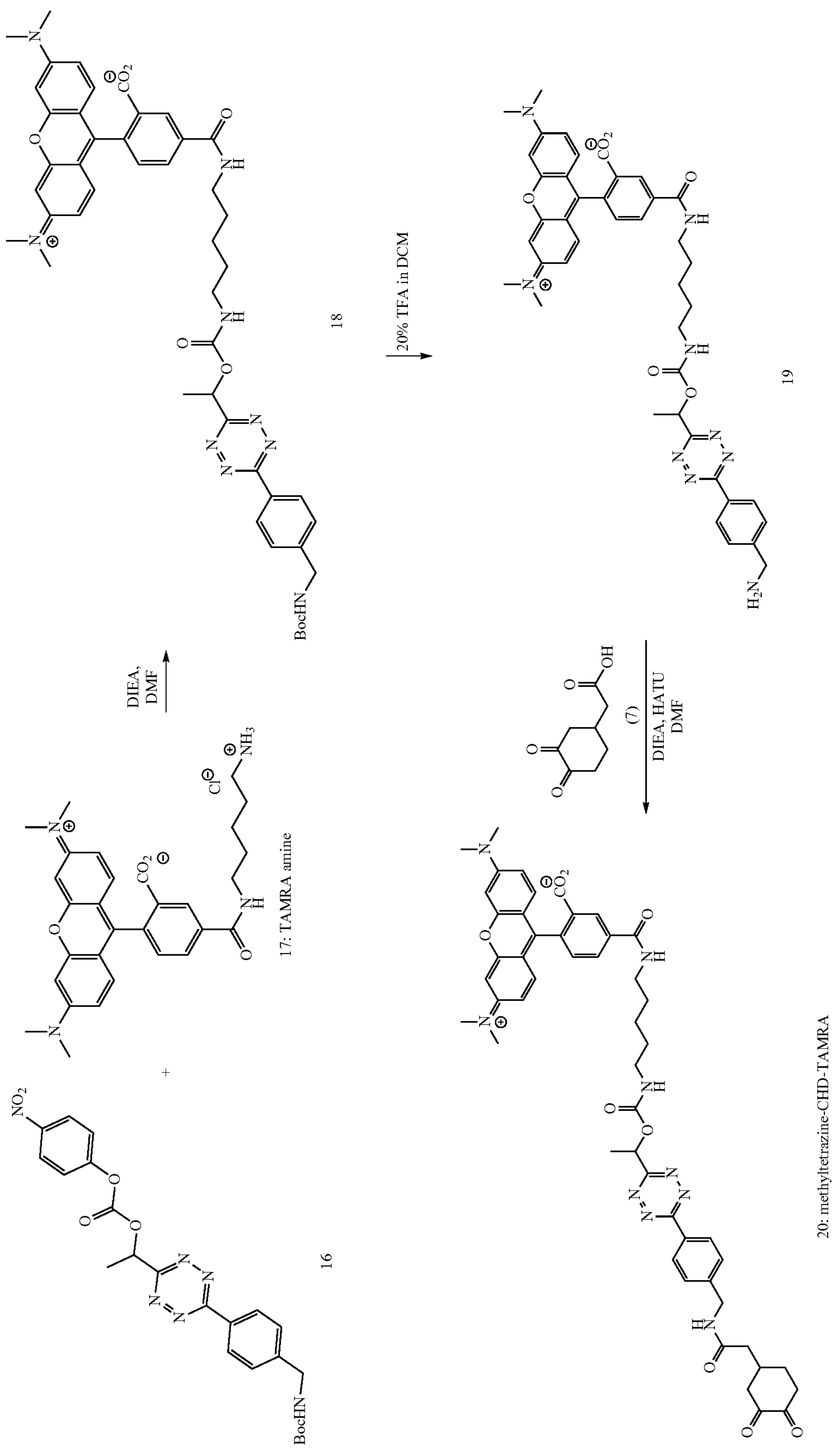
16
17: TAMRA amine
18
19
20: methyltetrazine-CHD-TAMRA

Fluorescence turn-on upon conjugate formation on the bead surface using click-to-release fluorogenic tetrazine probe includes the following as depicted in FIG. 5C: Step 1. Conjugation of mTet-CHD-fluorophore (TAMRA is shown as an example—see Scheme 3) to peptides on the beads. Step 2. Conjugation of dienophile modified nucleic acids to fluorescence-quenched peptides anchored to the bead surface. Step 3. Fluorophore released from the conjugate and the bead surface upon the formation of conjugate and an enhanced fluorescent signal is generated.

Example 6. Synthesis of methyltetrazine-TAMRA-CHD Conjugation Reagent

Step 1. Synthesis of Methyltetrazine-Amine-NHFmoc

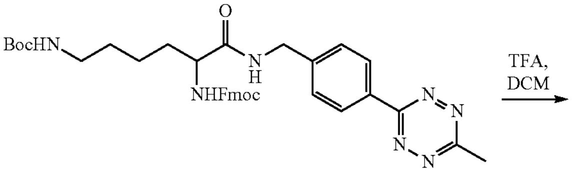

-continued

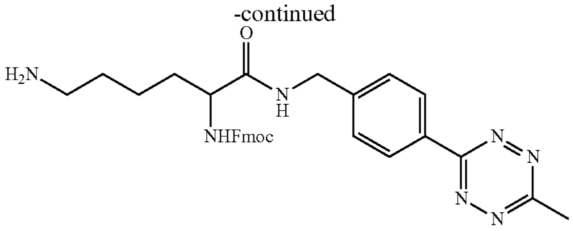

To a mixture of methyltetrazine-NHBoc-NHFmoc (325.5 mg, 0.5 mmol) in 10 mL DCM in a 20 mL scintillation vial equipped with a magnetic stirbar, 1.2 mL trifluoroacetic acid (TFA) was slowly added and the reaction was vigorously stirred at room temperature for 2 h and monitored by TLC (EtOAc:n-heptane=1:1). Upon the completion of the reaction, the solution was concentrated, and the crude mixture was added to 30 mL diethylether and pink precipitate immediately formed. The precipitate was collected by vacuum filtration to afford methyltetrazine-amine-NHFmoc as a pink powder (211 mg, 77% yield). The product was used for the next step without further purification.

Step 2. Synthesis of Methyltetrazine-TAMRA-NHFmoc

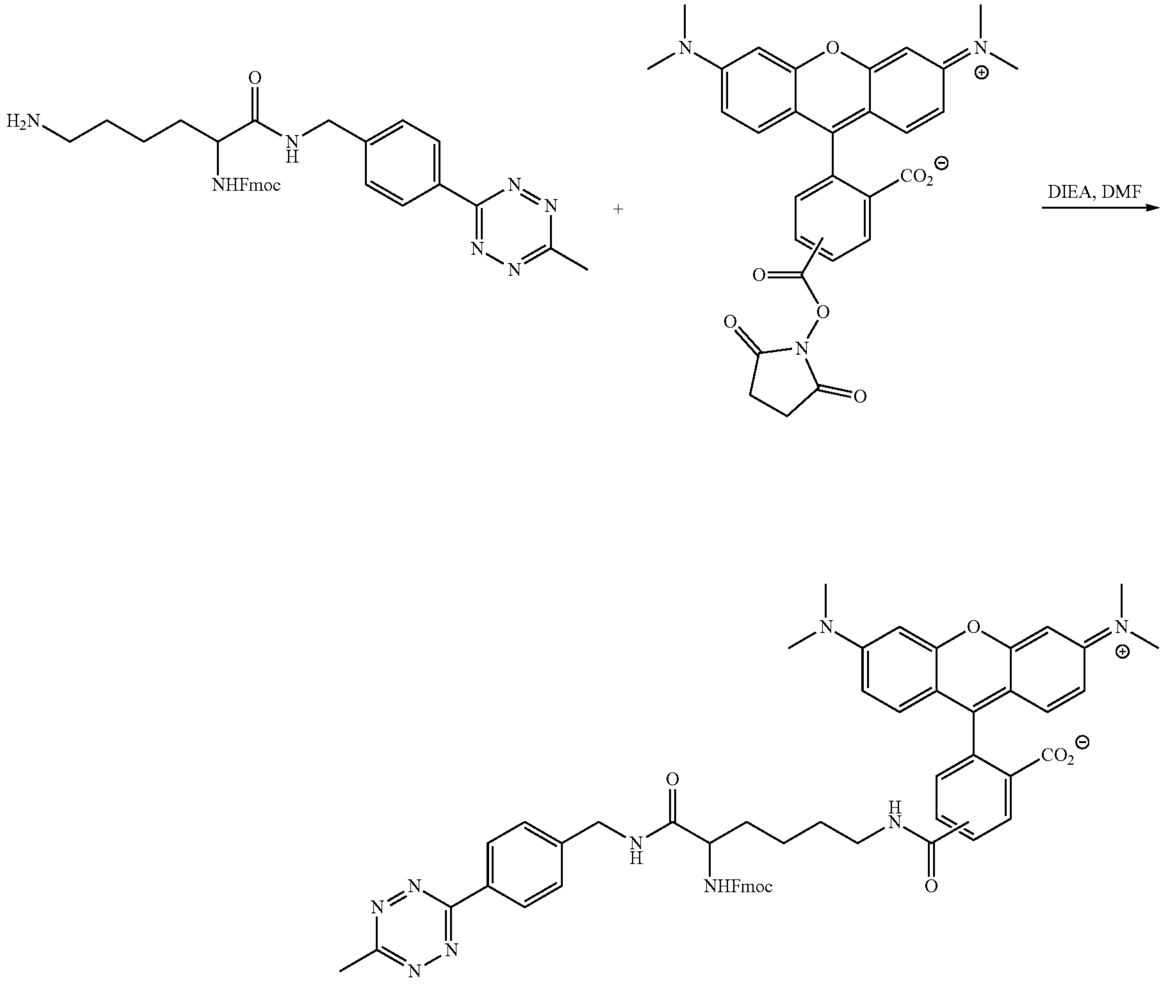

To a mixture of methyltetrazine-amine-NHFmoc (20 mg, 0.036 mmol) in 1 mM DMF in a 4 mL scintillation vial equipped with a magnetic stir bar, 5 equiv. of DIEA (diisopropyl ethyl amine, 31.5 μL, 0.181 mmol) was slowly added. 1.1 equiv, of 5(6)-TAMRA NHS Ester (21 mg, 0.040 mmol) in 1 mM DMF was added and the reaction was allowed at the room temperature for 1 h. The reaction was monitored by TLC (DCM:MeOH=20:1). Upon the completion of the reaction, the solution was concentrated, and the crude mixture was added to 30 mL diethylether and pink precipitate formed. The precipitate was centrifuged at 14,000 g for 10 min and the red pellets were collected and dried in vacuo to afford methyltetrazine-TAMRA-NHFmoc as a dark red solid (21 mg, 60% yield). The product was used for the next step without further purification.

Step 3. Synthesis of Methyltetrazine-TAMRA-Amine

To a mixture of methyltetrazine-TAMRA-NHFmoc in 4 mL DCM in a 20 mL scintillation vial equipped with a magnetic stir bar, 200 μL 4-methylpiperidine was added and the reaction was allowed at room temperature for 2 h and the reaction was monitored by TLC (DCM:MeOH=10:1). Upon the completion of the reaction, the solvent was removed, and the crude mixture was added to 30 mL diethylether and pink precipitate formed. The precipitate was centrifuged at 14,000 g for 10 min and the red pellets were collected and dried in vacuo to afford the product as a dark red solid (11 mg, 69% yield). The product was used for the next step without further purification.

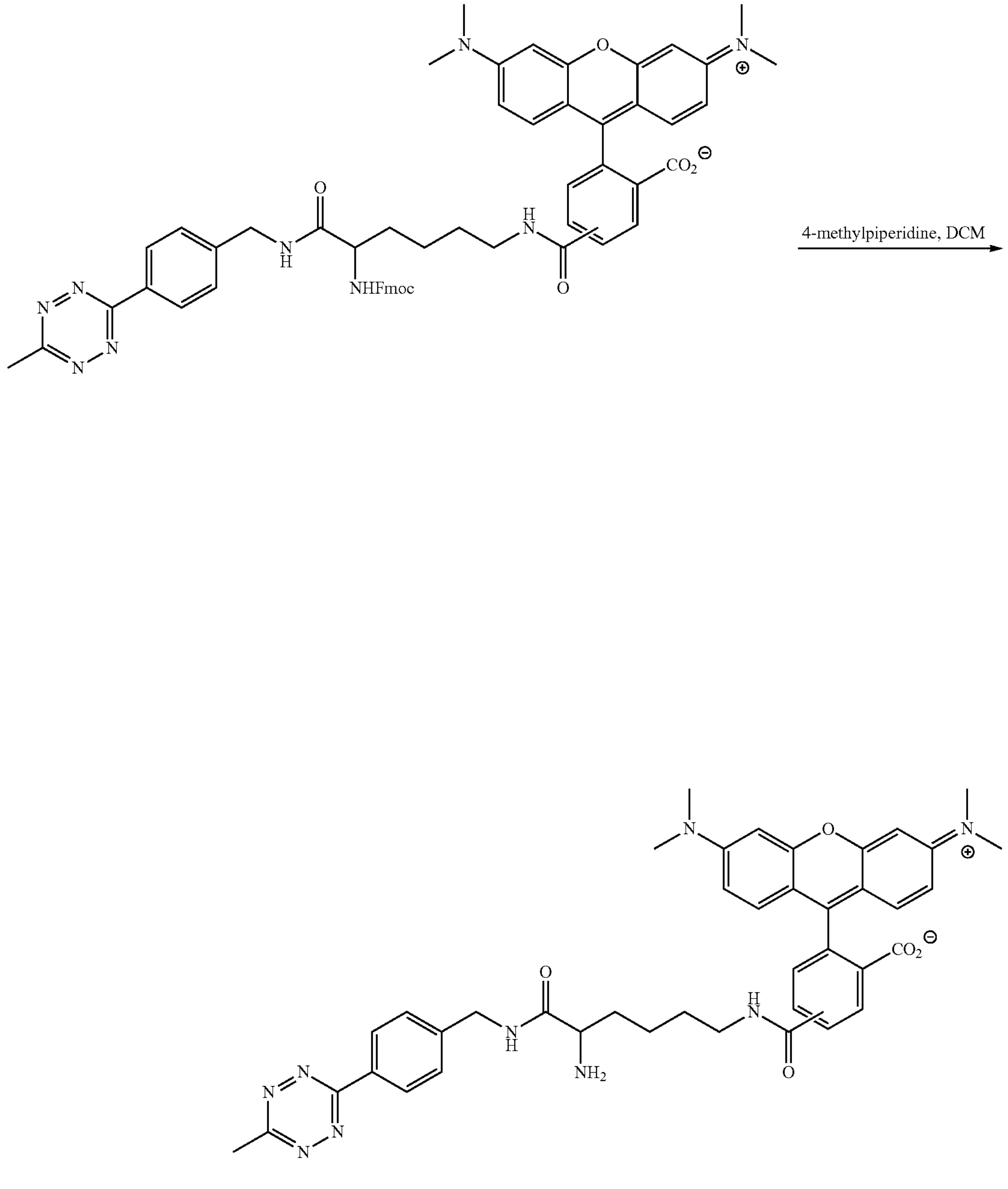

Step 4. Synthesis of Methyltetrazine-TAMRA-CHD Conjugation Reagent

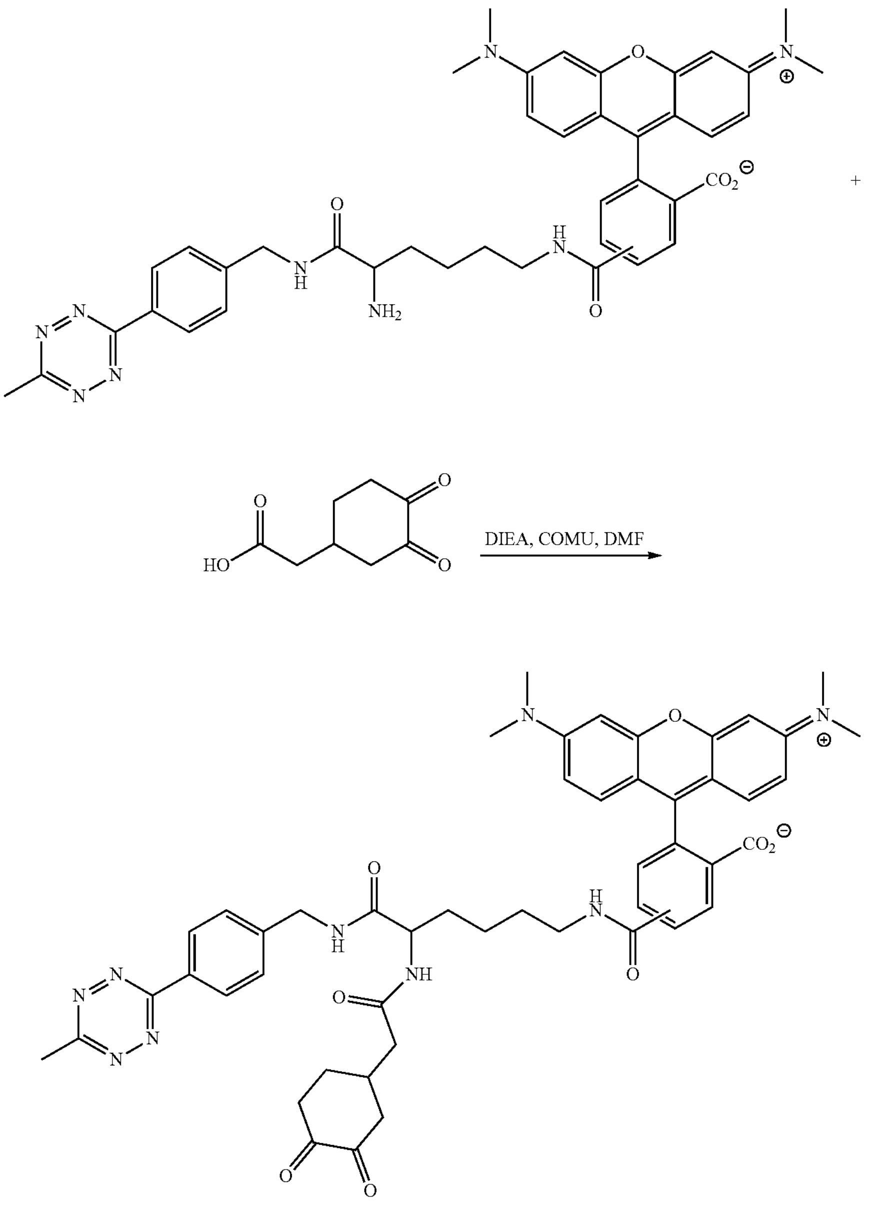

To a mixture of CHD-acid (2.8 mg, 0.016 mmol) in 0.5 mL DMF, 4 equiv. of DIEA (10 μL, 0.060 mmol) was slowly added to the mixture at 0° C., followed by the addition of 1.1 equiv. of COMU (7 mg, 0.016 mmol) in 0.5 mL DMF, The solution was stirred vigorously for 10 min at 0° C. Methyltetrazine-TAMRA-amine (11 mg, 0.0148 mmol) in 0.5 mL DMF was slowly added and the reaction was allowed to reach room temperature over 2 h and monitored by LCMS. HPLC gradient: 0 min-2 min 5% Phase B in Phase A, 2 min-12 min 50% a Phase B in Phase A to 95% Phase B, 12 min-15 min 95% Phase B, 15 min-18 min 0.5% Phase B in Phase A (Phase A:$H_2O$ with 0.1% formic acid, Phase B: ACN with 0.1% formic acid). The crude product was purified by HPLC to afford the methyltetrazine-TAMRA-CHD conjugate as a red powder (5.4 mg, 40.5% yield) Expected mass: 894.4, observed mass 893.8.

Example 7. Conjugation of Trans-Cyclooctene (TCO) to Amino DNA Oligonucleotide

DNA oligomer modified with Amino-Modifier C6dT (sequence: 5'-/5Phos/CAA GTT CTC AGT AAT GCG TAG/AmC6dT/CC GCG ACA CTA G-3', SEQ ID NO: 13) (a ssDNA referred to herein as HRT, 66 nmol) was dissolved in 250 mM TEAB (triethylammonium bicarbonate) buffer pH 8 for a final concentration of 0.2 mM. TCO-PEG4-NHS linker dissolved in DMSO was added to the solution for a final concentration of 20 mM. The reaction was incubated at 37° C. for 1 h. After the reaction, the TCO-modified DNA oligo were purified by acetone precipitation (3×) and the final concentration of the purified oligo was determined by NanoDrop 2000, 25.7 nmol of TCO oligo was collected for a 39% yield.

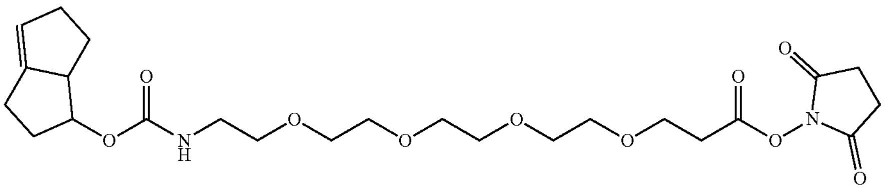

TCO-PEG4-NHS

Example 8. Nucleic Acid Labeling with a TAMRA Conjugation Reagent

Figure 6:
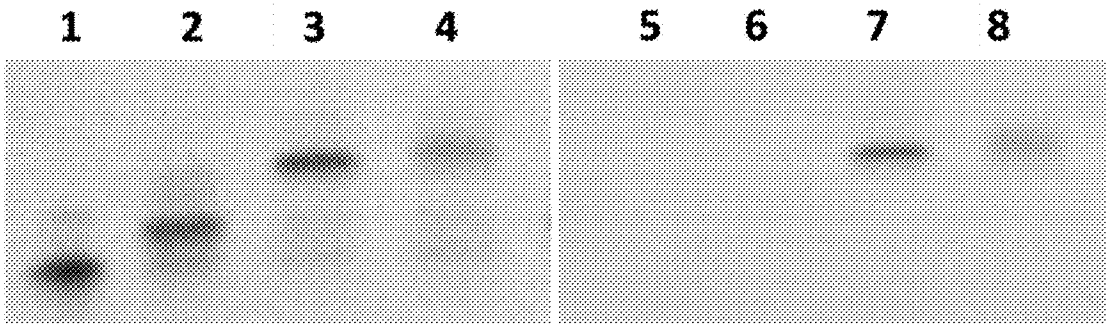
FIG. 6 shows the results of nucleic acid labeling with a TAMRA conjugation reagent as described in Example 8. Lanes 5-8 correspond to the oligonucleotide HRT alone (HRT, 34 nt); HRT-PEG4-TCO conjugate; HRT-PEG4-PEG4-TAMRA; and the HJRT-PEG4-TAMRA-CHD conjugate. Bands in lane 7 and lane 8 indicate successful conjugation of TAMRA-methyltetrazine probes to the TCO oligo. The gel was then stained with SYBR Gold to visualize all DNA on the gel (SYBR Gold, lane 1-4 correspond to HRT alone (HRT, 34 nt); HRT-PEG4-TCO conjugate; HRT-PEG4-PEG4-TAMRA; and the HRT-PEG4-TAMRA-CHD conjugate. The bands in lanes 3-4 demonstrate that the corresponding bands in lanes 7-8 contain nucleic acid as well as TAMRA.

TCO modified oligo was dissolved in 50 mM HEPES buffer pH 8 for a final concentration of 5 μM. TAMRA-PEG4-Methyltetrazine or methyltetrazine-TAMRA-CHD were added to a final concentration of 10 μM, The reaction was incubated at room temperature for 1 h and analyzed by PAGE analysis. The gel was firstly imaged by UV302 without any DNA staining reagents (detecting TAMRA): lanes 5-8. The gel was then stained with SYBR Gold to visualize all DNA on the gel (SYBR Gold, lanes 1-4). The results are shown in FIG. 6. Lanes 5-8 correspond to the oligonucleotide HRT alone (HRT, 34 nt); HRT-PEG4-TCO conjugate; HRT-PEG4-PEG4-TAMRA conjugate; and the HRT-PEG4-TAMRA-CHD conjugate. Bands in lane 7 and lane 8 indicate successful conjugation of TAMRA-methyl-tetrazine probes to the TCO oligo. The gel was then stained with SYBR Gold to visualize all DNA on the gel (SYBR Gold). Lanes 1-4 again correspond to HRT alone (HRT, 34 nt); HRT-PEG4-TCO conjugate; HRT-PEG4-PEG4-TAMRA conjugate; and the HRT-PEG4-TAMRA-CHD conjugate. The bands in lanes 3-4 demonstrate that the TAMRA conjugates in lanes 7-8 contain the oligonucleotide.

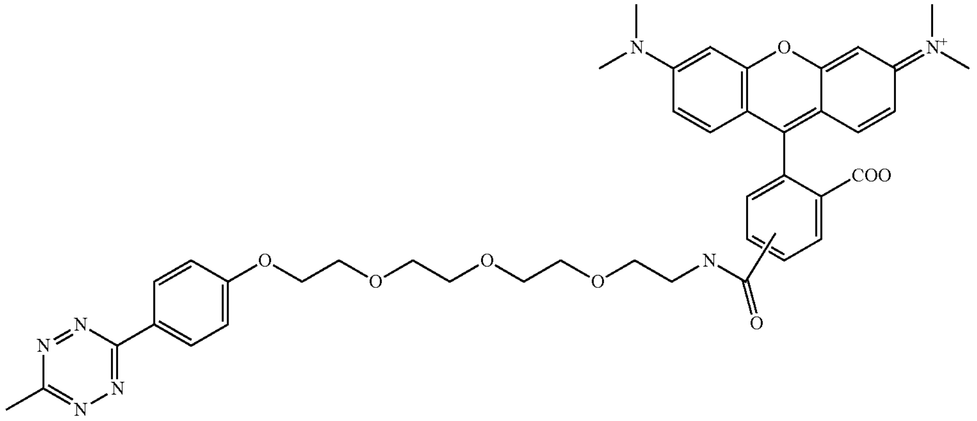

TAMRA-PEG4-methyltetrazine

Additional conjugation reagents of the invention can be made by the synthesis schemes below.

Scheme 4. Synthesis of a Hydrophobic CHD-Azide-Biotin Conjugation Reagent.

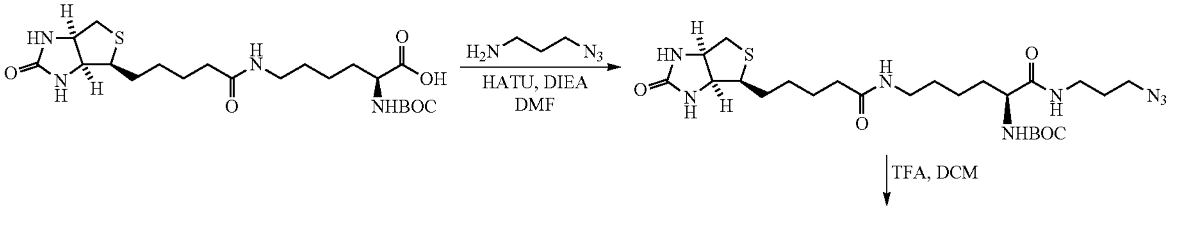

-continued
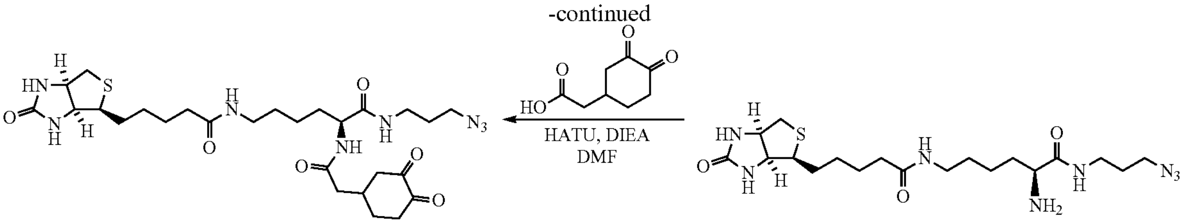
Scheme 5. Synthesis of a Hydrophilic CHD-Azide-Biotin Conjugation Reagent.

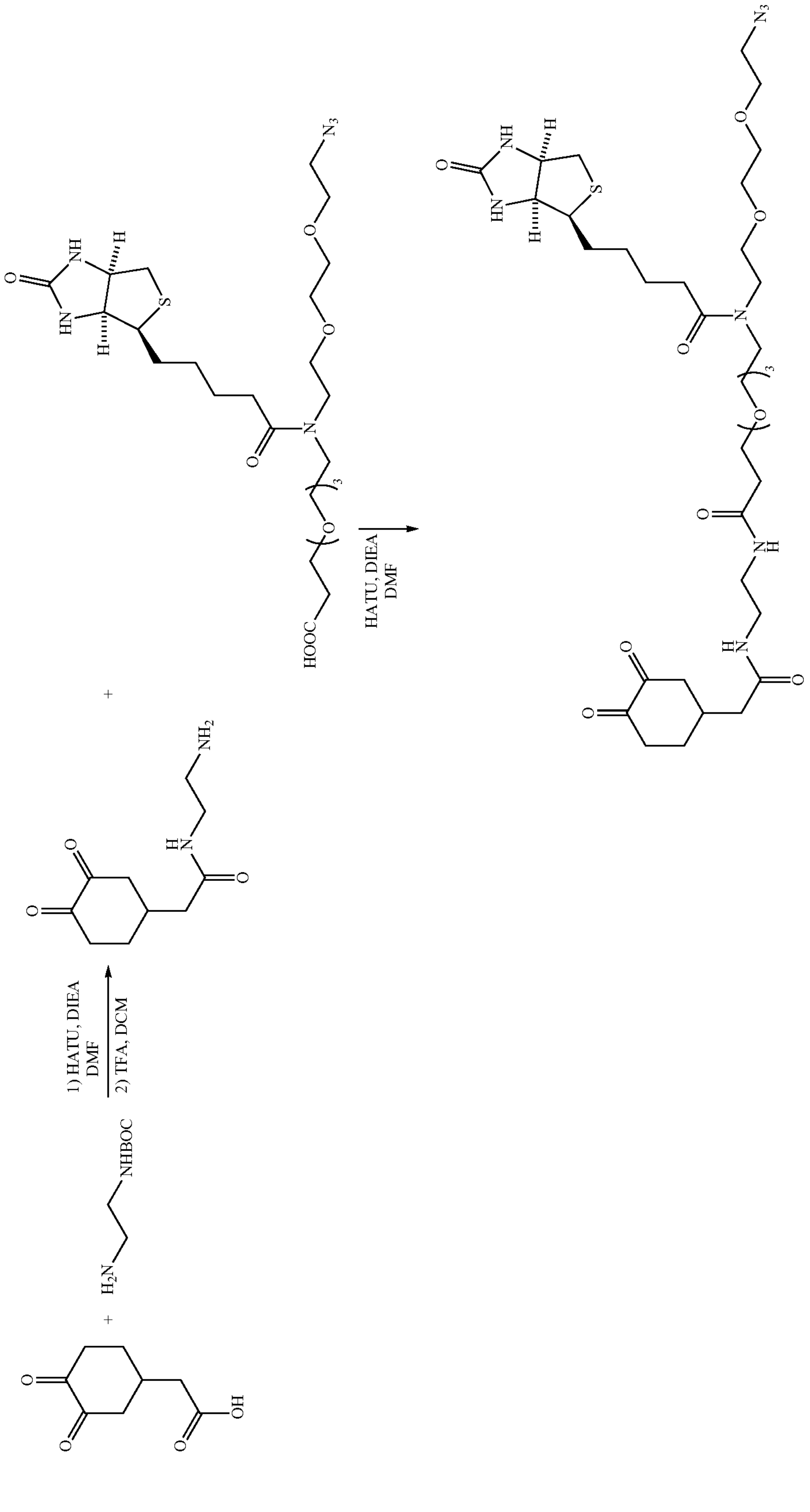
1) HATU, DIEA
DMF
2) TFA, DCM
HATU, DIEA
DMF

Scheme 6. Synthesis of a CHD Conjugation Reagent Cleavable by Enzyme (Cathepsin B).
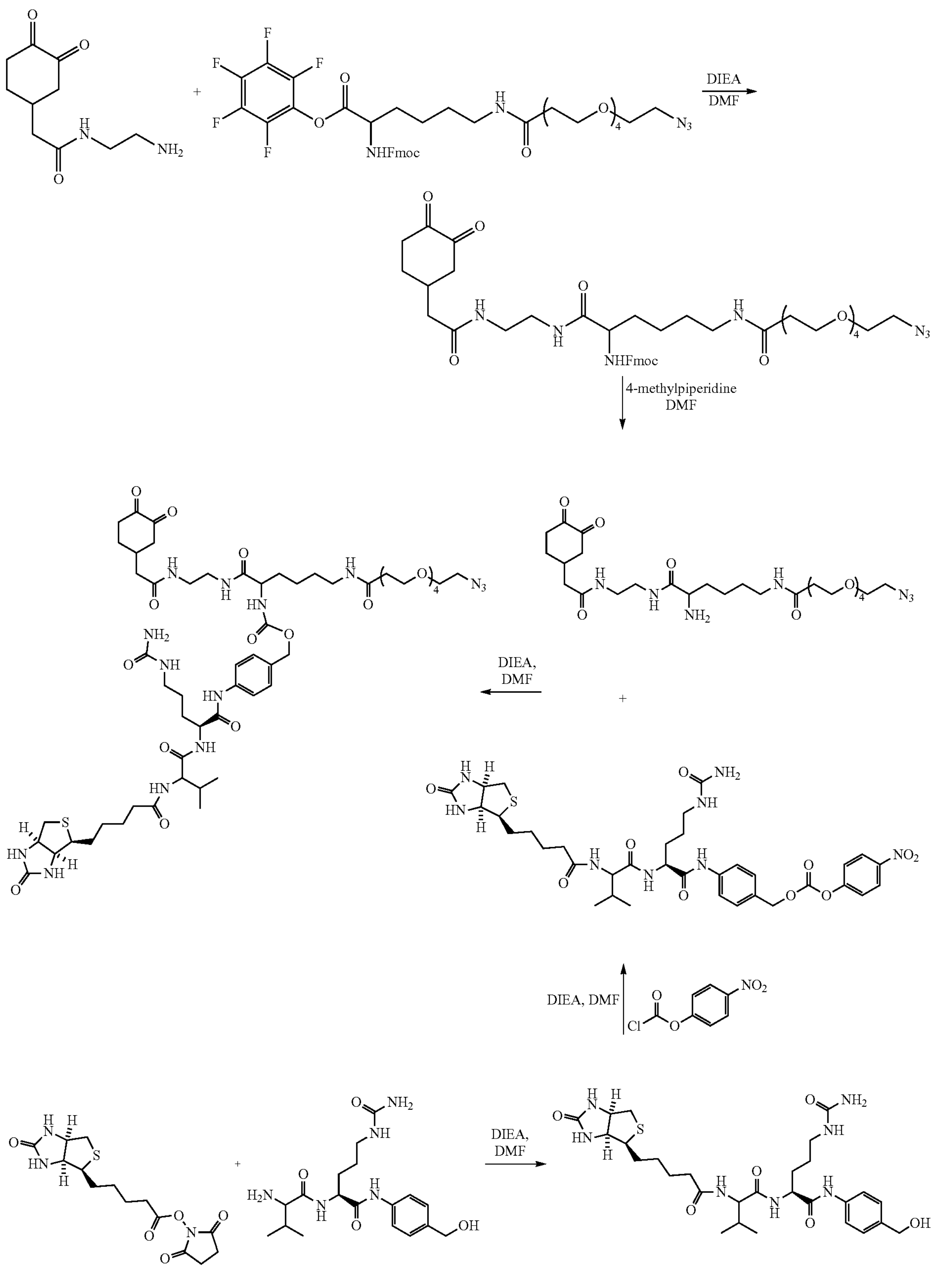

Scheme 7. Synthesis of a CHD Conjugation Reagent Cleavable by UV Light.
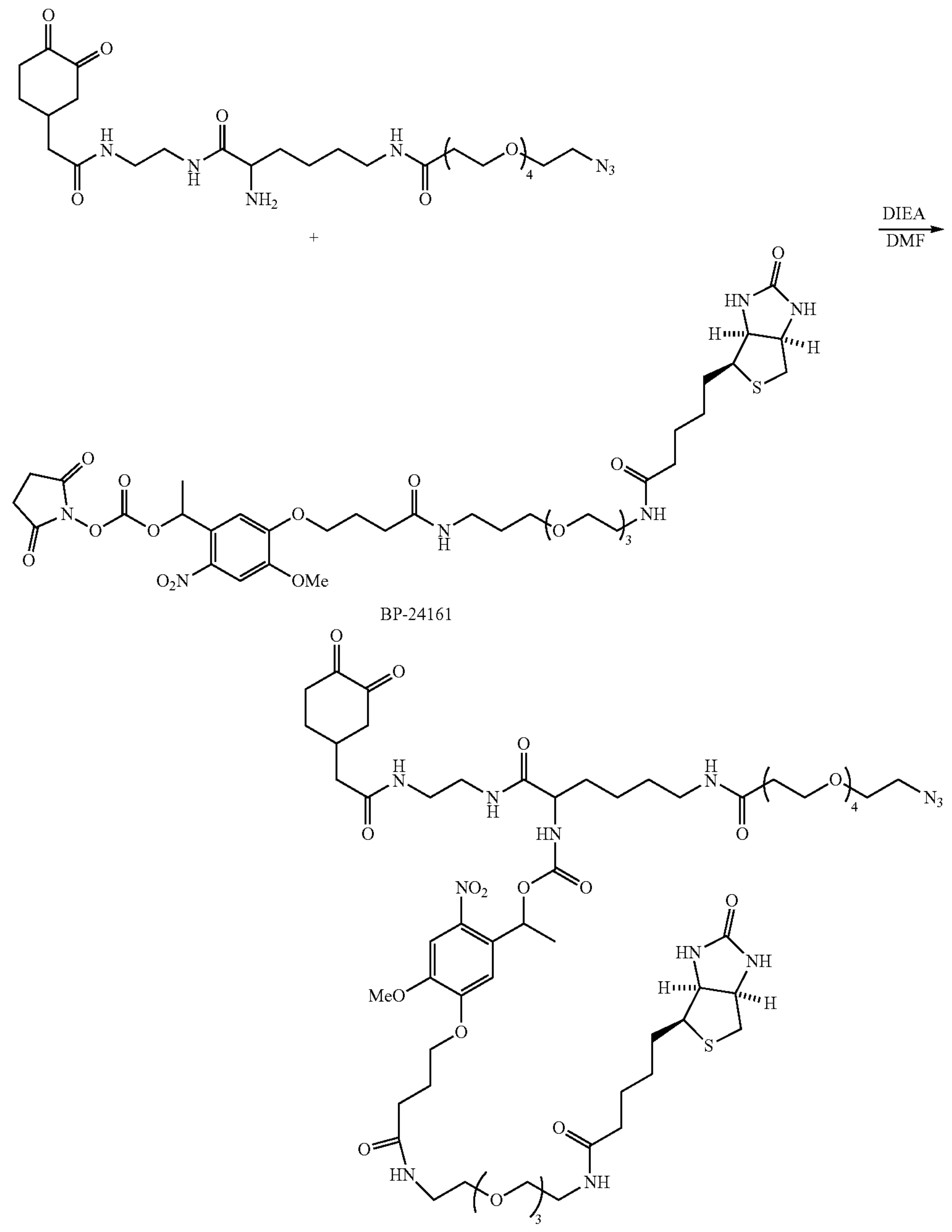
Scheme 8. Synthesis of a CHD Conjugation Reagent Cleavable by Visible Light.

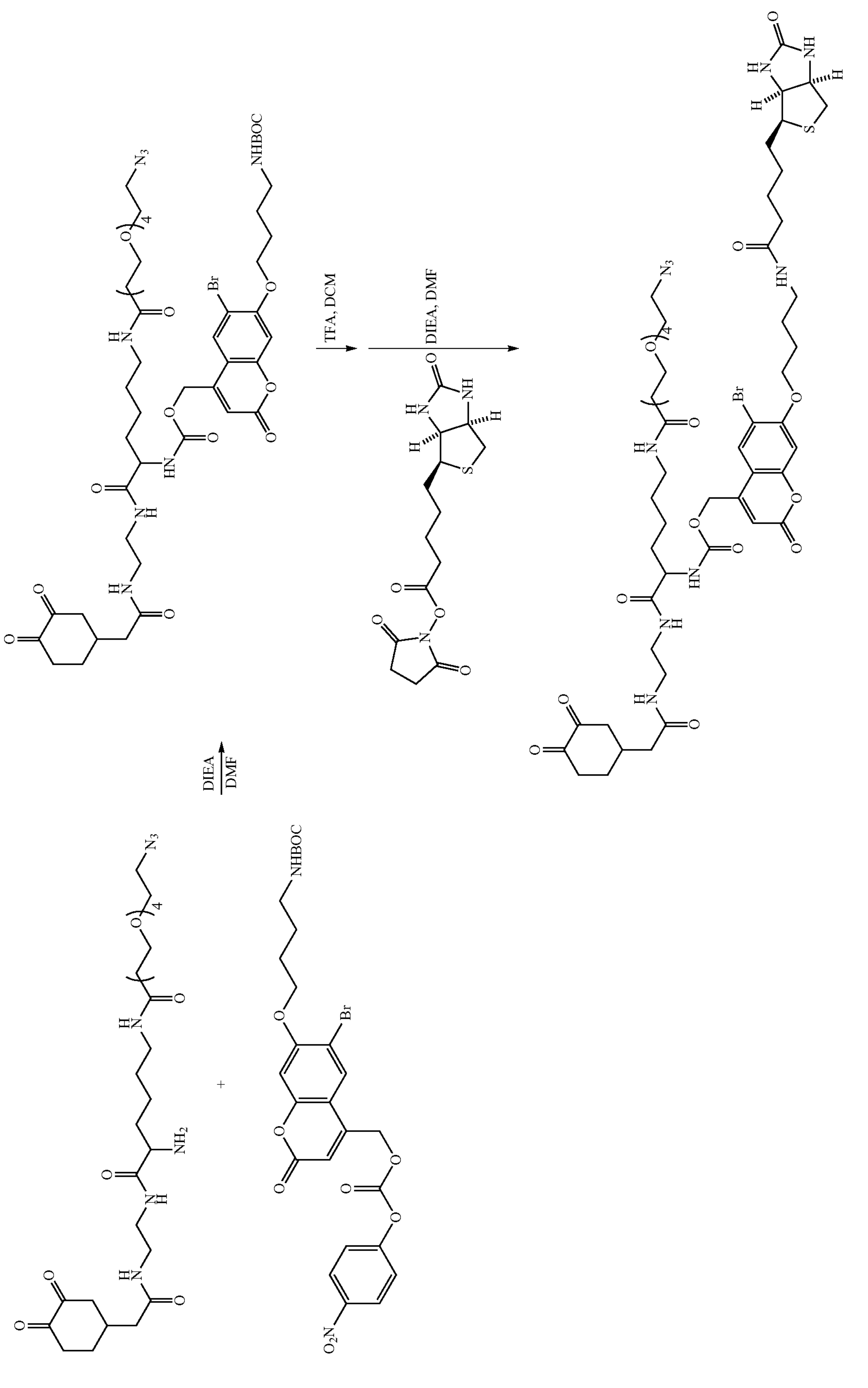
DIEA
DMF
TFA, DCM
DIEA, DMF

Example 9. Suitable Cleavable Linkers Used for Generation of Immobilized Polypeptide-DNA Conjugates During the N-Terminal Workflow (1) An exemplary photocleavable linker (nitrophenyl ester) with an activated ester (NHS-carbonate) and a PEG-linked mTET enrichment tag has been tested for immobilization of polypeptides through their N-termini:

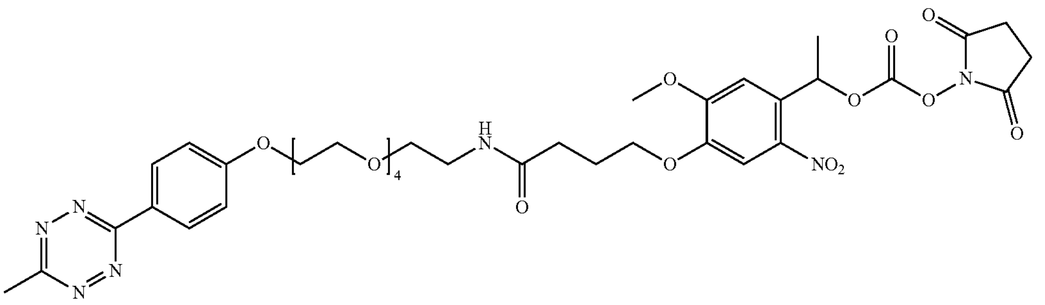

Figure 8:
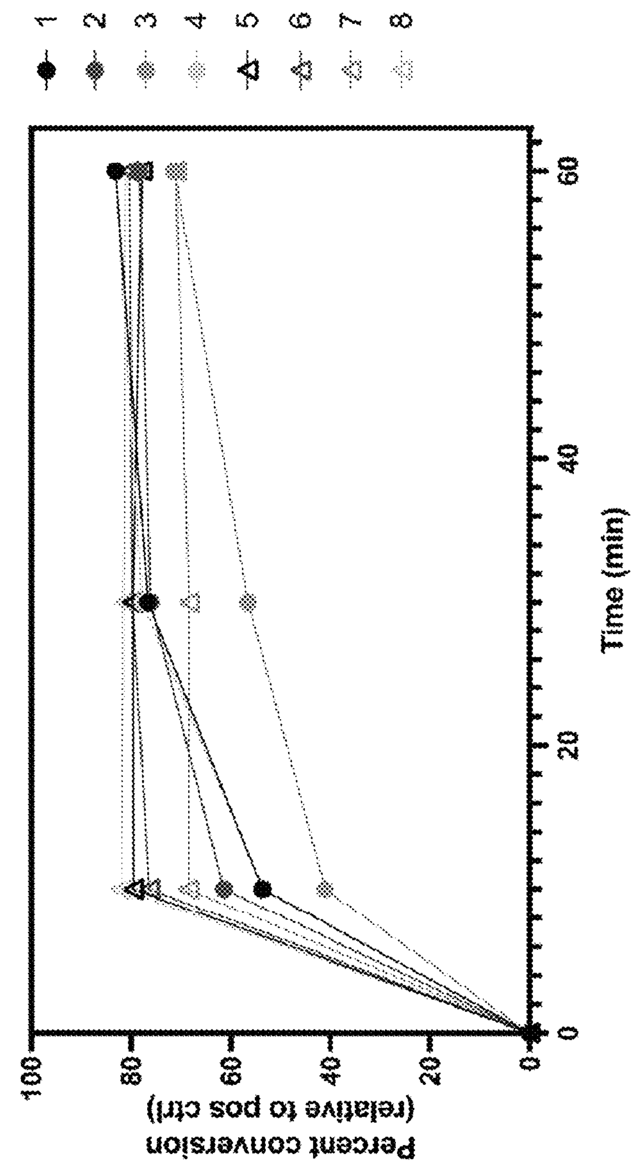
FIG. 8 shows N-terminal functionalization of a polypeptide with the photocleavable linker comprising an activated ester. Reaction conditions were evaluated to optimize functionalization efficiency.

Reaction conditions between N-termini of polypeptides and the linker were evaluated to optimize functionalization efficiency, and exemplary results are shown in FIG. 8. Reaction conditions presented in FIG. 8 were as follows: 1) 10×Phosphate buffered saline (PBS)/dimethylsulfoxide (DMSO)/acetonitrile (CAN) at 37° C.; 2) 10×PBS/DMSO at 37° C.; 3) 100 mM 3-(N-morpholino)propanesulfonic acid (MOPS)/ACN at 37° C. C; 4) 10×PBS/DMSO/ACN/0.1% Tween-20 at 37° C.; 5) 10×PBS/DMSO/ACN at 60° C.; 6) 10×PBS/DMSO at 60° C.; 7) 100 mM MOPS/ACN at 60° C.; 8) 10×PBS/DMSO/ACN/0.1% Tween-20 at 60° C. As used herein, "10×PBS" indicates a concentration ten-fold higher than standard PBS (137 mM sodium chloride, 2.7 mM KCl, 10 mM $Na_2HPO_4$, 1.8 mM $KH_2PO_4$). Based on the data presented in FIG. 8, N-terminal functionalization is complete (at 80% maximal conversion) after 20 min using 10×PBS in DMSO at 60° C.

Figure 9:
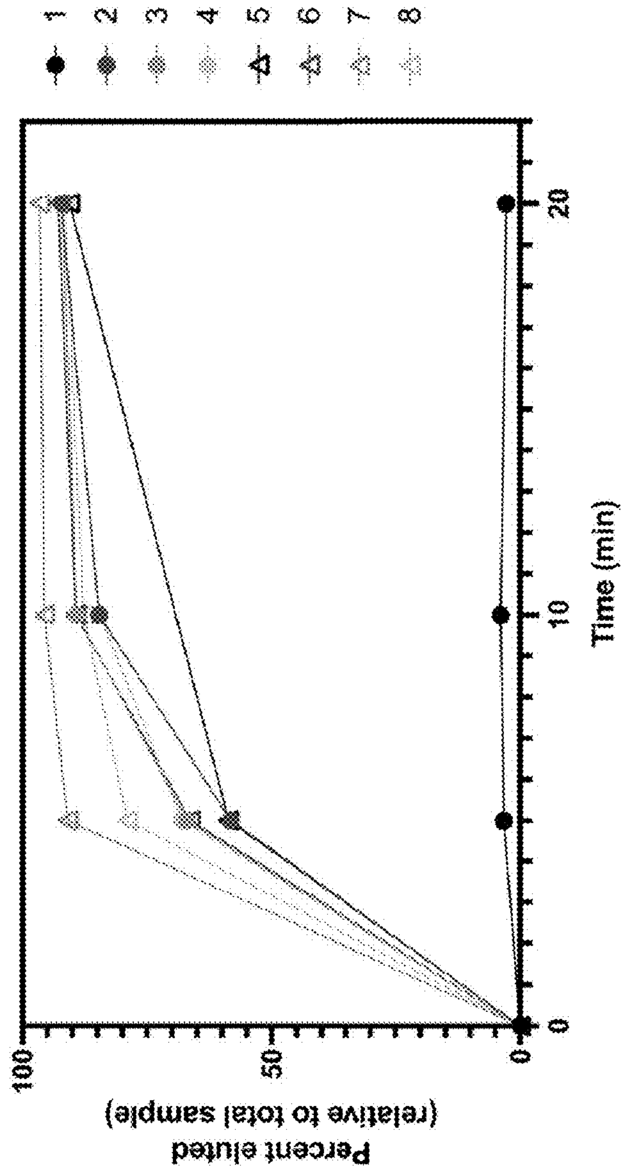
FIG. 9. Cleavage efficiency using the photocleavable linker comprising an activated ester and an enrichment tag. Reaction conditions were evaluated to optimize cleavage efficiency.
Figure 10:
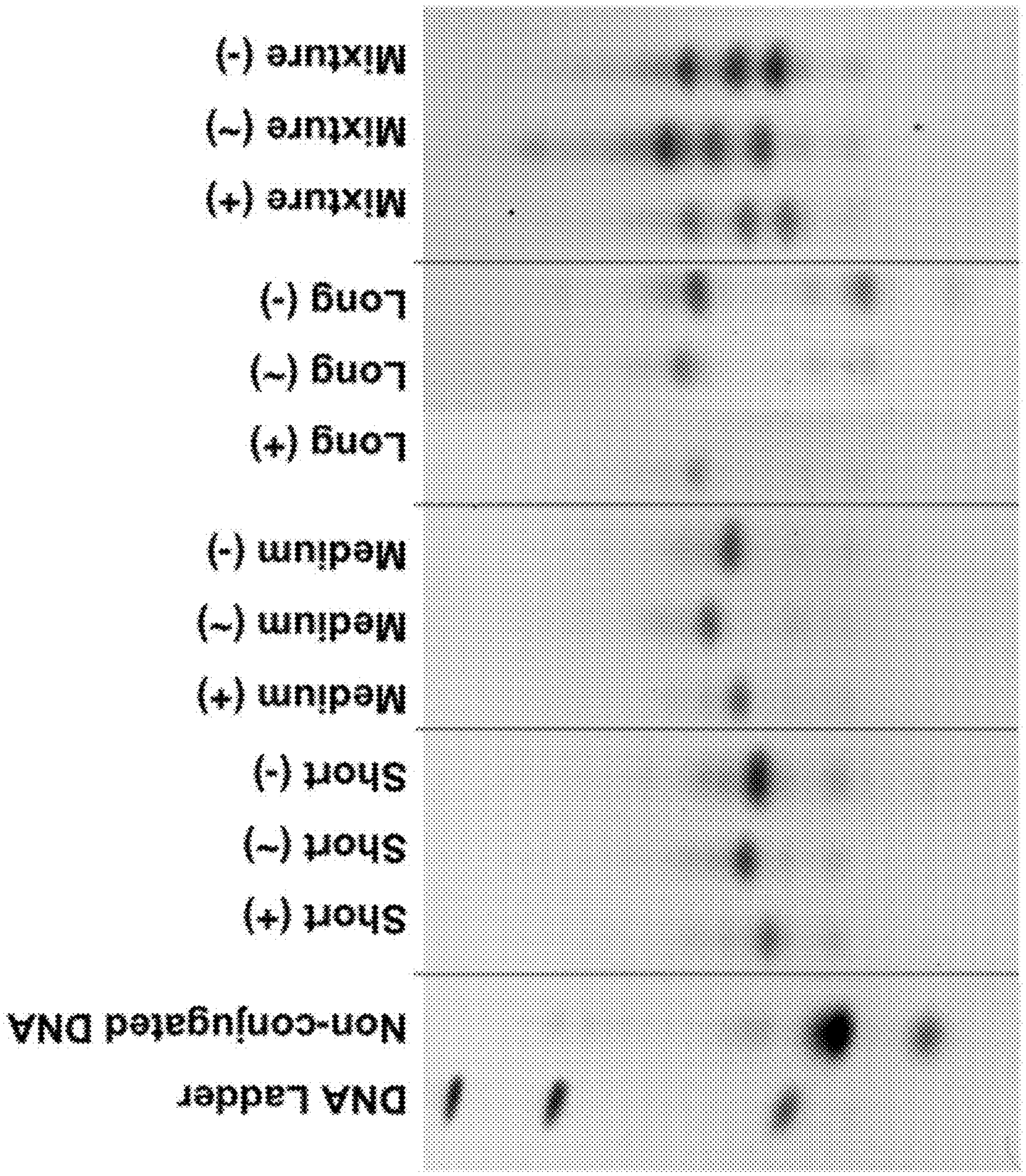
FIG. 10. Evaluation of a conjugate formation bias during the exemplary N-terminal workflow with the photocleavable linker. Azide terminated peptides were immobilized on a solid support using photocleavable linkers through N-termini and conjugated with DBCO-DNA. After formation, polypeptide-DNA conjugates were cleaved from the solid support and analyzed by gel electrophoresis to assess relative formation of conjugates. Peptides were designed to have varied lengths (short:=7, medium=12, and long=20 amino acids) and charge states (positive (+), neutral (~), and negative (−)].

Further, light-induced cleavage conditions for the photocleavable linker during the release step of the N-terminal workflow were evaluated to optimize cleavage efficiency, and the results are shown in FIG. 9. Reaction conditions presented in FIG. 9 were as follows: 1) Dark; 2) 1×PBS; 3) 10×PBS; 4) 100 mM Tris, pH 7.5; 3) 100 mM Borate, pH 8.54; 6) 100 mM MES, pH 6.5; 7) PBS/ACN; 8) PBS/formamide. Based on the data presented in FIG. 9, nearly complete peptide recovery is achieved after 10 min (with photocleavage-inducing illumination at 365 nm for 15 min, 100 mW per sample) using a PBS/acetonitrile buffer solution Further, a bias for conjugate formation during the N-terminal workflow with the photocleavable linker was evaluated. Azide terminated peptides were immobilized on a solid support using the photocleavable linker through N-termini and conjugated with DBCO-DNA tags. After formation, polypeptide-DNA conjugates were cleaved from the solid support and analyzed by gel electrophoresis to assess relative formation of conjugates. Peptides of different lengths [short (S), medium (M), and long (L)] and charge [positive (+), neutral (~), and negative (−)] demonstrated little difference in conjugate formation efficiency (FIG. 10).

(2) An exemplary amino acid-based "trifunctional" linker (FMOC-protected activated ester of lysine with a click chemistry compatible side chain) has been tested for immobilization of polypeptides through their N-termini:

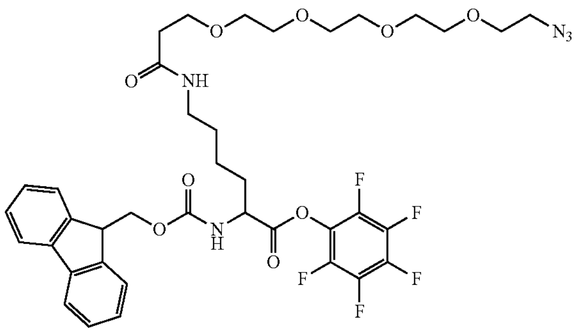 [SMILES: [N-]=[N+]=NCCOCCOCCOCCOCCC(=O)NCCCCC(NC(=O)OCC1c2ccccc2-c2ccccc21)C(=O)Oc1c(F)c(F)c(F)c(F)c1F]

Figure 11:
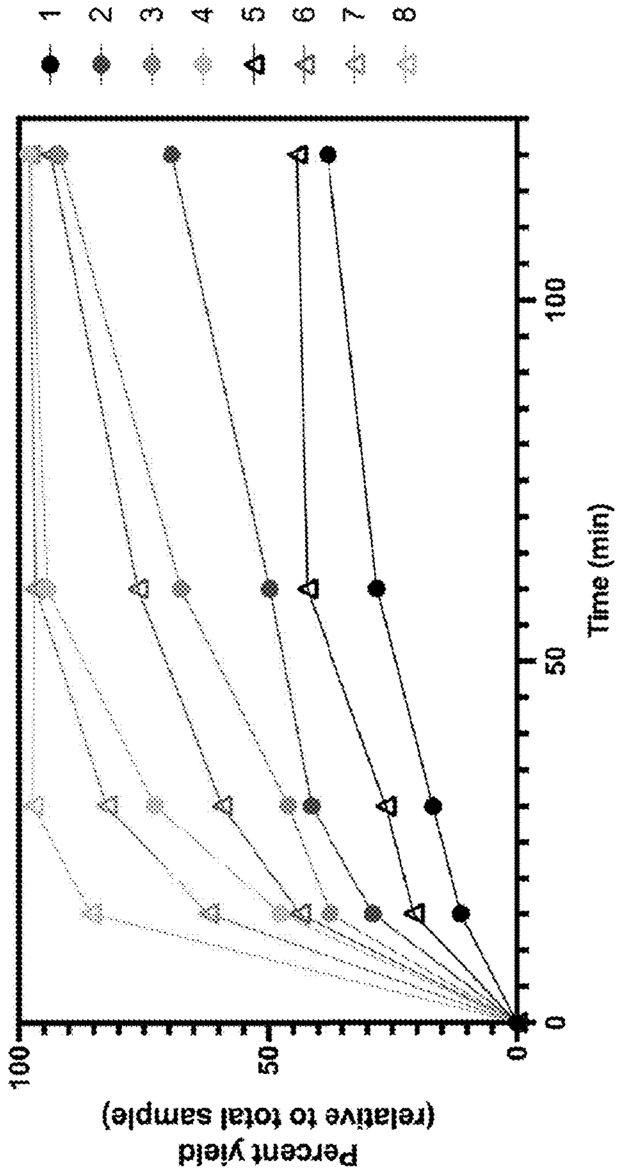
FIG. 11 shows N-terminal functionalization of a polypeptide with the amino acid-based linker comprising a trifunctional lysine derivative. Reaction conditions were evaluated to optimize functionalization efficiency.

Reaction conditions between N-termini of polypeptides and the linker were evaluated to optimize functionalization efficiency, and the results are shown in FIG. 11. Concentration and temperature were adjusted to optimize N-terminal functionalization. Reaction conditions presented in FIG. 11 were as follows: 1) 1 mM ARR1 at 37° C.; 2) 5 mM ARR1 at 37° C.; 3) 10 mM ARR1 at 37° C.; 4) 20 mM ARR1 at 37° C.; 5) 1 mM ARR1 at 60° C.; 6) 5 mM ARR1 at 60° C.; 7) 10 mM ARR1 at 60° C.; 8) 20 mM ARR1 at 60° C. Nearly quantitative yield was obtained under appropriate conditions. Based on the data presented in FIG. 11, nearly complete N-terminal modification was achieved after 60 min with 20 mM ARR1 in using a 100 micromolar MOPS/DMF buffer solution, pH 7.4.

(3) Exemplary peptoid linkers with an activated ester (PFP) and generic enrichment tag (TAG) can be used for immobilization of polypeptides through their N-termini:

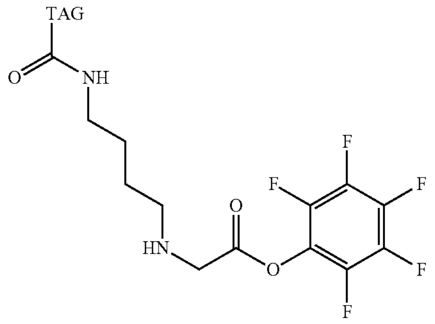

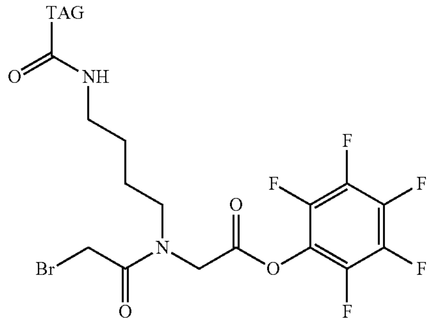

Both naive peptoids and bromoacetylated peptoids are illustrated; either of which may serve as the traceless, cleavable linker.

Figure 12:
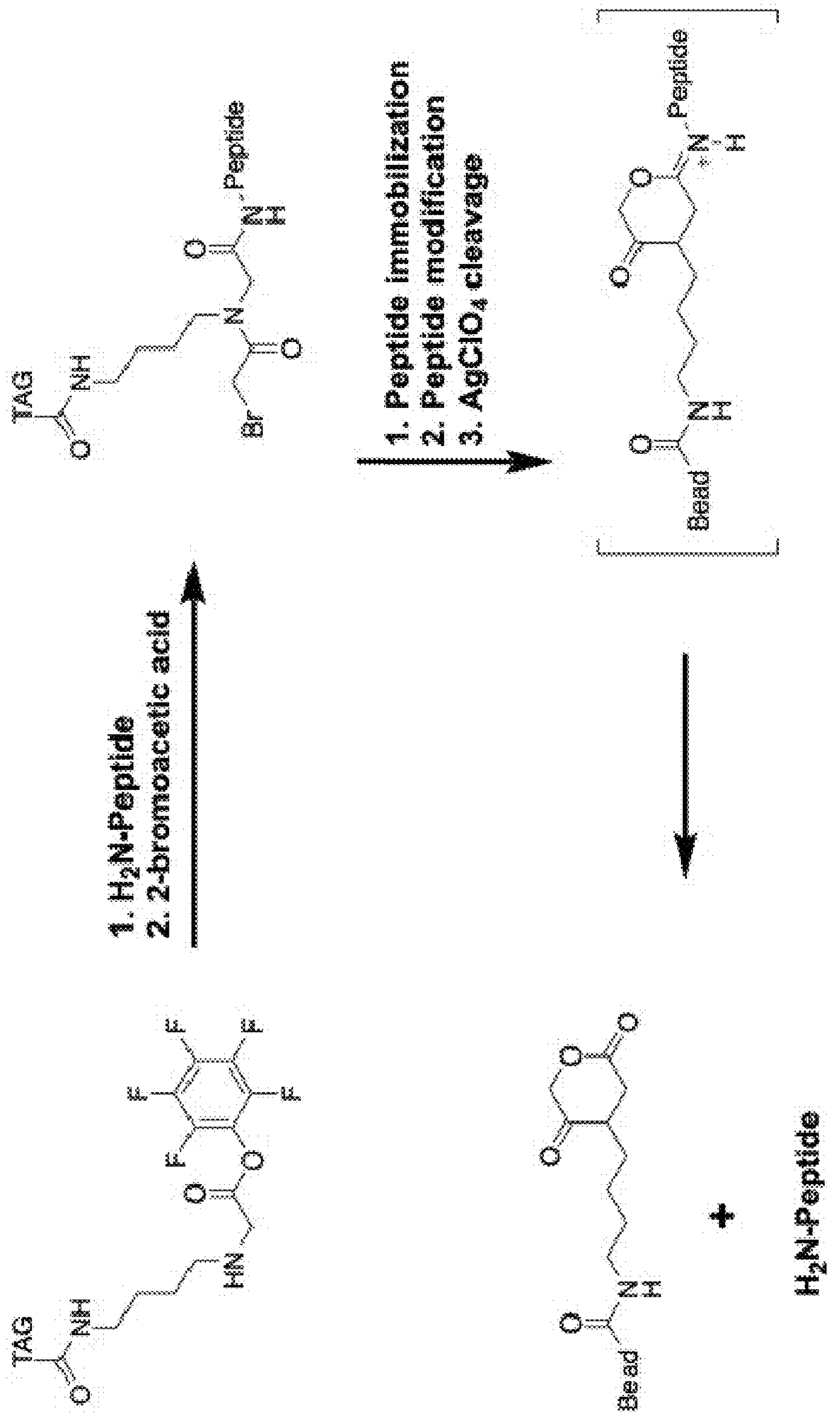
FIG. 12 shows generic or exemplary workflow and mechanism for peptoid-mediated N-terminal elimination with silver salts (adopted from Proulx C, et al., On-resin N-terminal peptoid degradation: Toward mild sequencing conditions. Biopolymers. 2016 September; 106(5):726-36).

Generic and exemplary workflow and mechanism for peptoid-mediated N-terminal elimination with silver salts is shown in FIG. 12 (adopted from Proulx C. et al., On-resin N-terminal peptoid degradation: Toward mild sequencing conditions. Biopolymers. 2016 September; 106(5):726-36). In FIG. 12, polypeptide immobilization is illustrated through a generic bead/tag interaction. While previously demonstrated with peptoid polymers, the N-terminal elimination proceeds with an amino acid in the second position and provides an opportunity to exploit this chemistry for N-terminal workflows. The peptoid linker is a covalent and chemically stable (e.g., pH stable) thereby enabling a variety of peptide modification chemistries on immobilized peptides.

Figure 13:
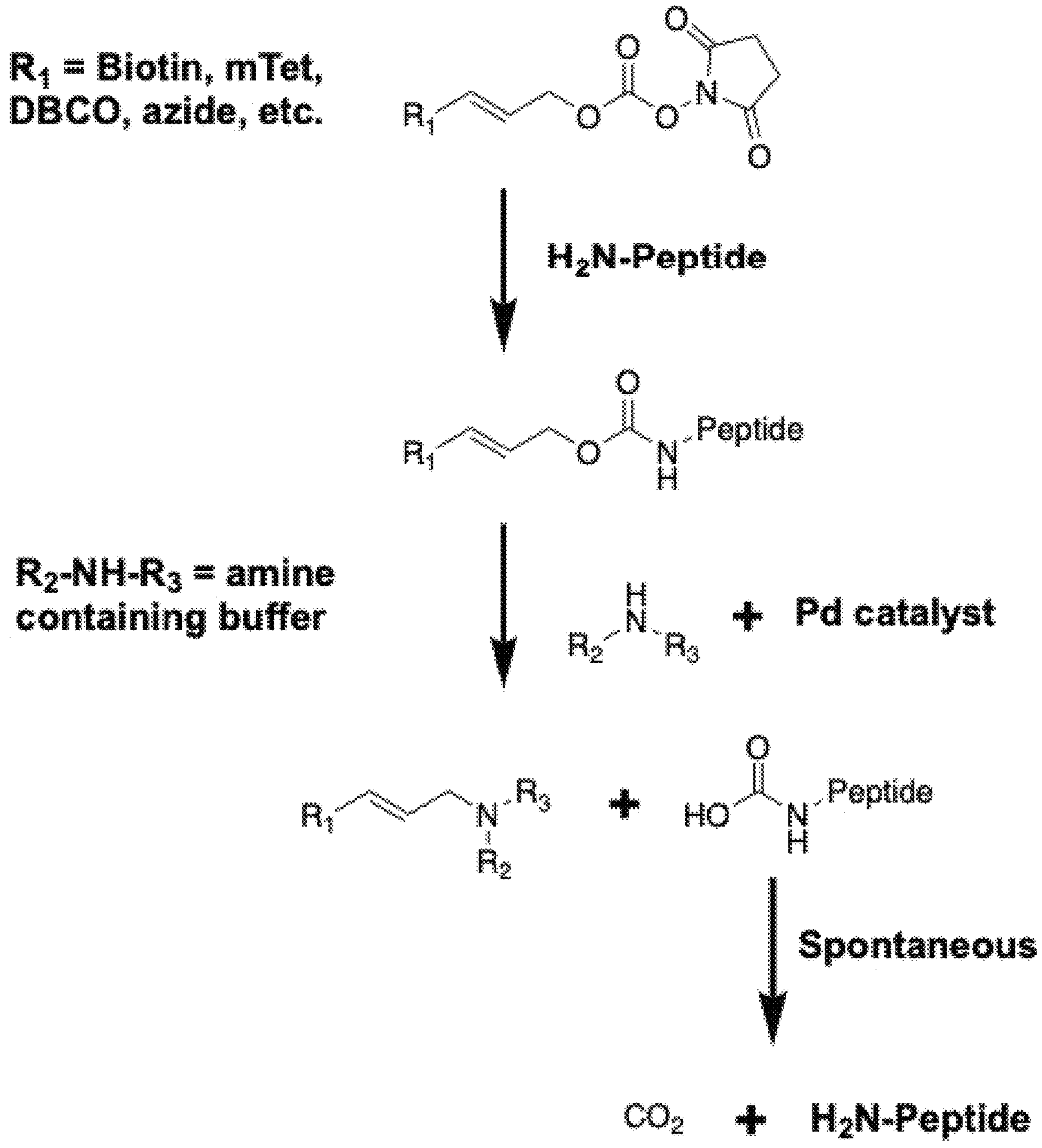
FIG. 13. Exemplary workflow illustrating N-terminal modification and the mechanism for traceless cleavage with an Alloc palladium (Pd)-cleavable linker.

(4) An exemplary Palladium-cleavable Alloc linker with an activated ester and an exemplary functionalization scheme (N-terminal modification and traceless cleavage) is shown in FIG. 13. A variety of enrichment tags are accessible through relatively simple chemical modification to the distal end of the molecule (R1). Additional steps related to protein processing and peptide modification are omitted in the workflow to specifically highlight the chemical mechanism for this covalent, traceless linker.

Figure 14:
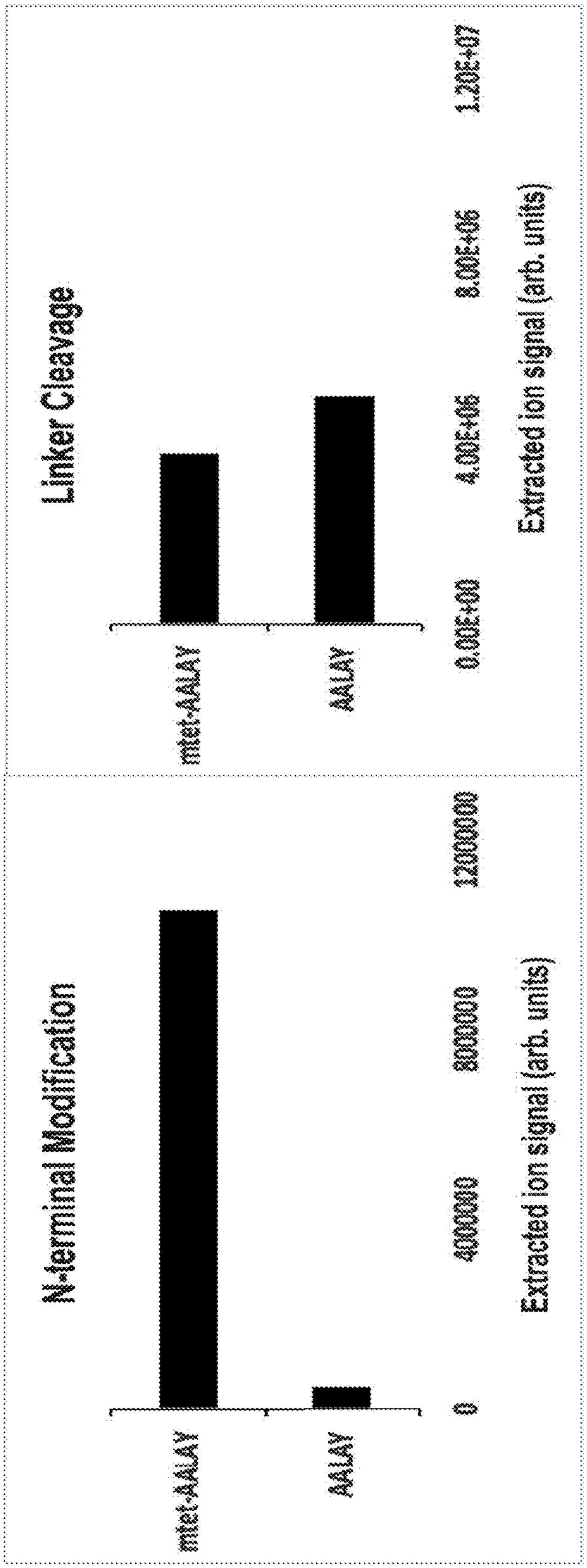
FIG. 14 shows results of N-terminal modification and Pd-catalyzed, traceless cleavage of an exemplary peptide (AALAY, SEQ ID NO: 12) according to the workflow shown in FIG. 13.

N-terminal functionalization of polypeptides with the linker, as well as efficiency of the Pd-catalyzed, traceless cleavage of the linker were evaluated (FIG. 14) on an exemplary peptide (AALAY, SEQ ID NO: 12). Integrated LC-MS extracted ion currents are illustrated in FIG. 14, Efficient N-terminal modification with a Pd-cleavable linker containing an mTET enrichment tag is indicated by the signal magnitude of the modified product relative to the starting material. Reasonable cleavage efficiency is further indicated by the relative recovery of starting material after treatment with a Pd catalyst. In this embodiment, Pd catalysts such as palladium acetate (Pd(OAc)2) or Bis(triphenylphosphine)palladium(II) dichloride, may be employed at 0.1-5 mM in aqueous buffers at 25-37° C. in the presence of amine containing buffers (e.g., Hepes, MOPS, Tris) to achieve efficient cleavage of the alloc linker.

(5) An exemplary self-immolative linker comprising para-nitrophenyl carbonate reactive ester coupled to a para-nitrobenzylcarbonate and an PEG-mTET enrichment tag:

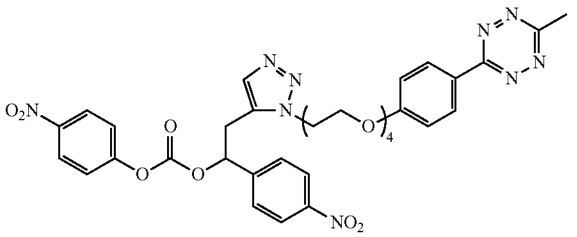

Figure 15:
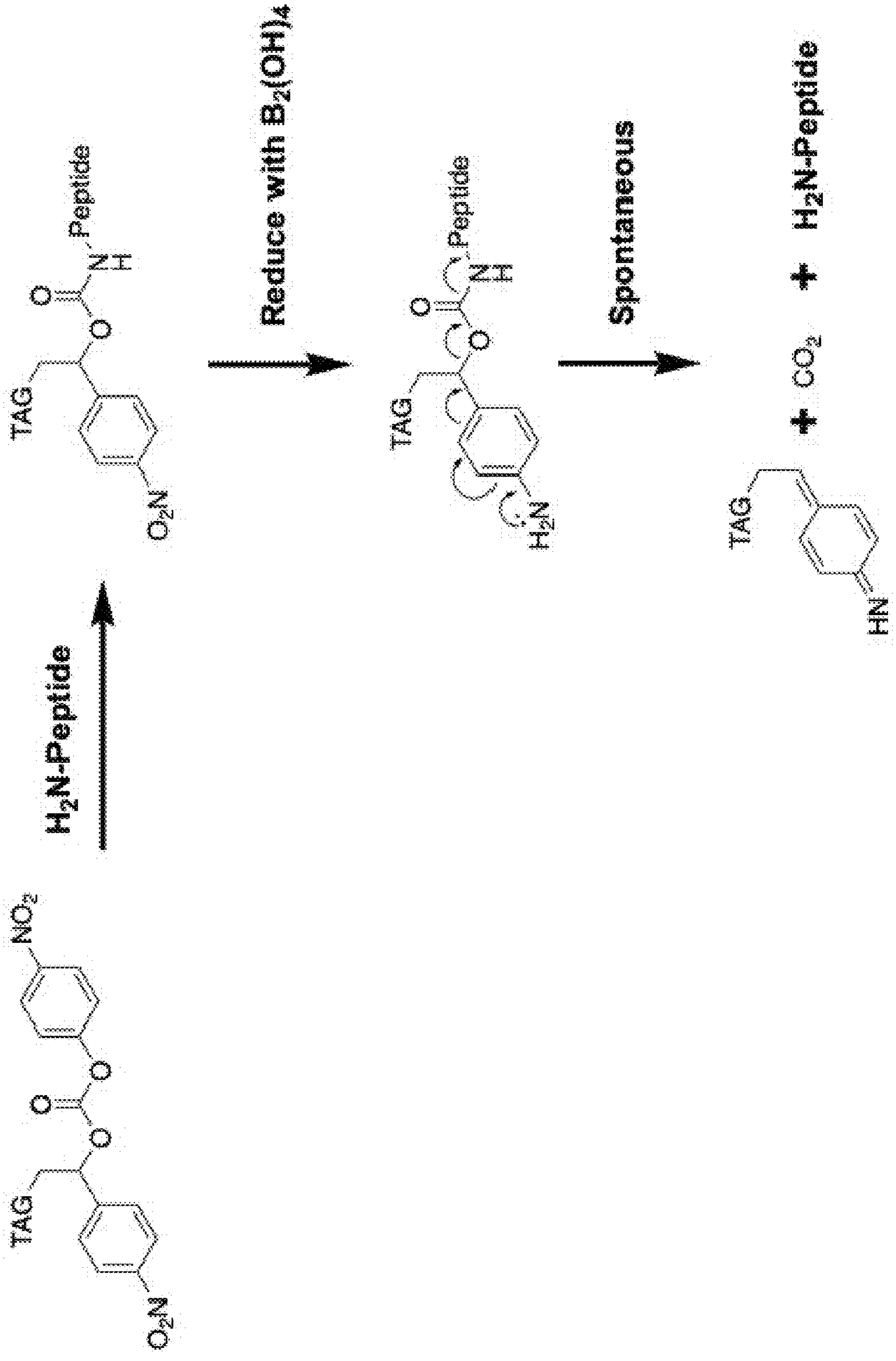
FIG. 15. shows an exemplary partial workflow illustrating N-terminal modification and the mechanism for traceless cleavage with the self-immolative para-nitrobenzyl linker.

FIG. 15 shows an exemplary partial workflow illustrating N-terminal modification and the mechanism for traceless cleavage with the self-immolative para-nitrobenzyl linker. Additional steps related to protein processing, peptide immobilization, and peptide modification are omitted to specifically highlight the chemical mechanism for this covalent, traceless linker.

Example 10. Polypeptide Sample Preparation N-Terminal Workflow for the ProteoCode™ Assay This example demonstrates an exemplary sample preparation N-terminal workflow used for preparing peptides using the CHD-orthogonal handles described above. The exemplary workflow depicted in FIG. 7 outlines preparation of CHD-labeled and DNA-coupled polypeptides starting from an unpurified proteomic sample.

Protein denaturation and digestion. For a 10 μg of protein sample, samples were diluted to the desired protein input concentration in an appropriate buffer (10 ug/45 μL; 100 mM carbonate/bicarbonate buffer at pH 9.15 with 0.1% sodium dodecyl sulfate (SDS)). Cysteines were reduced with TCEP added to a final concentration of 5 mM. Samples were incubated for 15 min at 37° C., and, after cooling, iodoacetamide (IAA) stock was added to a final concentration of 20 mM. Samples were incubated at 37° C. for 15 min to allow the alkylation to proceed. Lysine side chains were blocked by addition of NHS-acetate (ARR1, 10 mM) at 60° C. for 30 min. Trypsin was added at a 1:25 ratio, by mass, for each sample and incubated for 2 hours at 37° C. to digest the sample. Resulting peptides were then functionalized at the amine terminus using 10 mM photo-cleavable linker (AAR2, a self-immolative linker comprising para-nitrophenyl carbonate reactive ester coupled to a para-nitrobenzylcarbonate and an PEG-mTET enrichment tag shown in Example 1, section (5)) at 37° C. for 60 min, Peptide immobilization to solid support. Peptides were immobilized to a solid support (TCO agarose, Click Chemistry Tools) through the enrichment tag (mTET moiety). The peptide mixture was incubated with 130 μL TCO beads for 60 min at 37° C. to immobilize the modified peptides. Other combinations of enrichment tag and compatible solid support can be implemented. Excess material (i.e. cellular components), unreacted peptides, and reaction components were removed by washing three times with PBS-T (PBS (phosphate-buffered saline) plus 0.1% TWEEN® 20).

CHD functionalisation of C-terminal arginines and polypeptide-DNA conjugate formation. Each sample was resuspended after concentration in vacuo in 20 μL 0.2 M NaOH (pH 13.7), 1 M KPhos (pH 8.3), or 2 M KPhos (pH 8.3). CHD Stock (CHD-$PEG_3$-azide in DMSO) was added for a final concentration of 10 mM and incubated at 37° C. for 1 hr, 80° C. for 1.5 hours, or 80° C. for 1 hour, respectively. The reaction was neutralized by adding equal volume 1 M Tris, pH 7.4, and washed to remove excess/unreacted CHD-$PEG_3$-azide and impurities. Samples were diluted to 10 μg/1000 μL in PBS-T. On-bead DNA-polypeptide conjugate (polypeptide-conjugation reagent-nucleic acid conjugate) formation was carried out using a solution of DBCO-DNA (Dibenzocyclooctyne-coupled DNA; DNA=5'-/5Phos/CAA GTT CTC AGT AAT GCG TAG/DBCOdT/CC GCG ACA CTA G-3'; SEQ ID NO: 3) and incubating for 16 hours. The beads containing the conjugated product were washed to remove excess DBCO-DNA.

Sample Barcoding. Upon completion of incubation, beads were centrifuged and washed to remove any excess DBCO-DNA. Sample barcodes were added and beads were washed twice with 200 μL PBS-T. The peptide-DNA conjugate was eluted with 10 μL 4 mM biotin, 20 mM Tris-HCl, and 50 mM NaCl. Conjugate formation and barcoding were confirmed by loading 0.5 μL of sample (5 pmol) on TBU gel electrophoresis. (15% TBU gel, 200V, 50 min). The peptides were then immobilized on a support. The DNA of the peptide-DNA conjugate was hybridized and ligated to a DNA recording tag containing a complementary sequence attached to beads at appropriate spacing and density (see e.g., US20200348308 A1).

Release of peptide-DNA conjugates. Peptides were removed according to the required reaction conditions for cleaving the intended cleavable linker. For example, photocleavable linkers were cleaved through illumination at 365 nm for 15 min with approximately 100 mW/sample. Released peptide-DNA conjugates were separated from the solid support by simple pipetting (especially for magnetic solid supports), a porous filter or other, similar means.

Using the methods in these examples and general knowledge in the field, a wide array of conjugation reagents of the invention can be made with various reactive handles, detectable labels, binding agents, and cleavage options can be constructed.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications., patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The invention claimed is:

1. A composition comprising a peptide-polynucleotide conjugate, wherein a covalent linkage connecting a peptide and a polynucleotide of the peptide-polynucleotide conjugate comprises the following substructure (D):

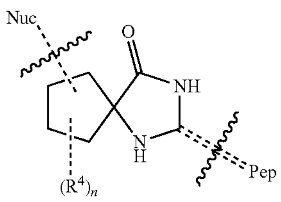

(D)

or a tautomer thereof, wherein:

the dashed bond to Nuc represents where substructure (D) is covalently linked to the polynucleotide;

the dashed bond to Pep represents where substructure (D) is covalently linked to the peptide;

$R^4$ is an optional substituent on the cyclopentyl ring, and each $R^4$ is independently selected from the group consisting of $C_{1-2}$ alkyl, $C_{1-2}$ alkoxy, $C_{1-2}$ haloalkyl, —COOR, $SO_3R$, halo, hydroxy, and $C(O)NR_2$;

each R is independently H or $C_{1-4}$ alkyl optionally substituted with up to three groups selected from the group consisting of halo, OH, $C_{1-2}$ alkyl, $C_{1-2}$ haloalkyl, $C_{1-2}$ alkoxy, and carbonyl (oxo), or two R groups on one N are forming a 4-8 membered ring optionally containing an additional one or two heteroatoms selected from N, O and S as ring members and optionally substituted with one or two groups selected from halo, $C_{1-2}$ alkyl, $C_{1-2}$ haloalkyl, $C_{1-2}$ alkoxy, hydroxy, and carbonyl (oxo); and n is 0, 1, 2 or 3.

2. The composition of claim 1, further comprising a solid support, wherein the peptide is attached to the solid support via a linker.

3. The composition of claim 1, wherein the covalent linkage is attached to an arginine residue of the peptide.

4. The composition of claim 2, wherein the peptide is covalently attached to the solid support and the linker is a cleavable linker.

5. The composition of claim 1, wherein the covalent linkage connecting the peptide and the polynucleotide comprises substructure (D'):

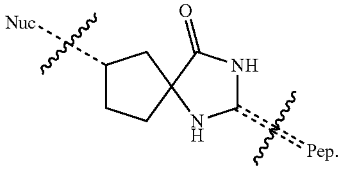

(D')

6. The composition of claim 2, wherein an N-terminal amino acid (NTAA) of the peptide forms a covalent bond with the linker.

7. The composition of claim 6, wherein the covalent bond between the NTAA and the linker is an amide bond.

8. The composition of claim 1, wherein the polynucleotide comprises a barcode.

9. The composition of claim 5, wherein the covalent linkage is attached to an arginine residue of the peptide.

* * * * *

SEQUENCE LISTING

```
Sequence total quantity: 13
SEQ ID NO: 1            moltype = AA  length = 5
FEATURE                 Location/Qualifiers
REGION                  1..5
                        note = synthetic reactive peptide
SITE                    1
                        note = MISC_FEATURE - N-terminus acetyl
source                  1..5
                        mol_type = protein
                        organism = synthetic construct
SEQUENCE: 1
AFAVR                                                            5

SEQ ID NO: 2            moltype = AA  length = 5
FEATURE                 Location/Qualifiers
REGION                  1..5
                        note = An internal control peptide
SITE                    1
                        note = MISC_FEATURE - N-terminus acetyl
source                  1..5
                        mol_type = protein
                        organism = synthetic construct
SEQUENCE: 2
AFAVA                                                            5

SEQ ID NO: 3            moltype = DNA  length = 34
FEATURE                 Location/Qualifiers
misc_feature            1..34
                        note = DNA-peptide chimera
misc_feature            1
                        note = 5' - phosphorylated
misc_feature            22
                        note = dibenzocyclooctyne-coupled thymine
source                  1..34
                        mol_type = other DNA
                        organism = synthetic construct
```

-continued

```
SEQUENCE: 3
caagttctca gtaatgcgta gtccgcgaca ctag                         34

SEQ ID NO: 4           moltype = AA  length = 7
FEATURE                Location/Qualifiers
REGION                 1..7
                       note = peptide with serine phosphorylaton
SITE                   1
                       note = MISC_FEATURE - N-terminus acetyl
SITE                   5
                       note = MISC_FEATURE - phosphorylation
source                 1..7
                       mol_type = protein
                       organism = synthetic construct
SEQUENCE: 4
ADWASGQ                                                       7

SEQ ID NO: 5           moltype = AA  length = 7
FEATURE                Location/Qualifiers
REGION                 1..7
                       note = peptide with threonine phosphorylation
SITE                   1
                       note = MISC_FEATURE - N-terminus acetyl
SITE                   5
                       note = MISC_FEATURE - phosphorylation
source                 1..7
                       mol_type = protein
                       organism = synthetic construct
SEQUENCE: 5
ADWATGQ                                                       7

SEQ ID NO: 6           moltype = AA  length = 13
FEATURE                Location/Qualifiers
REGION                 1..13
                       note = synthetic peptide
SITE                   13
                       note = MISC_FEATURE - C-terminal lysine with an azide
                        substitution on the side chain
SITE                   13
                       note = MISC_FEATURE - C-terminal amide
source                 1..13
                       mol_type = protein
                       organism = synthetic construct
SEQUENCE: 6
FSGVARGDVR GGK                                                13

SEQ ID NO: 7           moltype = AA  length = 14
FEATURE                Location/Qualifiers
REGION                 1..14
                       note = Synthetic peptide
SITE                   14
                       note = MISC_FEATURE - C-terminal lysine with an azide
                        substitution on the side chain
SITE                   14
                       note = MISC_FEATURE - C-terminal amide
source                 1..14
                       mol_type = protein
                       organism = synthetic construct
SEQUENCE: 7
AFSGVARGDV RGGK                                               14

SEQ ID NO: 8           moltype = AA  length = 15
FEATURE                Location/Qualifiers
REGION                 1..15
                       note = synthetic peptide
SITE                   15
                       note = MISC_FEATURE - C-terminal lysine with an azide
                        substitution on the side chain
SITE                   15
                       note = MISC_FEATURE - C-terminal amide
source                 1..15
                       mol_type = protein
                       organism = synthetic construct
SEQUENCE: 8
SAFSGVARGD VRGGK                                              15

SEQ ID NO: 9           moltype = AA  length = 18
FEATURE                Location/Qualifiers
REGION                 1..18
```

-continued

```
                       note = Synthetic peptide
SITE                   18
                       note = MISC_FEATURE - C-terminal lysine with an azide
                        substitution on the side chain
SITE                   18
                       note = MISC_FEATURE - C-terminal amide
source                 1..18
                       mol_type = protein
                       organism = synthetic construct
SEQUENCE: 9
LAESAFSGVA RGDVRGGK                                              18

SEQ ID NO: 10          moltype = AA  length = 19
FEATURE                Location/Qualifiers
REGION                 1..19
                       note = Synthetic peptide
SITE                   19
                       note = MISC_FEATURE - C-terminal lysine with an azide
                        substitution on the side chain
SITE                   19
                       note = MISC_FEATURE - C-terminal amide
source                 1..19
                       mol_type = protein
                       organism = synthetic construct
SEQUENCE: 10
ALAESAFSGV ARGDVRGGK                                             19

SEQ ID NO: 11          moltype = AA  length = 20
FEATURE                Location/Qualifiers
REGION                 1..20
                       note = Synthetic peptide
SITE                   20
                       note = MISC_FEATURE - C-terminal lysine with an azide
                        substitution on the side chain
SITE                   20
                       note = MISC_FEATURE - C-terminal amide
source                 1..20
                       mol_type = protein
                       organism = synthetic construct
SEQUENCE: 11
EALAESAFSG VARGDVRGGK                                            20

SEQ ID NO: 12          moltype = AA  length = 5
FEATURE                Location/Qualifiers
REGION                 1..5
                       note = test peptide
source                 1..5
                       mol_type = protein
                       organism = synthetic construct
SEQUENCE: 12
AALAY                                                            5

SEQ ID NO: 13          moltype = DNA  length = 34
FEATURE                Location/Qualifiers
misc_feature           1..34
                       note = test DNA oligomer
misc_feature           1
                       note = 5' - phosphorylated
misc_feature           22
                       note = amino-modifier C6-coupled thymine
source                 1..34
                       mol_type = other DNA
                       organism = synthetic construct
SEQUENCE: 13
caagttctca gtaatgcgta gtccgcgaca ctag                            34
```